United States Patent
Iwakoshi et al.

(10) Patent No.: US 8,796,306 B2
(45) Date of Patent: *Aug. 5, 2014

(54) NOXIOUS ARTHROPOD CONTROLLING COMPOSITION AND HETEROCYCLIC COMPOUND

(75) Inventors: Mitsuhiko Iwakoshi, Toyonaka (JP); Hayato Takyo, Koshigaya (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/805,070

(22) PCT Filed: Jun. 17, 2011

(86) PCT No.: PCT/JP2011/064491
§ 371 (c)(1),
(2), (4) Date: Dec. 18, 2012

(87) PCT Pub. No.: WO2011/162364
PCT Pub. Date: Dec. 29, 2011

(65) Prior Publication Data
US 2013/0090353 A1    Apr. 11, 2013

(30) Foreign Application Priority Data
Jun. 23, 2010  (JP) .................... 2010-142396

(51) Int. Cl.
*A61K 31/44* (2006.01)
*C07D 471/02* (2006.01)
*C07D 405/04* (2006.01)

(52) U.S. Cl.
CPC .................. *C07D 405/04* (2013.01)
USPC .......................... 514/302; 546/115

(58) Field of Classification Search
CPC .................................................. C07D 405/04
See application file for complete search history.

(56) References Cited

U.S. PATENT DOCUMENTS

| | | | | |
|---|---|---|---|---|
| 4,210,655 A | * | 7/1980 | Schenker et al. | 514/320 |
| 5,849,765 A | | 12/1998 | Curtis et al. | |
| 8,242,133 B2 | * | 8/2012 | Iwakoshi et al. | 514/302 |
| 8,445,522 B2 | * | 5/2013 | Iwakoshi et al. | 514/375 |
| 2002/0137744 A1 | | 9/2002 | De Nanteuil et al. | |

FOREIGN PATENT DOCUMENTS

| | | |
|---|---|---|
| CH | 592656 A5 | 10/1977 |
| CH | 605924 A5 | 10/1978 |
| CH | 605926 A5 | 10/1978 |
| CH | 610588 A5 | 4/1979 |
| CH | 610898 A5 | 5/1979 |
| CH | 611617 A5 | 6/1979 |
| CH | 611618 A5 | 6/1979 |
| CH | 611619 A5 | 6/1979 |
| CH | 613450 A5 | 9/1979 |
| CH | 613961 A5 | 10/1979 |
| CH | 613962 A5 | 10/1979 |
| DE | 2653147 A1 | 6/1977 |
| DE | 2909754 A1 | 9/1980 |
| EP | 1217002 A1 | 6/2002 |
| GB | 1041525 A | 9/1966 |
| JP | 2005-139106 A | 6/2005 |
| WO | 2004041201 A2 | 5/2004 |
| WO | 2007010085 A2 | 1/2007 |
| WO | 2007091106 A2 | 8/2007 |
| WO | 2009019504 A1 | 2/2009 |

OTHER PUBLICATIONS

Silverman, R. "The Organic Chemistry of Drug Design and Drug Action," 2004, Elsevier, pp. 29-32.*
CAPLUS 1966:456756.*
Int'l Search Report issued Jul. 19, 2011 in Int'l Application No. PCT/JP2011/064491.
Alvey et al, "A new synthetic access to furo[3,2-f]chromene analogues of an antimycobacterial", Bioorganic & Medicinal Chemistry, vol. 16, pp. 8264-8272 (2008).
Lechel et al, "Novel Furo-pyridine Derivatives via Sonogashira Reactions of Functionalized Pyridines", European Journal of Organic Chemistry, vol. 21, pp. 3647-3655 (2008).
Watanabe et al, "Syntheses of 4-(Benzo[b]furan-2 or 3-yl)- and 4-(Benzo[b]-thiophen-3-yl)piperidines with 5-HT2 Antagonist Activity", Journal of Heterocyclic Chemistry, vol. 30, pp. 445-451 (1993).
Int'l Preliminary Report on Patentability issued Jan. 24, 2013 in Int'l Application No. PCT/JP2011/064491.

* cited by examiner

*Primary Examiner* — Heidi Reese
(74) *Attorney, Agent, or Firm* — Panitch Schwarze Belisario & Nadel LLP

(57) ABSTRACT

A noxious arthropod controlling composition comprising a heterocyclic compound represented by the formula (1) [wherein, $A^1$ and $A^2$ represent =$C(R^6)$—, nitrogen and so on, $R^1$ represents a halogen and so on, $R^3$ and $R^4$ represent optionally substituted C1 to C4 chain hydrocarbon group and so on, $R^5$ represents a hydrogen and so on, n represents 0 or 1] as an active ingredient has an excellent effect for controlling noxious arthropods.

(1)

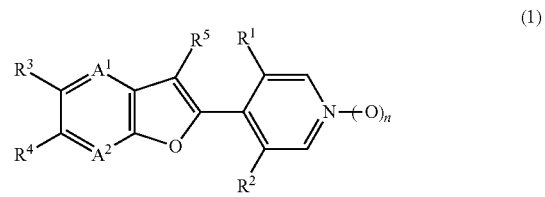

14 Claims, No Drawings

# NOXIOUS ARTHROPOD CONTROLLING COMPOSITION AND HETEROCYCLIC COMPOUND

CROSS-REFERENCE TO RELATED APPLICATION

This application is a Section 371 of International Application No. PCT/JP2011/064491, filed Jun. 17, 2011, which was published in the Japanese language on Dec. 29, 2011, under International Publication No. WO 2011/162364 A1, and the disclosure of which is incorporated herein by reference.

TECHNICAL FIELD

The present invention relates to a noxious arthropod controlling composition and a heterocyclic compound.

BACKGROUND ART

JP-A-58-4781 describes a benzofuran compound as a production intermediate of a pharmaceutical compound. British Patent Publication No. 1,041,525 describes a benzofuran compound as a pharmaceutical compound and a production method thereof.

DISCLOSURE OF THE INVENTION

An object of the present invention is to provide a composition having an excellent noxious arthropod controlling effect.

The present inventors have intensively studied to solve the above-described object and consequently found that a heterocyclic compound represented by the following formula (1) has an excellent noxious arthropod controlling effect, and thus the present invention has been accomplished.

The present invention is as follows.

[1] A noxious arthropod controlling composition comprising, as an active ingredient, a heterocyclic compound represented by the formula (1):

$$\text{(structure with } R^3, A^1, R^5, R^1, R^4, A^2, O, R^2, N\text{—}(O)_n\text{)} \tag{1}$$

wherein $A^1$ and $A^2$ are the same or different, and each represent nitrogen or $=C(R^6)-$, $R^1$ represents a C1 to C6 chain hydrocarbon group optionally substituted with at least one selected from group X, a C3 to C6 alicyclic hydrocarbon group optionally substituted with at least one selected from group X, a phenyl group optionally substituted with at least one selected from group Y, a five-membered heterocyclic group optionally substituted with at least one selected from group Y, a six-membered heterocyclic group optionally substituted with at least one selected from group Y, $-OR^7$, $-S(O)_mR^7$, $-NR^7R^8$, $-NR^7C(O)R^9$, $-NR^7CO_2R^{10}$, $-C(O)R^{11}$, $-C(NOR^7)R^{11}$, $-CO_2R^{11}$, $-CONR^7R^8$, $-CONR^{11}R^{12}R^{13}$, a cyano group, a nitro group, a halogen, or hydrogen, $R^2$ represents a C1 to C6 chain hydrocarbon group optionally substituted with at least one selected from group X, $-OR^7$, $-S(O)_mR^7$, $-NR^7R^8$, a halogen, or hydrogen, $R^3$ and $R^4$ are the same or different, and each represent a C1 to C4 chain hydrocarbon group optionally substituted with at least one selected from group X, a C3 to C6 alicyclic hydrocarbon group optionally substituted with at least one selected from group X, $-OR^{14}$, $-S(O)_mR^{14}$, a halogen, or hydrogen (wherein either $R^3$ or $R^4$ is a C1 to C4 chain hydrocarbon group optionally substituted with at least one selected from group X, a C3 to C6 alicyclic hydrocarbon group optionally substituted with at least one selected from group X, $-OR^{14}$, or $-S(O)_mR^{14}$), or $R^3$ and $R^4$ taken together with the atoms to which $R^3$ and $R^4$ are attached may form a five-membered ring or six-membered ring optionally substituted with at least one selected from group Z, $R^5$ represents a C1 to C3 alkyl group optionally substituted with at least one halogen or hydrogen, $R^6$ represents a C1 to C3 alkyl group optionally substituted with at least one halogen or hydrogen, $R^7$ and $R^8$ are the same or different, and each represent a C1 to C6 chain hydrocarbon group optionally substituted with at least one selected from group X, a C4 to C7 cycloalkylmethyl group optionally substituted with at least one selected from group X, a C3 to C6 alicyclic hydrocarbon group optionally substituted with at least one selected from group X, a phenyl group optionally substituted with at least one selected from group Y, a benzyl group optionally substituted with at least one selected from group Y, a five-membered heterocyclic group optionally substituted with at least one selected from group Y, a six-membered heterocyclic group optionally substituted with at least one selected from group Y, or hydrogen (wherein when m in $-S(O)_mR^7$ is 1 or 2, $R^7$ is not hydrogen), $R^9$ represents a C1 to C6 chain hydrocarbon group optionally substituted with at least one selected from group X, a C3 to C6 alicyclic hydrocarbon group optionally substituted with at least one selected from group X, or a phenyl group optionally substituted with at least one selected from group Y, $R^{10}$ represents a C1 to C4 alkyl group optionally substituted with at least one halogen, $R^{11}$ represents a C1 to C4 alkyl group optionally substituted with at least one halogen or hydrogen, $R^{12}$ and $R^{13}$ are the same or different, and each represent a C1 to C4 alkyl group optionally substituted with at least one halogen, a C2 to C4 alkoxycarbonyl group, or hydrogen, $R^{14}$ represents a C1 to C4 chain hydrocarbon group optionally substituted with at least one selected from group X, m represents 0, 1, or 2, and n represents 0 or 1:

Group X: a group consisting of C1 to C4 alkoxy groups optionally substituted with at least one halogen and halogens;

Group Y: a group consisting of C1 to C4 alkyl groups optionally substituted with at least one halogen, C1 to C4 alkoxy groups optionally substituted with at least one halogen, a cyano group, a nitro group and halogens; and Group Z: a group consisting of C1 to C3 alkyl groups optionally substituted with at least one halogen and halogens.

[2] The noxious arthropod controlling composition according to [1], wherein the heterocyclic compound represented by the formula (1) is a heterocyclic compound wherein $R^6$ is hydrogen.

[3] The noxious arthropod controlling composition according to [1] or [2], wherein the heterocyclic compound represented by the formula (1) is a heterocyclic compound wherein $R^2$ is hydrogen.

[4] The noxious arthropod controlling composition according to any one of [1] to [3], wherein the heterocyclic compound represented by the formula (1) is a heterocyclic compound wherein $R^5$ is hydrogen.

[5] The noxious arthropod controlling composition according to any one of [1] to [4], wherein the heterocyclic compound represented by the formula (1) is a heterocyclic compound wherein $R^1$ is a C1 to C6 chain hydrocarbon group optionally substituted with at least one selected from group X, —$OR^7$, —$S(O)_mR^7$, —$NR^7R^8$, —$NR^7C(O)R^9$, —$NR^7CO_2R^{10}$, —$C(O)R^{11}$, —$C(NOR^7)R^{11}$, —$CO_2R^{11}$, —$CONR^7R^8$, —$CONR^{11}NR^{12}R^{13}$, a cyano group, a nitro group, a halogen, or hydrogen, $R^7$ and $R^8$ are the same or different, and each are a C1 to C6 chain hydrocarbon group optionally substituted with at least one selected from group X or hydrogen (wherein when m in —$S(O)_mR^7$ is 1 or 2, $R^7$ represents a C1 to C6 hydrocarbon group optionally substituted with at least one selected from group X), and $R^9$ is a C1 to C6 chain hydrocarbon group optionally substituted with at least one selected from group X.

[6] The noxious arthropod controlling composition according to any one of [1] to [4], wherein the heterocyclic compound represented by the formula (1) is a heterocyclic compound wherein $R^1$ is a C1 to C6 chain hydrocarbon group optionally substituted with at least one selected from group X, —$OR^7$, —$S(O)_mR^7$, —$NR^7R^8$, a halogen, or hydrogen, $R^7$ is a C1 to C6 chain hydrocarbon group optionally substituted with at least one selected from group X, and $R^8$ is a C1 to C6 chain hydrocarbon group optionally substituted with at least one selected from group X or hydrogen.

[7] A method for controlling a noxious arthropod comprising applying, to noxious arthropods or habitats of noxious arthropods, an effective amount of a heterocyclic compound represented by the formula (1):

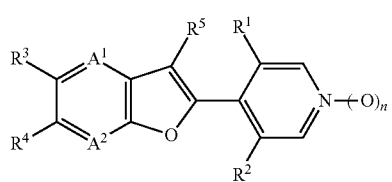

(1)

wherein $A^1$ and $A^2$ are the same or different, and each represent nitrogen or =$C(R^6)$—, $R^1$ represents a C1 to C6 chain hydrocarbon group optionally substituted with at least one selected from group X, a C3 to C6 alicyclic hydrocarbon group optionally substituted with at least one selected from group X, a phenyl group optionally substituted with at least one selected from group Y, a five-membered heterocyclic group optionally substituted with at least one selected from group Y, a six-membered heterocyclic group optionally substituted with at least one selected from group Y, —$OR^7$, —$S(O)_mR^7$, —$NR^7R^8$, —$NR^7C(O)R^9$, —$NR^7CO_2R^{10}$, —$C(O)R^{11}$, —$C(NOR^7)R^{11}$, —$CO_2R^{11}$, —$CONR^7R^8$, —$CONR^{11}NR^{12}R^{13}$, a cyano group, a nitro group, a halogen, or hydrogen, $R^2$ represents a C1 to C6 chain hydrocarbon group optionally substituted with at least one selected from group X, —$OR^7$, —$S(O)_mR^7$, —$NR^7R^8$, a halogen, or hydrogen, $R^3$ and $R^4$ are the same or different, and each represent a C1 to C4 chain hydrocarbon group optionally substituted with at least one selected from group X, a C3 to C6 alicyclic hydrocarbon group optionally substituted with at least one selected from group X, —$OR^{14}$, —$S(O)_mR^{14}$, a halogen, or hydrogen (wherein either $R^3$ or $R^4$ is a C1 to C4 chain hydrocarbon group optionally substituted with at least one selected from group X, a C3 to C6 alicyclic hydrocarbon group optionally substituted with at least one selected from group X, —$OR^{14}$, or —$S(O)_mR^{14}$), or $R^3$ and $R^4$ taken together with the atoms to which $R^3$ and $R^4$ are attached may form a five-membered ring or six-membered ring optionally substituted with at least one selected from group z, $R^5$ represents a C1 to C3 alkyl group optionally substituted with at least one halogen or hydrogen, $R^6$ represents a C1 to C3 alkyl group optionally substituted with at least one halogen or hydrogen, $R^7$ and $R^8$ are the same or different, and each represent a C1 to C6 chain hydrocarbon group optionally substituted with at least one selected from group X, a C4 to C7 cycloalkylmethyl group optionally substituted with at least one selected from group X, a C3 to C6 alicyclic hydrocarbon group optionally substituted with at least one selected from group X, a phenyl group optionally substituted with at least one selected from group Y, a benzyl group optionally substituted with at least one selected from group Y, a five-membered heterocyclic group optionally substituted with at least one selected from group Y, a six-membered heterocyclic group optionally substituted with at least one selected from group Y, or hydrogen (wherein when m in —$S(O)_mR^7$ is 1 or 2, $R^7$ is not hydrogen), $R^9$ represents a C1 to C6 chain hydrocarbon group optionally substituted with at least one selected from group X, a C3 to C6 alicyclic hydrocarbon group optionally substituted with at least one selected from group X, or a phenyl group optionally substituted with at least one selected from group Y, $R^{10}$ represents a C1 to C4 alkyl group optionally substituted with at least one halogen, $R^{11}$ represents a C1 to C4 alkyl group optionally substituted with at least one halogen or hydrogen, $R^{12}$ and $R^{13}$ are the same or different, and each represent a C1 to C4 alkyl group optionally substituted with at least one halogen, a C2 to C4 alkoxycarbonyl group, or hydrogen, $R^{14}$ represents a C1 to C4 chain hydrocarbon group optionally substituted with at least one selected from group X, m represents 0, 1, or 2, and n represents 0 or 1:

Group X: a group consisting of C1 to C4 alkoxy groups optionally substituted with at least one halogen and halogens;

Group Y: a group consisting of C1 to C4 alkyl groups optionally substituted with at least one halogen, C1 to C4 alkoxy groups optionally substituted with at least one halogen, a cyano group, a nitro group and halogens; and Group Z: a group consisting of C1 to C3 alkyl groups optionally substituted with at least one halogen and halogens.

[8] The method for controlling a noxious arthropod according to [7], wherein the heterocyclic compound represented by the formula (1) is a heterocyclic compound wherein $R^6$ is hydrogen.

[9] The method for controlling a noxious arthropod according to [7] or [8], wherein the heterocyclic compound represented by the formula (1) is a heterocyclic compound wherein $R^2$ is hydrogen.

[10] The method for controlling a noxious arthropod according to any one of [7] to [9], wherein the heterocyclic compound represented by the formula (1) is a heterocyclic compound wherein $R^5$ is hydrogen.

[11] The method for controlling a noxious arthropod according to any one of [7] to [10], wherein the heterocyclic compound represented by the formula (1) is a heterocyclic compound wherein $R^1$ is a C1 to C6 chain hydrocarbon group optionally substituted with at least one selected from group X, —OR⁷, —S(O)ₘR⁷, —NR⁷R⁸, —NR⁷C(O)R⁹, —NR⁷CO₂R¹⁰, —C(O)R¹¹, —C(NOR⁷)¹¹, —CO₂R¹¹, —CONR⁷R⁸, —CONR¹¹R¹²R¹³, a cyano group, a nitro group, a halogen, or hydrogen, R⁷ and R⁸ are the same or different, and each are a C1 to C6 chain hydrocarbon group optionally substituted with at least one selected from group X or hydrogen (wherein when m in —S(O)ₘR⁷ is 1 or 2, R⁷ represents a C1 to C6 chain hydrocarbon group optionally substituted with at least one selected from group X), and R⁹ is a C1 to C6 chain hydrocarbon group optionally substituted with at least one selected from group X.

[12] The method for controlling a noxious arthropod according to any one of [7] to [10], wherein the heterocyclic compound represented by the formula (1) is a heterocyclic compound wherein R¹ is a C1 to C6 chain hydrocarbon group optionally substituted with at least one selected from group X, —OR⁷, —S(O)ₘR⁷, —NR⁷R⁸, a halogen, or hydrogen, R⁷ is a C1 to C6 chain hydrocarbon group optionally substituted with at least one selected from group X, and R⁸ is a C1 to C6 chain hydrocarbon group optionally substituted with at least one selected from group X or hydrogen.

[13] Use of a heterocyclic compound represented by the formula (1) for controlling a noxious arthropod:

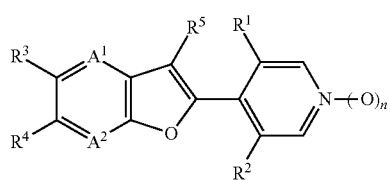

(1)

wherein

A¹ and A² are the same or different, and each represent nitrogen or =C(R⁶)—,

R¹ represents a C1 to C6 chain hydrocarbon group optionally substituted with at least one selected from group X, a C3 to C6 alicyclic hydrocarbon group optionally substituted with at least one selected from group X, a phenyl group optionally substituted with at least one selected from group Y, a five-membered heterocyclic group optionally substituted with at least one selected from group Y, a six-membered heterocyclic group optionally substituted with at least one selected from group Y, —OR⁷, —S(O)ₘR⁷, —NR⁷R⁸, —NR⁷C(O)R⁹, —NR⁷CO₂R¹⁰, —C(O)R¹¹, —C(NOR⁷)R¹¹, —CO₂R¹¹, —CONR⁷R⁸, —CONR¹¹NR¹²R¹³, a cyano group, a nitro group, a halogen, or hydrogen, R² represents a C1 to C6 chain hydrocarbon group optionally substituted with at least one selected from group X, —OR⁷, —S(O)ₘR⁷, —NR⁷R⁸, a halogen, or hydrogen, R³ and R⁴ are the same or different, and each represent a C1 to C4 chain hydrocarbon group optionally substituted with at least one selected from group X, a C3 to C6 alicyclic hydrocarbon group optionally substituted with at least one selected from group X, —OR¹⁴, —S(O)ₘR¹⁴, a halogen, or hydrogen (wherein either R³ or R⁴ is a C1 to C4 chain hydrocarbon group optionally substituted with at least one selected from group X, a C3 to C6 alicyclic hydrocarbon group optionally substituted with at least one selected from group X, —OR¹⁴, or —S(O)ₘR¹⁴), or R³ and R⁴ taken together with the atoms to which R³ and R⁴ are attached may form a five-membered ring or six-membered ring optionally substituted with at least one selected from group Z, R⁵ represents a C1 to C3 alkyl group optionally substituted with at least one halogen or hydrogen, R⁶ represents a C1 to C3 alkyl group optionally substituted with at least one halogen or hydrogen, R⁷ and R⁸ are the same or different, and each represent a C1 to C6 chain hydrocarbon group optionally substituted with at least one selected from group X, a C4 to C7 cycloalkylmethyl group optionally substituted with at least one selected from group X, a C3 to C6 alicyclic hydrocarbon group optionally substituted with at least one selected from group X, a phenyl group optionally substituted with at least one selected from group Y, a benzyl group optionally substituted with at least one selected from group Y, a five-membered heterocyclic group optionally substituted with at least one selected from group Y, a six-membered heterocyclic group optionally substituted with at least one selected from group Y, or hydrogen (wherein when m in —S(O)ₘR⁷ is 1 or 2, R⁷ is not hydrogen), R⁹ represents a C1 to C6 chain hydrocarbon group optionally substituted with at least one selected from group X, a C3 to C6 alicyclic hydrocarbon group optionally substituted with at least one selected from group X, or a phenyl group optionally substituted with at least one selected from group Y, R¹⁰ represents a C1 to C4 alkyl group optionally substituted with at least one halogen, R¹¹ represents a C1 to C4 alkyl group optionally substituted with at least one halogen or hydrogen, R¹² and R¹³ are the same or different, and each represent a C1 to C4 alkyl group optionally substituted with at least one halogen, a C2 to C4 alkoxycarbonyl group, or hydrogen, R¹⁴ represents a C1 to C4 chain hydrocarbon group optionally substituted with at least one selected from group X, m represents 0, 1, or 2, and n represents 0 or 1:

Group X: a group consisting of C1 to C4 alkoxy groups optionally substituted with at least one halogen and halogens;

Group Y: a group consisting of C1 to C4 alkyl groups optionally substituted with at least one halogen, C1 to C4 alkoxy groups optionally substituted with at least one halogen, a cyano group, a nitro group and halogens; and Group Z: a group consisting of C1 to C3 alkyl groups optionally substituted with at least one halogen and halogens.

[14] A heterocyclic compound represented by the formula (2):

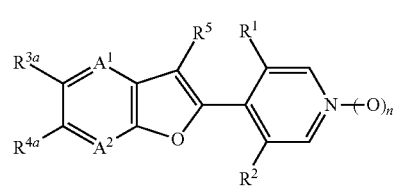

(2)

wherein

A¹ and A² are the same or different, and each represent nitrogen or =C(R⁶)—,

R¹ represents a C1 to C6 chain hydrocarbon group optionally substituted with at least one selected from group X, a C3 to C6 alicyclic hydrocarbon group optionally substituted with at least one selected from group X, a phenyl group optionally substituted with at least one selected from group Y, a five-membered heterocyclic group optionally substituted with at least one selected from group Y, a six-membered heterocyclic group optionally substituted with at least one selected from group Y, —OR⁷, —S(O)ₘR⁷, —NR⁷R⁸, —NR⁷C(O)R⁹, —NR⁷CO₂R¹⁰, —C(O)R¹¹, —C(NOR⁷)R¹¹, —CO₂R¹¹, —CONR⁷R⁸, —CONR¹²R¹³, a cyano group, a nitro group, or a halogen, $R^2$ represents a C1 to C6 chain hydrocarbon group optionally substituted with at least one selected from group X, —$OR^7$, —$S(O)_m R^7$, —$NR^7 R^8$, a halogen, or hydrogen, $R^{3a}$ and $R^{4a}$ are the same or different, and each represent a C1 to C4 chain hydrocarbon group substituted with at least one halogen, —$OR^{14a}$, —$S(O)_m R^{14a}$, a halogen, or hydrogen (wherein either $R^{3a}$ and $R^{4a}$ is a C1 to C4 chain hydrocarbon group substituted with at least one halogen, —$OR^{14a}$, or —$S(O)_m R^{14a}$), or $R^{3a}$ and $R^{4a}$ taken together with the atoms to which $R^{3a}$ and $R^{4a}$ are attached may form a five-membered ring or six-membered ring substituted with at least one halogen, $R^5$ represents a C1 to C3 alkyl group optionally substituted with at least one halogen or hydrogen, $R^6$ represents a C1 to C3 alkyl group optionally substituted with at least one halogen or hydrogen, $R^7$ and $R^8$ are the same or different, and each represent a C1 to C6 chain hydrocarbon group optionally substituted with at least one selected from group X, a C4 to C7 cycloalkylmethyl group optionally substituted with at least one selected from group X, a C3 to C6 alicyclic hydrocarbon group optionally substituted with at least one selected from group X, a phenyl group optionally substituted with at least one selected from group Y, a benzyl group optionally substituted with at least one selected from group Y, a five-membered heterocyclic group optionally substituted with at least one selected from group Y, a six-membered heterocyclic group optionally substituted with at least one selected from group Y, or hydrogen (wherein when m in —$S(O)_m R^7$ is 1 or 2, $R^7$ is not hydrogen), $R^9$ represents a C1 to C6 chain hydrocarbon group optionally substituted with at least one selected from group X, a C3 to C6 alicyclic hydrocarbon group optionally substituted with at least one selected from group X, or a phenyl group optionally substituted with at least one selected from group Y, $R^{10}$ represents a C1 to C4 alkyl group optionally substituted with at least one halogen, $R^{11}$ represents a C1 to C4 alkyl group optionally substituted with at least one halogen or hydrogen, $R^{12}$ and $R^{13}$ are the same or different, and each represent a C1 to C4 alkyl group optionally substituted with at least one halogen, a C2 to C4 alkoxycarbonyl group, or hydrogen, $R^{14a}$ represents a C1 to C4 chain hydrocarbon group substituted with at least one halogen, m represents 0, 1, or 2, and n represents 0 or 1:

Group X: a group consisting of C1 to C4 alkoxy groups optionally substituted with at least one halogen and halogens; and Group Y: a group consisting of C1 to C4 alkyl groups optionally substituted with at least one halogen, C1 to C4 alkoxy groups optionally substituted with at least one halogen, a cyano group, a nitro group, and halogens.

[15] The heterocyclic compound according to [14], wherein $R^6$ is hydrogen.

[16] The heterocyclic compound according to [14] or [15], wherein $R^2$ is hydrogen.

[17] The heterocyclic compound according to any one of [14] to [16], wherein $R^5$ is hydrogen.

[18] The heterocyclic compound according to any one of [14] to [17], wherein $R^1$ is a C1 to C6 chain hydrocarbon group optionally substituted with at least one selected from group X, —$OR^7$, —$S(O)_m R^7$, —$NR^7 R^8$, —$NR^7 C(O)R^9$, —$NR^7 CO_2 R^{10}$, —$C(O)R^{11}$, —$C(NOR^7)R^{11}$, —$CONR^7 R^8$, —$CONR^{11} NR^{12} R^{13}$, a cyano group, a nitro group, or a halogen, $R^7$ and $R^8$ are the same or different, and each are a C1 to C6 chain hydrocarbon group optionally substituted with at least one selected from group X or hydrogen (wherein when m in —$S(O)_m R^7$ is 1 or 2, $R^7$ represents a C1 to C6 chain hydrocarbon group optionally substituted with at least one selected from group X), and $R^9$ is a C1 to C6 chain hydrocarbon group optionally substituted with at least one selected from group X.

[19] The heterocyclic compound according to any one of [14] to [17], wherein $R^1$ is a C1 to C6 chain hydrocarbon group optionally substituted with at least one selected from group X, —$OR^7$, —$S(O)_m R^7$, —$NR^7 R^8$, or a halogen, $R^7$ is a C1 to C6 chain hydrocarbon group optionally substituted with at least one selected from group X, and $R^8$ is a C1 to C6 chain hydrocarbon group optionally substituted with at least one selected from group X or hydrogen.

Hereinafter, the heterocyclic compound represented by the formula (1) may be referred to as "the present active compound", and the noxious arthropod control composition of [1] may be referred to as "the composition of the present invention".

The composition of the present invention generally contains the present active compound and an inert carrier.

The substituents used in the description of the present specification will be described below with reference to examples. Here, in the present specification, "C4 to C7" shown in "C4 to C7 cycloalkylmethyl group" means that the total number of carbon atoms constituting the cycloalkylmethyl group is within the range from 4 to 7.

The "halogen" in the present active compound means fluorine, chlorine, bromine, and iodine.

Examples of the "C1 to C6 chain hydrocarbon group optionally substituted with at least one selected from group X" represented by $R^1$ include: C1 to C6 alkyl groups such as a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, 3,3-dimethylbutyl group, and a hexyl group;

C1 to C6 alkyl groups substituted with at least one selected from group X, such as a methoxymethyl group, an ethoxymethyl group, a 1-methoxyethyl group, and a trifluoromethyl group;

C2 to C6 alkenyl groups such as a vinyl group, a 1-propenyl group, a 2-propenyl group, an isopropenyl group, a 2-methyl-1-propenyl group, a 1-butenyl group, a 2-butenyl group, a 3-butenyl group, a 1-pentenyl group, and a 1-hexenyl group;

C2 to C6 alkenyl groups substituted with at least one selected from group X, such as a 3,3-difluoro-2-propenyl group and a 3-methoxy-1-propenyl group;

C2 to C6 alkynyl groups such as an ethynyl group, a propargyl group, a 1-butynyl group, a 2-butynyl group, a 3-butynyl group, a 3,3-dimethyl-1-butynyl group, a 1-pentynyl group, and a 1-hexynyl group; and C2 to C6 alkynyl groups substituted with at least one selected from group X, such as a 3-methoxy-1-propynyl group.

Examples of the "C3 to C6 alicyclic hydrocarbon group optionally substituted with at least one selected from group X" represented by $R^1$ include a cyclopropyl group, a cyclobutyl group, a cyclopentyl group, and a cyclohexyl group.

Examples of the "phenyl group optionally substituted with at least one selected from group Y" represented by $R^1$ include a phenyl group, a 2-chlorophenyl group, a 3-chlorophenyl group, a 4-chlorophenyl group, a 2-methylphenyl group, a 3-methylphenyl group, a 4-methylphenyl group, a 2-methoxyphenyl group, a 3-methoxyphenyl group, a 4-methoxyphenyl group, a 2-(trifluoromethyl)phenyl group, a 3-(trifluoromethyl)phenyl group, a 4-(trifluoromethyl)phenyl group, a 2-nitrophenyl group, a 3-nitrophenyl group, a 4-nitrophenyl group, a 2-cyanophenyl group, a 3-cyanophenyl group, and a 4-cyanophenyl group.

Examples of the "five-membered heterocyclic group optionally substituted with at least one selected from group Y" represented by $R^1$ include: five-membered saturated heterocyclic groups such as a pyrrolidin-1-yl group; and five-membered aromatic heterocyclic groups such as a pyrazol-1-yl group, a 3-chloro-pyrazol-1-yl group, a 3-bromopyrazol-1-yl group, a 3-nitropyrazol-1-yl group, a 3-methylpyrazol-1-yl group, 3-(trifluoromethyl)pyrazol-1-yl group, a 4-methylpyrazol-1-yl group, a 4-chloropyrazol-1-yl group, a 4-bromopyrazol-1-yl group, a 4-cyanopyrazol-1-yl group, an imidazol-1-yl group, a 4-(trifluoromethyl)imidazol-1-yl group, a pyrrol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-furyl group, a 3-furyl group, a 2-thienyl group, and a 3-thienyl group.

Examples of the "six-membered heterocyclic group optionally substituted with at least one selected from group Y" represented by $R^1$ include:

six-membered saturated heterocyclic groups such as a piperidyl group, a morpholino group, a thiomorpholino group, and a 4-methylpiperazin-1-yl group; and six-membered aromatic heterocyclic groups such as a 2-pyridyl group, a 3-pyridyl group, and a 4-pyridyl group.

Examples of the "C1 to C6 chain hydrocarbon group optionally substituted with at least one selected from group X" represented by $R^2$ include: C1 to C6 alkyl groups such as a methyl group, an ethyl group, a propyl group, an isopropyl group, a butyl group, an isobutyl group, a sec-butyl group, tert-butyl group, a pentyl group, a 2,2-dimethylpropyl group, a 3-methylbutyl group, a 2,3-dimethylbutyl group, a 3,3-dimethylbutyl group, and a hexyl group;

C1 to C6 alkyl groups substituted with at least one selected from group X, such as a methoxymethyl group, an ethoxymethyl group, a 1-methoxyethyl group, and a trifluoromethyl group;

C2 to C6 alkenyl groups such as a vinyl group, a 1-propenyl group, a 2-propenyl group, an isopropenyl group, a 2-methyl-1-propenyl group, a 1-butenyl group, a 2-butenyl group, a 3-butenyl group, a 1-pentenyl group, and a 1-hexenyl group;

C2 to C6 alkenyl groups substituted with at least one selected from group X, such as a 3,3-difluoro-2-propenyl group and a 3-methoxy-1-propenyl group;

C2 to C6 alkynyl groups such as an ethynyl group, a propargyl group, a 1-butynyl group, a 2-butynyl group, a 3-butynyl group, a 3,3-dimethyl-1-butynyl group, a 1-pentynyl group, and a 1-hexynyl group; and C2 to C6 alkynyl groups substituted with at least one selected from group X, such as a 3-methoxy-1-propynyl group.

Examples of the "C1 to C4 chain hydrocarbon group optionally substituted with at least one selected from group X" represented by $R^3$ or $R^4$ include: C1 to C4 alkyl groups such as a methyl group, an ethyl group, a propyl group, an isopropyl group, an isobutyl group, a sec-butyl group, and a tert-butyl group;

C1 to C4 alkyl groups substituted with at least one selected from group X, such as a methoxymethyl group, a 1-methoxyethyl group, a 1,1-difluoroethyl group, a trifluoromethyl group, a pentafluoroethyl group, and a heptafluoroisopropyl group;

C2 to C4 alkenyl groups such as a vinyl group, a 1-propenyl group, a 2-propenyl group, an isopropenyl group, a 1-methyl-1-propenyl group, and a 1-methyl-2-propenyl group;

C2 to C4 alkenyl groups substituted with at least one selected from group X;

C2 to C4 alkynyl groups such as an ethynyl group, a propargyl group, and a 1-methyl-2-propynyl group; and C3 to C4 alkynyl groups substituted with at least one selected from group X.

Examples of the C3 to C6 alicyclic hydrocarbon group represented by $R^3$ or $R^4$ include a cyclopropyl group, a 1-methylcyclopropyl group, a cyclobutyl group, a cyclopentyl group, a 1-methylcyclopentyl group, a 1-cyclopentenyl group, and a cyclohexyl group.

Examples of the "C1 to C3 alkyl group optionally substituted with at least one halogen" represented by $R^5$ include a methyl group, an ethyl group, a propyl group, an isopropyl group, and a trifluoromethyl group.

Examples of the "C1 to C3 alkyl group optionally substituted with at least one halogen" represented by $R^6$ include a methyl group, an ethyl group, a propyl group, an isopropyl group, and a trifluoromethyl group.

Examples of the "C1 to C6 chain hydrocarbon group optionally substituted with at least one selected from group X" represented by $R^7$ or $R^8$ include: C1 to C6 alkyl groups such as a methyl group, an ethyl group, a propyl group, an isopropyl group, a butyl group, an isobutyl group, a sec-butyl group, a tert-butyl group, a 1-methylbutyl group, a 2-methylbutyl group, a 3-methylbutyl group, a 1-ethylpropyl group, a 1,2-dimethylpropyl group, a 2,2-dimethylpropyl group, a pentyl group, a 1,2-dimethylbutyl group, a 2,2-dimethylbutyl group, a 1,3-dimethylbutyl group, a 1-methylpentyl group, a 2-methylpentyl group, a 3-methylpentyl group, a 4-methylpentyl group, and a hexyl group;

C1 to C6 alkyl groups substituted with at least one selected from group X, such as a 2-methoxyethyl group, a 2-ethoxyethyl group, a difluoromethyl group, a trifluoromethyl group, a 2,2-difluoroethyl group, a 2,2,2-trifluoroethyl group, a 2,2,2-trichloroethyl group, a 1-methyl-2,2,2-trifluoroethyl group, a 1-methyl-2,2,2-trichloroethyl group, a 1,1,2,2-tetrafluoroethyl group, a 2,2-difluoropropyl group, and a 2,2,3,3-tetrafluoropropyl group;

C3 to C6 alkenyl groups such as a 2-propenyl group, a 1-methyl-2-propenyl group, a 2-methyl-2-propenyl group, a 2-butenyl group, a 3-butenyl group, a 1-methyl-2-butenyl group, and a 1-methyl-3-butenyl group;

C3 to 06 alkenyl groups substituted with at least one selected from group X, such as a 3,3-dichloro-2-propenyl group and a 3,3-difluoro-2-propenyl group; and C3 to C6 alkynyl groups optionally substituted with at least one selected from group X, such as a propargyl group, a 1-methyl-2-propynyl group, a 2-butynyl group, a 3-butynyl group, a 1-methyl-2-butynyl group, and a 1-methyl-3-butynyl group.

Examples of the C4 to C7 cycloalkylmethyl group represented by $R^7$ or $R^8$ include a cyclopropylmethyl group, a cyclobutylmethyl group, a cyclopentylmethyl group, and a cyclohexylmethyl group.

Examples of the C3 to C6 alicyclic hydrocarbon group represented by $R^7$ or $R^8$ include a cyclopropyl group, a cyclobutyl group, a cyclopentyl group, a cyclohexyl group, and a 2-cyclohexenyl group.

Examples of the "phenyl group optionally substituted with at least one selected from group Y" represented by $R^7$ or $R^8$ include a phenyl group, a 2-chlorophenyl group, a 3-chlorophenyl group, a 4-chlorophenyl group, a 2-methylphenyl group, a 3-methylphenyl group, a 4-methylphenyl group, a 2-methoxyphenyl group, a 3-methoxyphenyl group, a 4-methoxyphenyl group, a 2-(trifluoromethyl)phenyl group, a 3-(trifluoromethyl)phenyl group, a 4-(trifluoromethyl)phenyl group, a 2-cyanophenyl group, a 3-cyanophenyl group, a 4-cyanophenyl group, a 2-nitrophenyl group, a 3-nitrophenyl group, and a 4-nitrophenyl group.

Examples of the "benzyl group optionally substituted with at least one selected from group Y" represented by $R^7$ or $R^8$ include a benzyl group, a 2-chlorobenzyl group, a 3-chlorobenzyl group, a 4-chlorobenzyl group, a 2-methylbenzyl group, a 3-methylbenzyl group, a 4-methylbenzyl group, a 2-methoxybenzyl group, a 3-methoxybenzyl group, and a 4-methoxybenzyl group.

Examples of the "five-membered heterocyclic group" represented by $R^7$ or $R^8$ include five-membered aromatic heterocyclic groups such as a 2-thiazolyl group, a 2-thienyl group, and a 3-thienyl group.

Examples of the "six-membered heterocyclic group" represented by $R^7$ or $R^8$ include six-membered aromatic heterocyclic groups such as a 2-pyridyl group, a 3-pyridyl group, a 4-pyridyl group, a 2-pyrimidinyl group, and a 4-pyrimidinyl group.

Examples of the "C1 to C6 chain hydrocarbon group optionally substituted with at least one selected from group X" represented by $R^9$ include: C1 to C6 alkyl groups such as a methyl group, an ethyl group, a propyl group, an isopropyl group, a butyl group, an isobutyl group, a sec-butyl group, tert-butyl group, a 1-methylbutyl group, a 1-ethylpropyl group, a pentyl group, and a hexyl group;

C1 to C6 alkyl groups substituted with at least one selected from group X, such as a methoxymethyl group, a difluoromethyl group, a trifluoromethyl group, a trichloromethyl group, a pentafluoroethyl group, and a 1,1,2,2-tetrafluoroethyl group;

C2 to C6 alkenyl groups optionally substituted with at least one selected from group X, such as a vinyl group, a 1-propenyl group, a 2-propenyl group, an isopropenyl group, a 2,2,-dimethylethenyl group, a 1-butenyl group, a 2-butenyl group, and a 3,3,3-trifluoro-1-propenyl group; and C2 to C6 alkynyl groups optionally substituted with at least one selected from group X, such as a propargyl group, a 1-propynyl group, and a 3,3,3-trifluoro-1-propynyl group.

Examples of the C3 to C6 alicyclic hydrocarbon group represented by $R^9$ include a cyclopropyl group, a cyclobutyl group, a cyclopentyl group, and a cyclohexyl group.

Examples of the "phenyl group optionally substituted with at least one selected from group Y" represented by $R^9$ include a phenyl group, a 2-chlorophenyl group, a 3-chlorophenyl group, a 4-chlorophenyl group, a 2-methylphenyl group, a 3-methylphenyl group, a 4-methylphenyl group, a 2-methoxyphenyl group, a 3-methoxyphenyl group, a 4-methoxyphenyl group, a 2-(trifluoromethyl)phenyl group, a 3-(trifluoromethyl)phenyl group, a 4-(trifluoromethyl)phenyl group, a 2-cyanophenyl group, a 3-cyanophenyl group, a 4-cyanophenyl group, a 2-nitrophenyl group, a 3-nitrophenyl group, and a 4-nitrophenyl group.

Examples of the "C1 to C4 alkyl group optionally substituted with at least one halogen" represented by $R^{10}$ include a methyl group, an ethyl group, a 2,2,2-trifluoroethyl group, a propyl group, an isopropyl group, a butyl group, an isobutyl group, a sec-butyl group, and a tert-butyl group.

Examples of the "C1 to C4 alkyl group optionally substituted with at least one halogen" represented by $R^{11}$ include a methyl group, a trifluoromethyl group, a trichloromethyl group, an ethyl group, a 2,2,2-trifluoroethyl group, a pentafluoroethyl group, a propyl group, an isopropyl group, a butyl group, an isobutyl group, a sec-butyl group, and a tert-butyl group.

Examples of the "C1 to C4 alkyl group optionally substituted with at least one halogen" represented by $R^{12}$ or $R^{13}$ include a methyl group, an ethyl group, a 2,2,2-trifluoroethyl group, a propyl group, an isopropyl group, a butyl group, an isobutyl group, a sec-butyl group, and a tert-butyl group.

Examples of the "C2 to C4 alkoxycarbonyl group" represented by $R^{12}$ or $R^{13}$ include a methoxycarbonyl group, an ethoxycarbonyl group, a propoxycarbonyl group, and an isopropoxycarbonyl group.

Examples of the "C1 to C4 chain hydrocarbon group optionally substituted with at least one selected from group X" represented by $R^{14}$ include: C1 to C4 alkyl groups such as a methyl group, an ethyl group, a propyl group, an isopropyl group, a butyl group, an isobutyl group, and a sec-butyl group; and C1 to C4 alkyl groups substituted with at least one selected from group X, such as a difluoromethyl group, a trifluoromethyl group, and a 2,2,2-trifluoroethyl group.

Examples of the "C1 to C4 chain hydrocarbon group substituted with at least one halogen" represented by $R^{3a}$ or $R^{4a}$ include a trifluoromethyl group, a 1,1-difluoroethyl group, a 2,2,2-trifluoroethyl group, a pentafluoroethyl group, and a heptafluoroisopropyl group.

Examples of the "C1 to C4 chain hydrocarbon group substituted with at least one halogen" represented by $R^{14a}$ include a trifluoromethyl group, a difluoromethyl group, and a 2,2,2-trifluoroethyl group.

Examples of the present active compound include the following compounds:

a compound, wherein, in the formula (1), $R^6$ is hydrogen;

a compound, wherein, in the formula (1), $R^2$ is a halogen or hydrogen;

a compound, wherein, in the formula (1), $R^2$ is hydrogen;

a compound, wherein, in the formula (1), $R^5$ is a methyl group or hydrogen;

a compound, wherein, in the formula (1), $R^5$ is hydrogen;

a compound, wherein, in the formula (1), $R^1$ is a C3 to C6 alicyclic hydrocarbon group optionally substituted with at least one selected from group X, a phenyl group optionally substituted with at least one selected from group Y, a five-membered heterocyclic group optionally substituted with at least one selected from group Y, or a six-membered heterocyclic group optionally substituted with at least one selected from group Y;

a compound, wherein, in the formula (1), $R^1$ is a C1 to C6 chain hydrocarbon group optionally substituted with at least one selected from group X, —$OR^7$, —$S(O)_mR^7$, —$NR^7R^8$, —$NR^7C(O)R^9$, —$NR^7CO_2R^{10}$, —$C(O)R^{11}$, —$C(NOR^7)R^{11}$, —$CO_2R^{11}$, $CONR^7R^8$, —$CONR^{11}NR^{12}R^{13}$, a cyano group, a nitro group, a halogen, or hydrogen, $R^7$ and $R^8$ are the same or different, and each are a C1 to C6 chain hydrocarbon group optionally substituted with at least one selected from group X or hydrogen (wherein when m in —$S(O)_mR^7$ is 1 or 2, $R^7$ represents a C1 to C6 chain hydrocarbon group optionally substituted with at least one selected from group X), and $R^9$ is a C1 to C6 chain hydrocarbon group optionally substituted with at least one selected from group X;

a compound, wherein, in the formula (1), $R^1$ is a C1 to 06 chain hydrocarbon group optionally substituted with at least one selected from group X, —$OR^7$, —$S(O)_mR^7$, —$NR^7R^8$, —$NR^7C(O)R^9$, —$NR^7CO_2R^{10}$, —$C(O)R^{11}$, —$C(NOR^7)R^{11}$, a cyano group, a nitro group, a halogen, or hydrogen, $R^7$ and $R^8$ are the same or different, and each are a C1 to C6 chain hydrocarbon group optionally substituted with at least one selected from group X or hydrogen (wherein when m in —$S(O)_mR^7$ is 1 or 2, $R^7$ represents a C1 to C6 chain hydrocarbon group optionally substituted with at least one selected from group X), and $R^9$ is a C1 to C6 chain hydrocarbon group optionally substituted with at least one selected from group X;

a compound, wherein, in the formula (1), $R^1$ is a C1 to C6 chain hydrocarbon group optionally substituted with at least one selected from group X, $-OR^7$, $-S(O)_mR^7$, $-NR^7R^8$, a halogen, or hydrogen, $R^7$ is a C1 to C6 chain hydrocarbon group optionally substituted with at least one selected from group X, and $R^8$ is a C1 to C6 chain hydrocarbon group optionally substituted with at least one selected from group X or hydrogen;

a compound, wherein, in the formula (1), $R^1$ is a C1 to C6 chain hydrocarbon group optionally substituted with at least one selected from group X, $-OR^7$, $-S(O)_mR^7$, a halogen, or hydrogen, and $R^7$ is a C1 to C6 chain hydrocarbon group optionally substituted with at least one selected from group X;

a compound, wherein, in the formula (1), $R^1$ is $-OR^7$, $-S(O)_mR^7$, a halogen, or hydrogen, $R^7$ is a C1 to C6 chain hydrocarbon group optionally substituted with at least one selected from group X, and m is 0;

a compound, wherein, in the formula (1), either $R^3$ or $R^4$ is a C1 to C4 chain hydrocarbon group optionally substituted with at least one selected from group X, $-OR^{14}$, or $-S(O)_mR^{14}$;

a compound, wherein, in the formula (1), either $R^3$ or $R^4$ is a C1 to C4 chain hydrocarbon group optionally substituted with at least one halogen, $-OR^{14}$, or $-S(O)_mR^{14}$, and $R^{14}$ is a C1 to C4 chain hydrocarbon group optionally substituted with at least one halogen;

a compound, wherein, in the formula (1), either $R^3$ or $R^4$ is a C1 to C4 chain hydrocarbon group substituted with at least one halogen, $-OR^{14}$, or $-S(O)_mR^{14}$, and $R^{14}$ is a C1 to C4 chain hydrocarbon group substituted with at least one halogen;

a compound, wherein, in the formula (1), either $R^3$ or $R^4$ is a C1 to C4 chain hydrocarbon group substituted with at least one fluorine atom, $-OR^{14}$, or $-S(O)_mR^{14}$, and $R^{14}$ is a C1 to C4 chain hydrocarbon group substituted with at least one fluorine atom;

a compound, wherein, in the formula (1), either $R^3$ or $R^4$ is a tert-butyl group, a trifluoromethyl group, $-OR^{14}$, or $-S(O)_mR^{14}$, and $R^{14}$ is a trifluoromethyl group;

a compound, wherein, in the formula (1), either $R^3$ or $R^4$ is a trifluoromethyl group, $-OR^{14}$, or $-S(O)_mR^{14}$, and $R^{14}$ is a trifluoromethyl group;

a compound, wherein, in the formula (1), $R^3$ is a C1 to C4 chain hydrocarbon group optionally substituted with at least one selected from group X, $-OR^{14}$, or $-S(O)_mR^{14}$;

a compound, wherein, in the formula (1), $R^3$ is a C1 to C4 chain hydrocarbon group optionally substituted with at least one halogen, $-OR^{14}$, or $-S(O)_mR^{14}$, and $R^{14}$ is a C1 to C4 chain hydrocarbon group optionally substituted with at least one halogen;

a compound, wherein, in the formula (1), $R^3$ is a C1 to C4 chain hydrocarbon group substituted with at least one halogen, $-OR^{14}$, or $-S(O)_mR^{14}$, and $R^{14}$ is a C1 to C4 chain hydrocarbon group substituted with at least one halogen;

a compound, wherein, in the formula (1), $R^3$ is a C1 to C4 chain hydrocarbon group substituted with at least one halogen or $-OR^{14}$, and $R^{14}$ is a C1 to C4 chain hydrocarbon group substituted with at least one halogen;

a compound, wherein, in the formula (1), $R^4$ is a C1 to C4 chain hydrocarbon group optionally substituted with at least one selected from group X, $-OR^{14}$, or $-S(O)_mR^{14}$;

a compound, wherein, in the formula (1), $R^4$ is a C1 to C4 chain hydrocarbon group optionally substituted with at least one halogen, $-OR^{14}$, or $-S(O)_mR^{14}$, and $R^{14}$ is a C1 to C4 chain hydrocarbon group optionally substituted with at least one halogen;

a compound, wherein, in the formula (1), $R^4$ is a C1 to C4 chain hydrocarbon group substituted with at least one halogen, $-OR^{14}$, or $-S(O)_mR^{14}$, and $R^{14}$ is a C1 to C4 chain hydrocarbon group substituted with at least one halogen;

a compound, wherein, in the formula (1), $R^4$ is a C1 to C4 chain hydrocarbon group substituted with at least one halogen or $-OR^{14}$, and $R^{14}$ is a C1 to C4 chain hydrocarbon group substituted with at least one halogen;

a compound, wherein, in the formula (1), $R^3$ is a C1 to C4 chain hydrocarbon group optionally substituted with at least one selected from group X;

a compound, wherein, in the formula (1), $R^3$ is a C1 to C4 chain hydrocarbon group optionally substituted with at least one halogen;

a compound, wherein, in the formula (1), $R^3$ is a C1 to C4 chain hydrocarbon group substituted with at least one halogen;

a compound, wherein, in the formula (1), $R^3$ is a C1 to C4 chain hydrocarbon group substituted with at least one fluorine atom;

a compound, wherein, in the formula (1), $R^3$ is a tert-butyl group or a trifluoromethyl group;

a compound, wherein, in the formula (1), $R^3$ is a trifluoromethyl group;

a compound, wherein, in the formula (1), $R^3$ is a tert-butyl group;

a compound, wherein, in the formula (1), $R^4$ is a C1 to C4 chain hydrocarbon group optionally substituted with at least one selected from group X;

a compound, wherein, in the formula (1), $R^4$ is a C1 to C4 chain hydrocarbon group substituted with at least one halogen;

a compound, wherein, in the formula (1), $R^4$ is a C1 to C4 chain hydrocarbon group substituted with at least one fluorine atom;

a compound, wherein, in the formula (1), $R^4$ is a tert-butyl group or a trifluoromethyl group;

a compound, wherein, in the formula (1), $R^4$ is a trifluoromethyl group;

a compound, wherein, in the formula (1), $R^4$ is a tert-butyl group;

a compound, wherein, in the formula (1), $R^3$ is $-OR^{14}$;

a compound, wherein, in the formula (1), $R^3$ is $-OR^{14}$, and $R^{14}$ is a C1 to C4 chain hydrocarbon group optionally substituted with at least one halogen;

a compound, wherein, in the formula (1), $R^3$ is $-OR^{14}$, and $R^{14}$ is a C1 to C4 chain hydrocarbon group substituted with at least one halogen;

a compound, wherein, in the formula (1), $R^3$ is $-OR^{14}$, and $R^{14}$ is a C1 to C4 chain hydrocarbon group substituted with at least one fluorine atom;

a compound, wherein, in the formula (1), $R^3$ is $-OR^{14}$, and $R^{14}$ is a trifluoromethyl group;

a compound, wherein, in the formula (1), $R^4$ is $-OR^{14}$;

a compound, wherein, in the formula (1), $R^4$ is $-OR^{14}$, and $R^{14}$ is a C1 to C4 chain hydrocarbon group optionally substituted with at least one halogen;

a compound, wherein, in the formula (1), $R^4$ is $-OR^{14}$, and $R^{14}$ is a C1 to C4 chain hydrocarbon group substituted with at least one halogen;

a compound, wherein, in the formula (1), $R^4$ is —$OR^{14}$, and $R^{14}$ is a C1 to C4 chain hydrocarbon group substituted with at least one fluorine atom;

a compound, wherein, in the formula (1), $R^4$ is —$OR^{14}$, and $R^{14}$ is a trifluoromethyl group;

a compound, wherein, in the formula (1), $R^3$ is a C1 to C4 chain hydrocarbon group optionally substituted with at least one selected from group X, and $R^4$ is hydrogen;

a compound, wherein, in the formula (1), $R^3$ is a C1 to C4 chain hydrocarbon group optionally substituted with at least one halogen, and $R^4$ is hydrogen;

a compound, wherein, in the formula (1), $R^3$ is a C1 to C4 chain hydrocarbon group substituted with at least one halogen, and $R^4$ is hydrogen;

a compound, wherein, in the formula (1), $R^3$ is a C1 to C4 chain hydrocarbon group substituted with at least one fluorine atom, and $R^4$ is hydrogen;

a compound, wherein, in the formula (1), $R^3$ is —$OR^{14}$, $R^{14}$ is a C1 to C4 chain hydrocarbon group optionally substituted with at least one halogen, and $R^4$ is hydrogen;

a compound, wherein, in the formula (1), $R^3$ is —$OR^{14}$, $R^{14}$ is a C1 to C4 chain hydrocarbon group substituted with at least one halogen, and $R^4$ is hydrogen;

a compound, wherein, in the formula (1), $R^3$ is hydrogen, and $R^4$ is a C1 to C4 chain hydrocarbon group optionally substituted with at least one selected from group X;

a compound, wherein, in the formula (1), $R^3$ is hydrogen, and $R^4$ is a C1 to C4 chain hydrocarbon group optionally substituted with at least one halogen;

a compound, wherein, in the formula (1), $R^3$ is hydrogen, and $R^4$ is a C1 to C4 chain hydrocarbon group substituted with at least one halogen;

a compound, wherein, in the formula (1), $R^3$ is hydrogen, and $R^4$ is a C1 to C4 chain hydrocarbon group substituted with at least one fluorine atom;

a compound, wherein, in the formula (1), $R^3$ is hydrogen, $R^4$ is —$OR^{14}$, and $R^{14}$ is a C1 to C4 chain hydrocarbon group optionally substituted with at least one halogen;

a compound, wherein, in the formula (1), $R^3$ is hydrogen, $R^4$ is —$OR^{14}$, and $R^{14}$ is a C1 to C4 chain hydrocarbon group substituted with at least one halogen;

a compound, wherein, in the formula (1), $R^3$ is a tert-butyl group or a trifluoromethyl group, and $R^4$ is hydrogen;

a compound, wherein, in the formula (1), $R^3$ is a tert-butyl group, and $R^4$ is hydrogen;

a compound, wherein, in the formula (1), $R^3$ is a trifluoromethyl group, and $R^4$ is hydrogen;

a compound, wherein, in the formula (1), $R^3$ is —$OR^{14}$, $R^{14}$ is a trifluoromethyl group, and $R^4$ is hydrogen;

a compound, wherein, in the formula (1), $R^3$ is hydrogen, and $R^4$ is a tert-butyl group or a trifluoromethyl group;

a compound, wherein, in the formula (1), $R^3$ is hydrogen, and $R^4$ is a tert-butyl group;

a compound, wherein, in the formula (1), $R^3$ is hydrogen, and $R^4$ is a trifluoromethyl group;

a compound, wherein, in the formula (1), $R^3$ is hydrogen, $R^4$ is —$OR^{14}$, and $R^{14}$ is a trifluoromethyl group;

a compound, wherein, in the formula (1), $A^1$ is =C($R^6$)—, and $A^2$ is nitrogen or =C($R^6$)—;

a compound, wherein, in the formula (1), $A^1$ is =C($R^6$)—, $A^2$ is nitrogen or =C($R^6$)—, and $R^6$ is hydrogen;

a compound, wherein, in the formula (1), $A^1$ is nitrogen, $A^2$ is =C($R^6$)—, and $R^6$ is hydrogen;

a compound, wherein, in the formula (1), $A^1$ is =C($R^6$)—, $A^2$ is nitrogen, and $R^6$ is hydrogen;

a compound, wherein, in the formula (1), $A^1$ and $A^2$ are =C($R^6$)—, and $R^6$ is hydrogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_mR^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), a halogen, or hydrogen, $R^2$ is a halogen or hydrogen, $R^5$ is a methyl group or hydrogen, and $R^9$ is a C1 to C4 alkyl group optionally substituted with at least one halogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_mR^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —NHC(O)$R^9$, a halogen, or hydrogen, $R^2$ is a halogen or hydrogen, $R^5$ is a methyl group or hydrogen, $R^6$ is hydrogen, and $R^9$ is a C1 to C4 alkyl group optionally substituted with at least one halogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_mR^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —NHC(O)$R^9$, a halogen, or hydrogen, $R^2$ is hydrogen, $R^5$ is a methyl group or hydrogen, $R^6$ is hydrogen, and $R^9$ is a C1 to C4 alkyl group optionally substituted with at least one halogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —$NHC(O)R^9$, a halogen, or hydrogen, $R^2$ is hydrogen, $R^5$ is hydrogen, $R^6$ is hydrogen, and $R^9$ is a C1 to C4 alkyl group optionally substituted with at least one halogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_m R^{7b}$ ($R^{7b}$ represents a C1 to C4 alkyl group optionally substituted $R^{8a}$ with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —$NHC(O)R^9$, a halogen, or hydrogen, $R^2$ is hydrogen, $R^3$ is a C1 to C4 chain hydrocarbon group optionally substituted with at least one halogen or —$OR^{14}$, $R^4$ is hydrogen, $R^5$ is hydrogen, $R^6$ is hydrogen, $R^9$ is a C1 to C4 alkyl group optionally substituted with at least one halogen, and $R^{14}$ is a C1 to C4 chain hydrocarbon group optionally substituted with at least one halogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —$NHC(O)R^9$, a halogen, or hydrogen, $R^2$ is hydrogen, $R^3$ is a C1 to C4 chain hydrocarbon group substituted with at least one halogen or —$OR^{14}$, $R^4$ is hydrogen, $R^5$ is hydrogen, $R^6$ is hydrogen, $R^9$ is a C1 to C4 alkyl group optionally substituted with at least one halogen, and $R^{14}$ is a C1 to C4 chain hydrocarbon group substituted with at least one halogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —$NHC(O)R^9$, a halogen, or hydrogen, $R^2$ is hydrogen, $R^3$ is a tert-butyl group, a trifluoromethyl group, or —$OR^{14}$, $R^4$ is hydrogen, $R^5$ is hydrogen, $R^6$ is hydrogen, $R^9$ is a C1 to C4 alkyl group optionally substituted with at least one halogen, and $R^{14}$ is a trifluoromethyl group;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_m R^{7b}$ ($R^{7b}$ represents a C1 to C4 alkyl group optionally substituted with at least one halogen, and m represents 0, 1, or 2), —$NR^{7c}R^{8a}$ ($R^{7C}$ and $R^{8a}$ are the same or different, and each represent a C1 to C4 alkyl group optionally substituted with at least one halogen or hydrogen), —$NHC(O)R^9$, a halogen, or hydrogen, $R^2$ is hydrogen, $R^3$ is a C1 to C4 chain hydrocarbon group substituted with at least one halogen, $R^4$ is hydrogen, $R^5$ is hydrogen, $R^6$ is hydrogen, and $R^9$ is a C1 to C4 alkyl group optionally substituted with at least one halogen;

a compound, wherein, in the formula (1), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —$S(O)_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —$NHC(O)R^9$, a halogen, or hydrogen, $R^2$ is hydrogen,
$R^3$ is a trifluoromethyl group,
$R^4$ is hydrogen,
$R^5$ is hydrogen,
$R^6$ is hydrogen, and
$R^9$ is a C1 to C4 alkyl group optionally substituted with at least one halogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m$—$R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, and
$R^2$ is a halogen or hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}R^{7b}$ and $R^{8a}$ are the same or different, and each represent a C1 to C4 alkyl group optionally substituted with at least one halogen or hydrogen), a halogen, or hydrogen,
$R^2$ is hydrogen, and
$R^6$ is hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen,
$R^2$ is hydrogen,
$R^5$ is a methyl group or hydrogen, and
$R^6$ is hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen,
$R^2$ is hydrogen,
$R^5$ is hydrogen, and
$R^6$ is hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen,
$R^2$ is hydrogen,
$R^3$ is a C1 to C4 chain hydrocarbon group optionally substituted with at least one halogen or —$OR^{14}$,
$R^4$ is hydrogen,
$R^5$ is hydrogen,
$R^6$ is hydrogen, and
$R^{14}$ is a C1 to C4 chain hydrocarbon group optionally substituted with at least one halogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{7b}R^{8a}$ ($R^{7b}$ and $R^{8a}$ are the same or different, and each represent a C1 to C4 alkyl group optionally substituted with at least one halogen or hydrogen), a halogen, or hydrogen,
$R^2$ is hydrogen,
$R^3$ is a C1 to C4 chain hydrocarbon group substituted with at least one halogen or —$OR^{14}$,
$R^4$ is hydrogen,
$R^5$ is hydrogen,
$R^6$ is hydrogen, and
$R^{14}$ is a C1 to C4 chain hydrocarbon group substituted with at least one halogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen,
$R^2$ is hydrogen,
$R^3$ is a C1 to C4 chain hydrocarbon group substituted with at least one halogen,
$R^4$ is hydrogen,
$R^5$ is hydrogen, and
$R^6$ is hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen,
$R^2$ is hydrogen,
$R^3$ is hydrogen,
$R^4$ is a C1 to C4 chain hydrocarbon group optionally substituted with at least one halogen, or —$OR^{14}$,
$R^5$ is hydrogen,
$R^6$ is hydrogen, and $R^{14}$ is a C1 to C4 chain hydrocarbon group optionally substituted with at least one halogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, $R^2$ is hydrogen,
$R^3$ is hydrogen,
$R^4$ is a C1 to C4 chain hydrocarbon group substituted with at least one halogen, or —$OR^{14}$,
$R^5$ is hydrogen,
$R^6$ is hydrogen, and
$R^{14}$ is a C1 to C4 chain hydrocarbon group substituted with at least one halogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, $R^2$ is hydrogen,
$R^3$ is hydrogen,
$R^4$ is a C1 to C4 chain hydrocarbon group substituted with at least one halogen,
$R^5$ is hydrogen, and
$R^6$ is hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, $R^2$ is hydrogen,
$R^3$ is a C1 to C4 chain hydrocarbon group substituted with at least one fluorine atom,
$R^4$ is hydrogen,
$R^5$ is hydrogen, and
$R^6$ is hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, $R^2$ is hydrogen,
$R^3$ is a tert-butyl group or a trifluoromethyl group,
$R^4$ is hydrogen,
$R^5$ is hydrogen, and
$R^6$ is hydrogen;

a compound, wherein, in the formula (1), $R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, $R^2$ is hydrogen,
$R^3$ is a trifluoromethyl group,
$R^4$ is hydrogen,
$R^5$ is hydrogen, and
$R^6$ is hydrogen;

a compound, wherein, in the formula (1), $A^1$ is =$C(R^6)$—, $A^2$ is nitrogen or =$C(R^6)$—,
$R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, $R^2$ is hydrogen,
$R^3$ is a tert-butyl group or a trifluoromethyl group,
$R^4$ is hydrogen,
$R^5$ is hydrogen, and
$R^6$ is hydrogen;

a compound, wherein, in the formula (1), $A^1$ is =$C(R^6)$—, $A^2$ is nitrogen or =$C(R^6)$—,
$R^1$ is a C1 to C4 alkyl group optionally substituted with at least one halogen, —$OR^{7a}$ ($R^{7a}$ represents a C1 to C4 alkyl group optionally substituted with at least one halogen), —$S(O)_m R^{7a}$ (m represents 0, 1, or 2), —$NR^{7b}R^{8a}$ ($R^{7b}$ and $R^{8a}$ are the same or different, and each represent a C1 to C4 alkyl group optionally substituted with at least one halogen or hydrogen), a halogen, or hydrogen, $R^2$ is hydrogen,
$R^3$ is a trifluoromethyl group,
$R^4$ is hydrogen,
$R^5$ is hydrogen, and
$R^6$ is hydrogen;

a compound, wherein, in the formula (1), $R^1$ is a C1 to C4 alkyl group optionally substituted with at least one halogen, —$OR^7$, —$S(O)_m R^7$ (m represents 0, 1, or 2), a halogen, or hydrogen, $R^2$ is hydrogen,
$R^3$ is a tert-butyl group or a trifluoromethyl group,
$R^4$ is hydrogen,
$R^5$ is hydrogen,
$R^6$ is hydrogen, and
$R^7$ is a C1 to C4 alkyl group optionally substituted with at least one halogen;

a compound, wherein, in the formula (1), $R^1$ is a C1 to C4 alkyl group optionally substituted with at least one halogen, —$OR^7$, —$S(O)_m R^7$ (m represents 0, 1, or 2), a halogen, or hydrogen, $R^2$ is hydrogen,
$R^3$ is a trifluoromethyl group,
$R^4$ is hydrogen,
$R^5$ is hydrogen,
$R^6$ is hydrogen, and
$R^7$ is a C1 to C4 alkyl group optionally substituted with at least one halogen;

a compound, wherein, in the formula (1), $A^1$ is =$C(R^6)$—, $A^2$ is nitrogen or =$C(R^6)$—,
$R^1$ is a C1 to C4 alkyl group optionally substituted with at least one halogen, —$OR^7$, —$S(O)_m R^7$ (m represents 0, 1, or 2), a halogen, or hydrogen, $R^2$ is hydrogen,
$R^3$ is a trifluoromethyl group,
$R^4$ is hydrogen,
$R^5$ is hydrogen,
$R^6$ is hydrogen, and
$R^7$ is a C1 to C4 alkyl group optionally substituted with at least one halogen; and a compound, wherein, in the formula (1), $A^1$ is $=C(R^6)-$, $A^2$ is nitrogen or $=C(R^6)-$, $R^1$ is $-OR^7$, $-S(O)_mR^7$ (m represents 0, 1, or 2), a halogen, or hydrogen, $R^2$ is hydrogen, $R^3$ is a trifluoromethyl group, $R^4$ is hydrogen, $R^5$ is hydrogen, $R^6$ is hydrogen, and $R^7$ is a C1 to C4 alkyl group optionally substituted with at least one halogen.

Examples of the heterocyclic compound represented by the formula (2) include the following compounds:

a compound, wherein, in the formula (2), $R^6$ is hydrogen;

a compound, wherein, in the formula (2), $R^2$ is a halogen or hydrogen;

a compound, wherein, in the formula (2), $R^2$ is hydrogen;

a compound, wherein, in the formula (2), $R^5$ is a methyl group or hydrogen;

a compound, wherein, in the formula (2), $R^5$ is hydrogen;

a compound, wherein, in the formula (2), $R^1$ is a C3 to C6 alicyclic hydrocarbon group optionally substituted with at least one selected from group X, a phenyl group optionally substituted with at least one selected from group Y, a five-membered heterocyclic group optionally substituted with at least one selected from group Y, and a six-membered heterocyclic group optionally substituted with at least one selected from group Y;

a compound, wherein, in the formula (2), $R^1$ is a C1 to C6 chain hydrocarbon group optionally substituted with at least one selected from group X, $-OR^7$, $-S(O)_mR^7$, $-NR^7R^8$, $-NR^7C(O)R^9$, $-NR^7CO_2R^{10}$, $-C(O)R^{11}$, $-C(NOR^7)R^{11}$, $-CO_2R^{11}$, $-CONR^7R^8$, $-CONR^{11}NR^{12}R^{13}$, a cyano group, a nitro group, or a halogen, $R^7$ and $R^8$ are the same or different, and each are a C1 to C6 chain hydrocarbon group optionally substituted with at least one selected from group X or hydrogen (wherein when m in $-S(O)_mR^7$ is 1 or 2, $R^7$ represents a C1 to C6 chain hydrocarbon group optionally substituted with at least one selected from group X), and $R^9$ is a C1 to C6 chain hydrocarbon group optionally substituted with at least one selected from group X;

a compound, wherein, in the formula (2), $R^1$ is a C1 to C6 chain hydrocarbon group optionally substituted with at least one selected from group X, $-OR^7$, $-S(O)_mR^7$, $-NR^7R^8$, $-NR^7C(O)R^9$, $-NR^7CO_2R^{10}$, $-C(O)R^{11}$, $-C(NOR^7)R^{11}$, a cyano group, a nitro group, or a halogen, $R^7$ and $R^8$ are the same or different, and each are a C1 to C6 chain hydrocarbon group optionally substituted with at least one selected from group X or hydrogen (wherein when m in $-S(O)_mR^7$ is 1 or 2, $R^7$ represents a C1 to C6 chain hydrocarbon group optionally substituted with at least one selected from group X), and $R^9$ is a C1 to C6 chain hydrocarbon group optionally substituted with at least one selected from group X;

a compound, wherein, in the formula (2), $R^1$ is a C1 to C6 chain hydrocarbon group optionally substituted with at least one selected from group X, $-OR^7$, $-S(O)_mR^7$, $-NR^7R^8$, or a halogen, $R^7$ is a C1 to C6 chain hydrocarbon group, optionally substituted with at least one selected from group X, and $R^8$ is a C1 to C6 chain hydrocarbon group optionally substituted with at least one selected from group X or hydrogen;

a compound, wherein, in the formula (2), $R^1$ is a C1 to C6 chain hydrocarbon group optionally substituted with at least one selected from group X, $-OR^7$, $-S(O)_mR^7$, or a halogen, and $R^7$ is a C1 to C6 chain hydrocarbon group optionally substituted with at least one selected from group X;

a compound, wherein, in the formula (2), $R^1$ is $-OR^7$, $-S(O)_mR^7$, or a halogen, $R^7$ is a C1 to C6 chain hydrocarbon group optionally substituted with at least one selected from group X, and m is 0;

a compound, wherein, in the formula (2), either $R^{3a}$ or $R^{4a}$ is a C1 to C4 chain hydrocarbon group substituted with at least one halogen, $-OR^{14a}$, or $-S(O)_mR^{14a}$;

a compound, wherein, in the formula (2), either $R^{3a}$ or $R^{4a}$ is a C1 to C4 chain hydrocarbon group substituted with at least one fluorine atom, $-OR^{14a}$, or $-S(O)_mR^{14a}$, and $R^{14a}$ is a C1 to C4 chain hydrocarbon group substituted with at least one fluorine atom;

a compound, wherein, in the formula (2), either $R^{3a}$ or $R^{4a}$ is a trifluoromethyl group, $-OR^{14a}$, or $-S(O)_mR^{14a}$, and $R^{14a}$ is a trifluoromethyl group;

a compound, wherein, in the formula (2), $R^{3a}$ is a C1 to C4 chain hydrocarbon group substituted with at least one halogen, $-OR^{14a}$, or $-S(O)_mR^{14a}$;

a compound, wherein, in the formula (2), $R^{3a}$ is a C1 to C4 chain hydrocarbon group substituted with at least one halogen or $-OR^{14a}$;

a compound, wherein, in the formula (2), $R^{4a}$ is a C1 to C4 chain hydrocarbon group substituted with at least one halogen, $-OR^{14a}$ or $-S(O)_mR^{14a}$;

a compound, wherein, in the formula (2), $R^{4a}$ is a C1 to C4 chain hydrocarbon group substituted with at least one halogen or $-OR^{14a}$, and $R^{14a}$ is a C1 to C4 chain hydrocarbon group substituted with at least one halogen;

a compound, wherein, in the formula (2), $R^{4a}$ is a C1 to C4 chain hydrocarbon group substituted with at least one halogen;

a compound, wherein, in the formula (2), $R^{3a}$ is a C1 to C4 chain hydrocarbon group substituted with at least one fluorine atom;

a compound, wherein, in the formula (2), $R^{3a}$ is a trifluoromethyl group;

a compound, wherein, in the formula (2), $R^{4a}$ is a C1 to C4 chain hydrocarbon group substituted with at least one halogen;

a compound, wherein, in the formula (2), $R^{4a}$ is a C1 to C4 chain hydrocarbon group substituted with at least one fluorine atom;

a compound, wherein, in the formula (2), $R^{4a}$ is a trifluoromethyl group;

a compound, wherein, in the formula (2), $R^{3a}$ is a C1 to C4 chain hydrocarbon group substituted with at least one halogen, and $R^{4a}$ is hydrogen;

a compound, wherein, in the formula (2), $R^a$ is a C1 to C4 chain hydrocarbon group substituted with at least one fluorine atom, and $R^{4a}$ is hydrogen;

a compound, wherein, in the formula (2), $R^a$ is $-OR^{14a}$, and $R^{4a}$ is hydrogen;

a compound, wherein, in the formula (2), $R^{3a}$ is hydrogen, and $R^{4a}$ is a C1 to C4 chain hydrocarbon group substituted with at least one halogen;

a compound, wherein, in the formula (2), $R^{3a}$ is hydrogen, and $R^{4a}$ is a C1 to C4 chain hydrocarbon group substituted with at least one fluorine atom;

a compound, wherein, in the formula (2), $R^{3a}$ is hydrogen, and $R^{4a}$ is $-OR^{14a}$.

a compound, wherein, in the formula (2), $R^{3a}$ is a trifluoromethyl group, and $R^{4a}$ is hydrogen;

a compound, wherein, in the formula (2), $R^{3a}$ is $-OR^{14a}$, $R^{4a}$ is hydrogen, and $R^{14a}$ is a trifluoromethyl group;

a compound, wherein, in the formula (2), $R^{3a}$ is hydrogen, and $R^{4a}$ is a trifluoromethyl group;

a compound, wherein, in the formula (2), $R^{3a}$ is hydrogen, $R^{4a}$ is —$OR^{14a}$, and $R^{14a}$ is a trifluoromethyl group;

a compound, wherein, in the formula (2), $A^1$ is =C($R^6$)—, and $A^2$ is nitrogen or =C($R^6$)—;

a compound, wherein, in the formula (2), $A^1$ is =C($R^6$)—, $A^2$ is nitrogen or =C($R^6$)—, and $R^6$ is hydrogen;

a compound, wherein, in the formula (2), $A^1$ is nitrogen, $A^2$ is =C($R^6$)—, and $R^6$ is hydrogen;

a compound, wherein, in the formula (2), $A^1$ is =C($R^6$)—, $A^2$ is nitrogen, and $R^6$ is hydrogen;

a compound, wherein, in the formula (2), $A^1$ and $A^2$ are =C($R^6$)—, and $R^6$ is hydrogen;

a compound, wherein, in the formula (2), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —NHC(O)$R^9$, or a halogen, $R^2$ is a halogen or hydrogen, $R^5$ is a methyl group or hydrogen, and $R^9$ is a C1 to C4 alkyl group optionally substituted with at least one halogen;

a compound, wherein, in the formula (2), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —NHC(O)$R^9$, or a halogen, $R^2$ is a halogen or hydrogen, $R^5$ is a methyl group or hydrogen, $R^6$ is hydrogen, and $R^9$ is a C1 to C4 alkyl group optionally substituted with at least one halogen;

a compound, wherein, in the formula (2), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —NHC(O)$R^9$, or a halogen, $R^2$ is hydrogen, $R^5$ is a methyl group or hydrogen, $R^6$ is hydrogen, and $R^9$ is a C1 to C4 alkyl group optionally substituted with at least one halogen;

a compound, wherein, in the formula (2), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —NHC(O)$R^9$, or a halogen, $R^2$ is hydrogen, $R^5$ is hydrogen, $R^6$ is hydrogen, and $R^9$ is a C1 to C4 alkyl group optionally substituted with at least one halogen;

a compound, wherein, in the formula (2), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —$OR^{7a}$ ($R^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m R^{7b}$ ($R^{7b}$ represents a C1 to C4 alkyl group optionally substituted with at least one halogen, and m represents 0, 1, or 2), —$NR^{7c}R^{8a}$ ($R^{7c}$ and $R^{8a}$ are the same or different, and each represent a C1 to C4 alkyl group optionally substituted with at least one halogen or hydrogen), —NHC(O)$R^9$, or a halogen, $R^2$ is hydrogen, $R^{3a}$ is a C1 to C4 chain hydrocarbon group substituted with at least one halogen or —$OR^{14a}$, $R^{4a}$ is hydrogen, $R^5$ is hydrogen, $R^6$ is hydrogen, and $R^9$ is a C1 to C4 alkyl group optionally substituted with at least one halogen;

a compound, wherein, in the formula (2), $R^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —OR$^{7a}$ (R$^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m$R$^{7b}$ (R$^{7b}$ represents a C1 to C4 alkyl group optionally substituted with at least one halogen, and m represents 0, 1, or 2), —NR$^{7c}$R$^{8a}$ (R$^{7c}$ and R$^{8a}$ are the same or different, and each represent a C1 to C4 alkyl group optionally substituted with at least one halogen or hydrogen), —NHC(O)R$^9$, or a halogen, R$^2$ is hydrogen,
R$^{3a}$ is a trifluoromethyl group or —OR$^{14a}$, and R$^{14a}$ is a trifluoromethyl group,
R$^{4a}$ is hydrogen,
R$^5$ is hydrogen,
R$^6$ is hydrogen, and
R$^9$ is a C1 to C4 alkyl group optionally substituted with at least one halogen;

a compound, wherein, in the formula (2), R$^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —OR$^{7a}$ (R$^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m$R$^{7b}$ (R$^{7b}$ represents a C1 to C4 alkyl group optionally substituted with at least one halogen, and m represents 0, 1, or 2), —NR$^{7c}$R$^{8a}$ (R$^{7c}$ and R$^{8a}$ are the same or different, and each represent a C1 to C4 alkyl group optionally substituted with at least one halogen or hydrogen), —NHC(O)R$^9$, or a halogen, R$^2$ is hydrogen,
R$^{3a}$ is a C1 to C4 chain hydrocarbon group substituted with at least one halogen,
R$^{4a}$ is hydrogen,
R$^5$ is hydrogen,
R$^6$ is hydrogen, and
R$^9$ is a C1 to C4 alkyl group optionally substituted with at least one halogen;

a compound, wherein, in the formula (2), R$^1$ is a C1 to C4 alkyl group optionally substituted with at least one halogen, a C2 to C4 alkenyl group, a pyrrolidyl group, a piperidyl group, a morpholino group, an imidazolyl group, a pyrazolyl group, a triazolyl group, a pyrazolyl group substituted with at least one C1 to C3 alkyl group, a pyrazolyl group substituted with at least one (C1 to C3 alkyl group substituted with at least one halogen), a phenyl group, a pyridyl group, —OR$^{7a}$ (R$^{7a}$ represents a C1 to C4 alkyl group optionally substituted with at least one halogen, a C3 to C4 alkenyl group optionally substituted with at least one halogen, a C3 to C4 alkynyl group, a benzyl group, or a C4 to C7 cycloalkylmethyl group), —S(O)$_m$R$^{7b}$ (R$^{7b}$ represents a C1 to C4 alkyl group optionally substituted with at least one halogen, and m represents 0, 1, or 2), —NR$^{7c}$R$^{8a}$ (R$^{7c}$ and R$^{8a}$ are the same or different, and each represent a C1 to C4 alkyl group optionally substituted with at least one halogen or hydrogen), —NHC(O)R$^9$, or a halogen, R$^2$ is hydrogen,
R$^{3a}$ is a trifluoromethyl group,
R$^{4a}$ is hydrogen,
R$^5$ is hydrogen,
R$^6$ is hydrogen, and
R$^9$ is a C1 to C4 alkyl group optionally substituted with at least one halogen;

a compound, wherein, in the formula (2), R$^1$ is a C1 to C4 alkyl group optionally substituted with at least one halogen, —OR$^{7a}$ (R$^{7a}$ represents a C1 to C4 alkyl group optionally substituted with at least one halogen), —S(O)$_m$R$^{7a}$ (m represents 0, 1, or 2), —NR$^{7b}$R$^{8a}$ (R$^{7b}$ and R$^{8a}$ are the same or different, and each represent a C1 to C4 alkyl group optionally substituted with at least one halogen or hydrogen), or a halogen;

a compound, wherein, in the formula (2), R$^1$ is a C1 to C4 alkyl group optionally substituted with at least one halogen, —OR$^{7a}$ (R$^{7a}$ represents a C1 to C4 alkyl group optionally substituted with at least one halogen), —S(O)$_m$R$^{7a}$ (m represents 0, 1, or 2), —NR$^{7b}$R$^{8a}$ (R$^{7b}$ and R$^{8a}$ are the same or different, and each represent a C1 to C4 alkyl group optionally substituted with at least one halogen or hydrogen), or a halogen and,
R$^2$ is a halogen or hydrogen;

a compound, wherein, in the formula (2), R$^1$ is a C1 to C4 alkyl group optionally substituted with at least one halogen, —OR$^{7a}$ (R$^{7a}$ represents a C1 to C4 alkyl group optionally substituted with at least one halogen), —S(O)$_m$R$^{7a}$ (m represents 0, 1, or 2), —NR$^{7b}$R$^{8a}$ (R$^{7b}$ and R$^{8a}$ are the same or different, and each represent a C1 to C4 alkyl group optionally substituted with at least one halogen or hydrogen), or a halogen,
R$^2$ is hydrogen, and
R$^6$ is hydrogen;

a compound, wherein, in the formula (2), R$^1$ is a C1 to C4 alkyl group optionally substituted with at least one halogen, —OR$^{7a}$ (R$^{7a}$ represents a C1 to C4 alkyl group optionally substituted with at least one halogen), —S(O)$_m$R$^{7a}$ (m represents 0, 1, or 2), —NR$^{7b}$R$^{8a}$ (R$^{7b}$ and R$^{8a}$ are the same or different, and each represent a C1 to C4 alkyl group optionally substituted with at least one halogen or hydrogen), or a halogen,
R$^2$ is hydrogen,
R$^5$ is a methyl group or hydrogen, and
R$^6$ is hydrogen;

a compound, wherein, in the formula (2), R$^1$ is a C1 to C4 alkyl group optionally substituted with at least one halogen, —OR$^{7a}$ (R$^{7a}$ represents a C1 to C4 alkyl group optionally substituted with at least one halogen), —S(O)$_m$R$^{7a}$ (m represents 0, 1, or 2), —NR$^{7b}$R$^{8a}$ (R$^{7b}$ and R$^{8a}$ are the same or different, and each represent a C1 to C4 alkyl group optionally substituted with at least one halogen or hydrogen), or a halogen,
R$^2$ is hydrogen,
R$^5$ is hydrogen, and
R$^6$ is hydrogen;

a compound, wherein, in the formula (2), R$^1$ is a C1 to C4 alkyl group optionally substituted with at least one halogen, —OR$^{7a}$ (R$^{7a}$ represents a C1 to C4 alkyl group optionally substituted with at least one halogen), —S(O)$_m$R$^{7a}$ (m represents 0, 1, or 2), —NR$^{7b}$R$^{8a}$ (R$^{7b}$ and R$^{8a}$ are the same or different, and each represent a C1 to C4 alkyl group optionally substituted with at least one halogen or hydrogen), or a halogen,
R$^2$ is hydrogen,
R$^{3a}$ is a C1 to C4 chain hydrocarbon group substituted with at least one halogen or —OR$^{14a}$, $R^{4a}$ is hydrogen,
$R^5$ is hydrogen, and
$R^6$ is hydrogen;
a compound, wherein, in the formula (2), $R^1$ is a C1 to C4 alkyl group optionally substituted with at least one halogen, $-OR^{7a}$ ($R^{7a}$ represents a C1 to C4 alkyl group optionally substituted with at least one halogen), $-S(O)_mR^{7a}$ (m represents 0, 1, or 2), $-NR^{7b}R^{8a}$ ($R^{7b}$ and $R^{8a}$ are the same or different, and each represent a C1 to C4 alkyl group optionally substituted with at least one halogen or hydrogen, or a halogen,
$R^2$ is hydrogen,
$R^{3a}$ is a C1 to C4 chain hydrocarbon group substituted with at least one halogen,
$R^{4a}$ is hydrogen,
$R^5$ is hydrogen, and
$R^6$ is hydrogen;
a compound, wherein, in the formula (2), $R^1$ is a C1 to C4 alkyl group optionally substituted with at least one halogen, $-OR^{7a}$ ($R^{7a}$ represents a C1 to C4 alkyl group optionally substituted with at least one halogen), $-S(O)_mR^{7a}$ (m represents 0, 1, or 2), $-NR^{7b}R^{8a}$ ($R^{7b}$ and $R^{8a}$ are the same or different, and each represent a C1 to C4 alkyl group optionally substituted with at least one halogen or hydrogen), or a halogen,
$R^2$ is hydrogen,
$R^{3a}$ is hydrogen,
$R^{4a}$ is a C1 to C4 chain hydrocarbon group substituted with at least one halogen or $-OR^{14a}$,
$R^5$ is hydrogen, and
$R^6$ is hydrogen;
a compound, wherein, in the formula (2), $R^1$ is a C1 to C4 alkyl group optionally substituted with at least one halogen, $-OR^{7a}$ ($R^{7a}$ represents a C1 to C4 alkyl group optionally substituted with at least one halogen), $-S(O)_mR^{7a}$ (m represents 0, 1, or 2), $-NR^{7b}R^{8a}$ ($R^{7b}$ and $R^{8a}$ are the same or different, and each represent a C1 to C4 alkyl group optionally substituted with at least one halogen or hydrogen), or a halogen,
$R^2$ is hydrogen,
$R^{3a}$ is hydrogen,
$R^{4a}$ is a C1 to C4 chain hydrocarbon group substituted with at least one halogen,
$R^5$ is hydrogen, and
$R^6$ is hydrogen;
a compound, wherein, in the formula (2), $R^1$ is a C1 to C4 alkyl group optionally substituted with at least one halogen, $-OR^{7a}$ ($R^{7a}$ represents a C1 to C4 alkyl group optionally substituted with at least one halogen), $-S(O)_mR^{7a}$ (m represents 0, 1, or 2), $-NR^{7b}R^{8a}R^{7b}$ and $R^{8a}$ are the same or different, and each represent a C1 to C4 alkyl group optionally substituted with at least one halogen or hydrogen), or a halogen,
$R^2$ is hydrogen,
$R^{3a}$ is a C1 to C4 chain hydrocarbon group substituted with at least one fluorine atom,
$R^{4a}$ is hydrogen,
$R^5$ is hydrogen, and
$R^6$ is hydrogen;
a compound, wherein, in the formula (2), $R^1$ is a C1 to C4 alkyl group optionally substituted with at least one halogen, $-OR^{7a}$ ($R^{7a}$ represents a C1 to C4 alkyl group optionally substituted with at least one halogen), $-S(O)_mR^{7a}$ (m represents 0, 1, or 2), $-NR^{7b}R^{8a}$ ($R^{7b}$ and $R^{8a}$ are the same or different, and each represent a C1 to C4 alkyl group optionally substituted with at least one halogen or hydrogen), or a halogen, $R^2$ is hydrogen,
$R^{3a}$ is a trifluoromethyl group,
$R^{4a}$ is hydrogen,
$R^5$ is hydrogen, and
$R^6$ is hydrogen;
a compound, wherein, in the formula (2),
$A^1$ is $=C(R^6)-$, $A^2$ is nitrogen or $=C(R^6)-$,
$R^1$ is a C1 to C4 alkyl group optionally substituted with at least one halogen, $-OR^{7a}$ ($R^{7a}$ represents a C1 to C4 alkyl group optionally substituted with at least one halogen), $-S(O)_mR^{7a}$ (m represents 0, 1, or 2), $-NR^{7b}R^{8a}$ ($R^{7b}$ and $R^{8a}$ are the same or different, and each represent a C1 to C4 alkyl group optionally substituted with at least one halogen or hydrogen), or a halogen,
$R^2$ is hydrogen,
$R^{3a}$ is a trifluoromethyl group,
$R^{4a}$ is hydrogen,
$R^5$ is hydrogen, and
$R^6$ is hydrogen;
a compound, wherein, in the formula (2), $R^1$ is a C1 to C4 alkyl group optionally substituted with at least one halogen, $-OR^7$, $-S(O)_mR^7$ (m represents 0, 1, or 2), or a halogen,
$R^2$ is hydrogen,
$R^{3a}$ is a trifluoromethyl group,
$R^{4a}$ is hydrogen,
$R^5$ is hydrogen,
$R^6$ is hydrogen, and
$R^7$ is a C1 to C4 alkyl group optionally substituted with at least one halogen;
a compound, wherein, in the formula (2),
$A^1$ is $=C(R^6)-$, $A^2$ is nitrogen or $=C(R^6)-$,
$R^1$ is a C1 to C4 alkyl group optionally substituted with at least one halogen, $-OR^7$, $-S(O)_mR^7$ (m represents 0, 1, or 2), or a halogen,
$R^2$ is hydrogen,
$R^{3a}$ is a trifluoromethyl group,
$R^{4a}$ is hydrogen,
$R^5$ is hydrogen,
$R^6$ is hydrogen, and
$R^7$ is a C1 to C4 alkyl group optionally substituted with at least one halogen; and
a compound, wherein, in the formula (2),
$A^1$ is $=C(R^6)-$, $A^2$ is nitrogen or $=C(R^6)-$,
$R^1$ is $-OR^7$, $-S(O)_mR^7$ (m represents 0, 1, or 2), or a halogen,
$R^2$ is hydrogen,
$R^{3a}$ is a trifluoromethyl group,
$R^{4a}$ is hydrogen,
$R^5$ is hydrogen,
$R^6$ is hydrogen, and
$R^7$ is a C1 to C4 alkyl group optionally substituted with at least one halogen.

Next, a method for producing the present active compound will be described.

The present active compound can be produced, for example, by the following (Production Method 1) to (Production Method 5).

(Production Method 1)

A compound (5-a), that is a compound, wherein, in the formula (1), n is 0 and $A^2$ is $=C(R^6)-$, can be produced by reacting a compound (3) with a compound (4) or a hydrochloride thereof in the presence of a base:

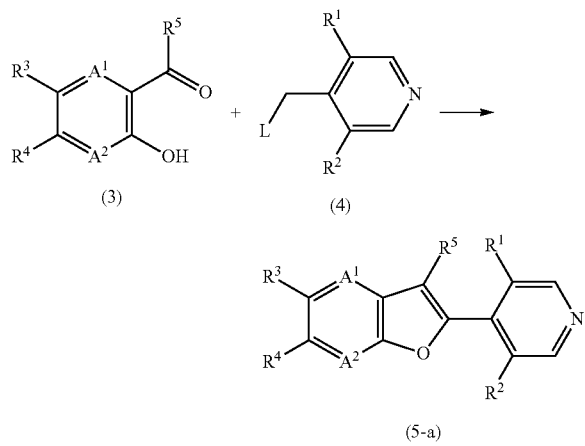

(3) + (4) → (5-a)

wherein $R^1$, $R^2$, $R^3$, $R^4$, $R^5$, $A^1$, and $A^2$ have the same meaning as defined above, and L is a leaving group such as chlorine, bromine, iodine, —OS(O)$_2$CF$_3$, or —OS(O)$_2$CH$_3$.

The reaction is generally carried out in the presence of a solvent.

Examples of the solvent used in the reaction include: acid amides such as N, N-dimethylformamide (hereinafter, referred to as DMF); sulfoxides such as dimethyl sulfoxide (hereinafter, referred to as DMSO); and mixtures thereof.

Examples of the base used in the reaction include: alkali metal hydrides such as sodium hydride; and carbonates such as potassium carbonate.

In the reaction, the compound (4) or a hydrochloride thereof is generally used at a ratio of 1 to 3 moles, based on 1 mole of the compound (3), and the base is generally used at a ratio of 2 to 5 moles, based on 1 mole of the compound (3).

The reaction temperature of the reaction is generally in a range of from 20 to 200° C. The reaction time of the reaction is generally in a range of from 0.1 to 24 hours.

After completion of the reaction, the reaction mixture is added to water, then the mixture is extracted with an organic solvent, and the organic layer is subjected to post-treatment operations such as drying or concentration, whereby the compound (5-a) can be isolated. The isolated compound (5-a) can be purified by chromatography, recrystallization, or the like.

(Production Method 2)

A compound (5-c), that is a compound, wherein, in the formula (1), n is 0 and R is —OR$^{7x}$, can be produced by reacting a compound (5-b) with a compound (6) in the presence of a base:

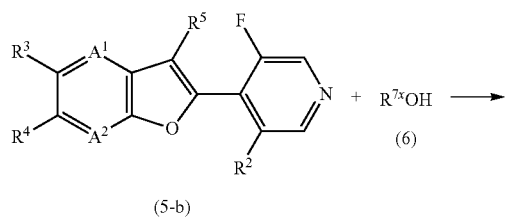

(5-b) + R$^{7x}$OH (6) →

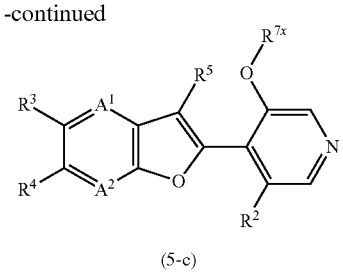

(5-c)

wherein $R^2$, $R^3$, $R^4$, $R^5$, $A^1$, and $A^2$ have the same meaning as defined above, and $R^{7x}$ is a C1 to C6 chain hydrocarbon group optionally substituted with at least one selected from group X, a C4 to C7 cycloalkylmethyl group optionally substituted with at least one selected from group X, a C3 to C6 alicyclic hydrocarbon group optionally substituted with at least one selected from group X, a phenyl group optionally substituted with at least one selected from group Y, a benzyl group optionally substituted with at least one selected from group Y, a five-membered heterocyclic group optionally substituted with at least one selected from group Y, or a six-membered heterocyclic group optionally substituted with at least one selected from group Y.

The reaction can be carried out in the presence of a solvent. The reaction can also be carried out in a solvent amount of the compound (6).

Examples of the solvent used in the reaction include: ethers such as tetrahydrofuran (hereinafter, referred to as THF), ethylene glycol dimethyl ether, and 1,4-dioxane; aromatic hydrocarbons such as toluene and xylene; nitriles such as acetonitrile; acid amides such as DMF; sulfoxides such as DMSO; and mixtures thereof.

Examples of the base used in the reaction include: alkali metal hydrides such as sodium hydride; and carbonates such as potassium carbonate.

In the reaction, the compound (6) is generally used at a ratio of 1 to 100 moles, based on 1 mole of the compound (5-b), and the base is generally used at a ratio of 1 to 10 moles, based on 1 mole of the compound (5-b).

The reaction temperature of the reaction is generally in a range of from 0 to 120° C. The reaction time of the reaction is generally in a range of from 0.5 to 24 hours.

After completion of the reaction, the reaction mixture is added to water, then the mixture is extracted with an organic solvent, and the organic layer is subjected to post-treatment operations such as drying or concentration, whereby the compound (5-c) can be isolated. The isolated compound (5-c) can be purified by chromatography, recrystallization, or the like.

(Production Method 3)

A compound (5-d), that is a compound, wherein, in the formula (1), n is 0 and $R^1$ is —SR$^{7x}$, can be produced by reacting a compound (5-b) with a compound (7) in the presence of a base:

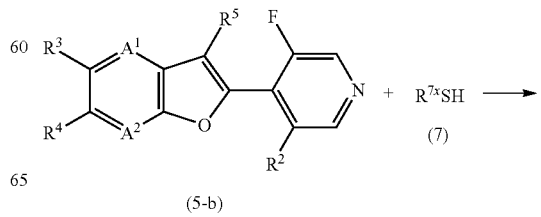

(5-b) + R$^{7x}$SH (7) →

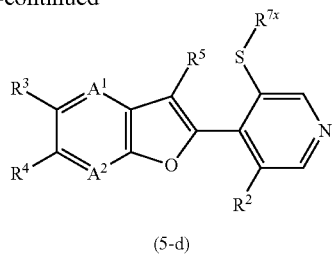

(5-d)

wherein $R^2$, $R^3$, $R^4$, $R^5$, $R^{7x}$, $A^1$, and $A^2$ have the same meaning as defined above.

The reaction is generally carried out in the presence of a solvent.

Examples of the solvent used in the reaction include: ethers such as THF, ethylene glycol dimethyl ether, and 1,4-dioxane; aromatic hydrocarbons such as toluene and xylene; nitriles such as acetonitrile; acid amides such as DMF; sulfoxides such as DMSO; and mixtures thereof.

Examples of the base used in the reaction include: alkali metal hydrides such as sodium hydride; and carbonates such as potassium carbonate.

In the reaction, the compound (7) is generally used at a ratio of 0.5 to 10 moles, based on 1 mole of the compound (5-b), and the base is generally used at a ratio of 0.5 to 10 moles, based on 1 mole of the compound (5-b).

The reaction temperature of the reaction is generally in a range of from 0 to 100° C. The reaction time of the reaction is generally in a range of from 0.1 to 24 hours.

After completion of the reaction, the reaction mixture is added to water, then the mixture is extracted with an organic solvent, and the organic layer is subjected to post-treatment operations such as drying or concentration, whereby the compound (5-d) can be isolated. The isolated compound (5-d) can be purified by chromatography, recrystallization, or the like.

(Production Method 4)

A compound (5-e), that is a compound, wherein, in the formula (1), n is 0 and $R^5$ is hydrogen, can be produced by reacting a compound (8) with a compound (9) in the presence of a palladium compound, a base, and a copper salt:

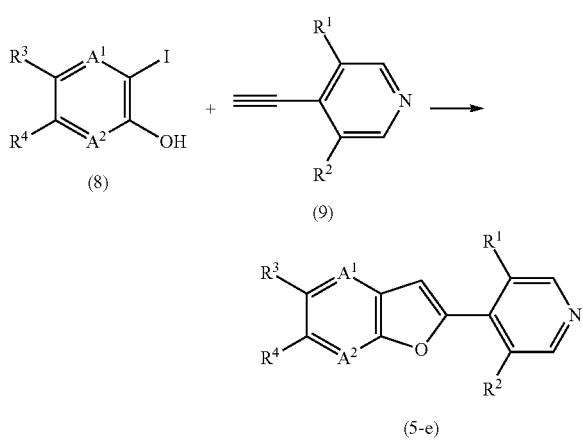

wherein $R^1$, $R^2$, $R^3$, $R^4$, and $A^2$ have the same meaning as defined above.

The reaction is generally carried out in the presence of a solvent.

Examples of the solvent used in the reaction include: ethers such as THF, ethylene glycol dimethyl ether, and 1,4-dioxane; acid amides such as DMF; and mixtures thereof.

Examples of the base used in the reaction include amines such as triethylamine, diethylamine, and diisopropylethylamine.

Examples of the palladium compound used in the reaction include tetrakistriphenylphosphine palladium, a {1,1'-bis(diphenylphosphino)ferrocene}dichloropalladium chloromethylene complex, and dichlorobis(triphenylphosphine)palladium(II).

Examples of the copper salt used in the reaction include copper(I) iodide.

In the reaction, the compound (9) is generally used at a ratio of 0.5 to 5 moles, based on 1 mole of the compound (8), the base is generally used at a ratio of 1 to 10 moles, based on 1 mole of the compound (8), the palladium compound is generally used at a ratio of 0.001 to 0.1 moles, based on 1 mole of the compound (8), and the copper salt is generally used at a ratio of 0.001 to 0.1 moles, based on 1 mole of the compound (8).

The reaction temperature of the reaction is generally in a range of from 0 to 100° C. The reaction time of the reaction is generally in a range of from 0.5 to 24 hours.

After completion of the reaction, the reaction mixture is extracted with an organic solvent, and the organic layer is subjected to post-treatment operations such as drying or concentration, whereby the compound (5-e) can be isolated. The isolated compound (5-e) can be purified by chromatography, recrystallization, or the like.

(Production Method 5)

A compound (10), that is a compound, wherein, in the formula (1), n is 1, can be produced by subjecting a compound (5-f) to an oxidation reaction:

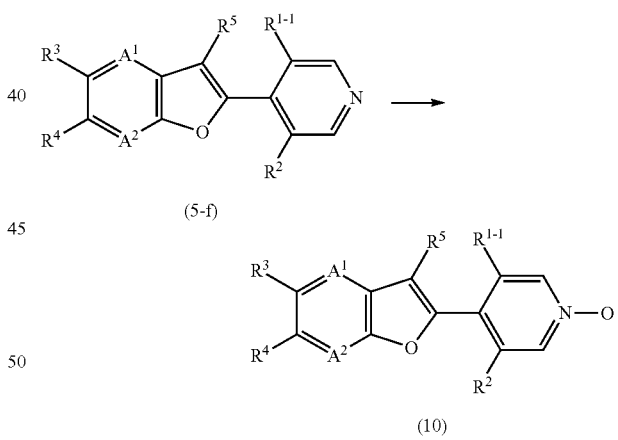

wherein $R^2$, $R^3$, $R^4$, $R^5$, $A^1$, and $A^2$ have the same meaning as defined above, and $R^{1-1}$ is a C1 to C6 chain hydrocarbon group optionally substituted with at least one selected from group X, a C3 to C6 alicyclic hydrocarbon group optionally substituted with at least one selected from group X, a phenyl group optionally substituted with at least one selected from group Y, a five-membered heterocyclic group optionally substituted with at least one selected from group Y, a six-membered heterocyclic group optionally substituted with at least one selected from group Y, $-OR^7$, $-NR^7R^8$, $-NR^7C(O)R^9$, $-NR^7CO_2R^{10}$, $-C(O)R^{11}$, $-C(NOR^7)R^{11}$, $-CO_2R^{11}$, $-CONR^7R^8$, $-CONR^{11}NR^{12}R^{13}$, a cyano group, a nitro group, a halogen, or hydrogen.

The reaction is generally carried out in the presence of a solvent.

Examples of the solvent used in the reaction include: aliphatic halogenated hydrocarbons such as dichloromethane and chloroform; acetic acid, water; and mixtures thereof.

Examples of the oxidizing agent used in the reaction include: peracids such as 3-chloroperbenzoic acid; and a hydrogen peroxide solution.

In the reaction, the oxidizing agent is generally used at a ratio of 1 to 3 moles, based on 1 mole of the compound (5-f).

The reaction temperature of the reaction is generally in a range of from −20 to 100° C. The reaction time of the reaction is generally in a range of from 0.1 to 24 hours.

After completion of the reaction, the reaction mixture is added to water, then the mixture is extracted with an organic solvent, and the organic layer is washed with an aqueous solution of a reducing agent and an aqueous solution of a base, as necessary, and subjected to post-treatment operations such as drying or concentration, whereby the compound (10) can be isolated. The isolated compound (10) can be purified by chromatography, recrystallization, or the like.

(Production Method 6)

A compound (5-h), that is a compound, wherein, in the formula (1), n is 1 and $R^1$ is $-SR^{7x}$, can be produced by reacting a compound (5-g) with a compound (7) in the presence of a base:

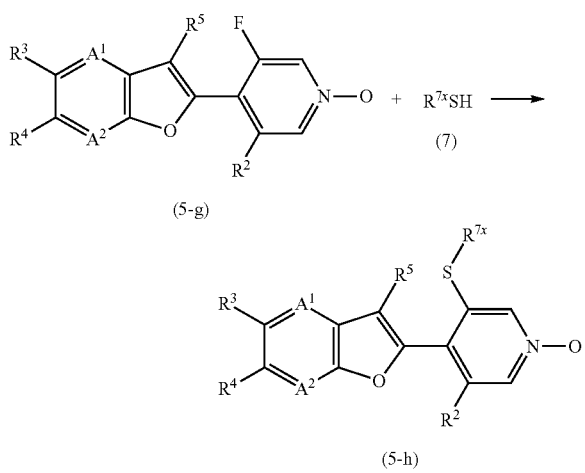

wherein $R^2$, $R^3$, $R^4$, $R^5$, $R^{7x}$, $A^1$, and $A^2$ have the same meaning as defined above.

The reaction is generally carried out in the presence of a solvent and in the presence of a base.

Examples of the solvent used in the reaction include: ethers such as THF, ethylene glycol dimethyl ether, and 1,4-dioxane; aromatic hydrocarbons such as toluene and xylene; nitriles such as acetonitrile; acid amides such as DMF; sulfoxides such as DMSO; and mixtures thereof.

Examples of the base used in the reaction include: alkali metal hydrides such as sodium hydride; and carbonates such as potassium carbonate.

In the reaction, the compound (7) is generally used at a ratio of 0.5 to 10 moles, based on 1 mole of the compound (5-g), and the base is generally used at a ratio of 0.5 to 10 moles, based on 1 mole of the compound (5-g).

The reaction temperature of the reaction is generally in a range of from 0 to 100° C. The reaction time of the reaction is generally in a range of from 0.1 to 24 hours.

After completion of the reaction, the reaction mixture is added to water, then the mixture is extracted with an organic solvent, and the organic layer is subjected to post-treatment operations such as drying or concentration, whereby the compound (5-h) can be isolated. The isolated compound (5-h) can be purified by chromatography, recrystallization, or the like.

Among the intermediates of the present active compound, a compound (4-a) can be produced, for example, by reacting a compound (II) with a chlorinating agent:

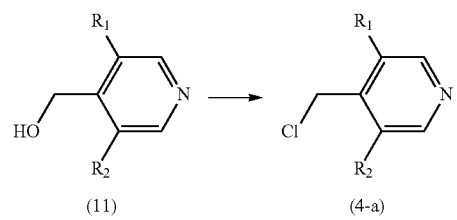

wherein $R^1$ and $R^2$ have the same meaning as defined above.

This reaction can be carried out in the presence or absence of a solvent.

Examples of the solvent used in the reaction include aliphatic halogenated hydrocarbons such as dichloromethane and chloroform.

Examples of the chlorinating agent used in the reaction include phosphoryl chloride, thionyl chloride and oxalyl chloride.

In the reaction, the chlorinating agent is generally used at a ratio of 1 to 5 moles, based on 1 mole of the compound (II). When phosphoryl chloride is used as the chlorinating agent, the reaction can also be carried out in a solvent amount of phosphoryl chloride.

The reaction temperature of the reaction is generally in a range of from 0 to 110° C. The reaction time of the reaction is generally in a range of from 0.1 to 24 hours.

After completion of the reaction, the reaction mixture is added to water, then the mixture is extracted with an organic solvent, and the organic layer is washed with an aqueous solution of a base, as necessary, and subjected to post-treatment operations such as drying or concentration, whereby the compound (4-a) can be isolated. The isolated compound (4-a) can be purified by chromatography, recrystallization, or the like.

Next, specific examples of the present active compound will be given below.

In the following tables, Me represents a methyl group, Et represents an ethyl group, Pr represents a propyl group, iPr represents an isopropyl group, cPr represents a cyclopropyl group, tBu represents a tert-butyl group, cPen represents a cyclopentyl group, Ph represents a phenyl group, 2-Py represents a 2-pyridyl group, 3-Py represents a 3-pyridyl group, 4-Py represents a 4-pyridyl group, 1-Tz represents a 1,2,4-triazol-1-yl group, and 1-Pz represents a pyrazol-1-yl group.

The compound represented by the formula (1).

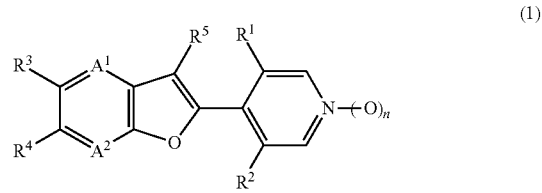

In the formula (1), substituents of $R^1$, $R^2$, $R^3$, $R^4$, $R^5$, $A^1$, $A^2$, and n are the combinations shown in the following (Table 1) to (Table 42).

TABLE 1

| R¹ | R² | R³ | R⁴ | R⁵ | A¹ | A² | n |
|---|---|---|---|---|---|---|---|
| H | H | tBu | H | H | =C(H)— | =C(H)— | 0 |
| F | H | tBu | H | H | =C(H)— | =C(H)— | 0 |
| Cl | H | tBu | H | H | =C(H)— | =C(H)— | 0 |
| Br | H | tBu | H | H | =C(H)— | =C(H)— | 0 |
| I | H | tBu | H | H | =C(H)— | =C(H)— | 0 |
| Me | H | tBu | H | H | =C(H)— | =C(H)— | 0 |
| Et | H | tBu | H | H | =C(H)— | =C(H)— | 0 |
| Pr | H | tBu | H | H | =C(H)— | =C(H)— | 0 |
| cPr | H | tBu | H | H | =C(H)— | =C(H)— | 0 |
| CF₃ | H | tBu | H | H | =C(H)— | =C(H)— | 0 |
| CH₃OCH₂ | H | tBu | H | H | =C(H)— | =C(H)— | 0 |
| MeO | H | tBu | H | H | =C(H)— | =C(H)— | 0 |
| EtO | H | tBu | H | H | =C(H)— | =C(H)— | 0 |
| PrO | H | tBu | H | H | =C(H)— | =C(H)— | 0 |
| CF₃CH₂O | H | tBu | H | H | =C(H)— | =C(H)— | 0 |
| CHF₂CH₂O | H | tBu | H | H | =C(H)— | =C(H)— | 0 |
| iPrO | H | tBu | H | H | =C(H)— | =C(H)— | 0 |
| cPrCH₂O | H | tBu | H | H | =C(H)— | =C(H)— | 0 |
| cPenO | H | tBu | H | H | =C(H)— | =C(H)— | 0 |
| MeS | H | tBu | H | H | =C(H)— | =C(H)— | 0 |
| MeS(O) | H | tBu | H | H | =C(H)— | =C(H)— | 0 |
| MeS(O)₂ | H | tBu | H | H | =C(H)— | =C(H)— | 0 |
| EtS | H | tBu | H | H | =C(H)— | =C(H)— | 0 |
| EtS(O) | H | tBu | H | H | =C(H)— | =C(H)— | 0 |

TABLE 2

| R¹ | R² | R³ | R⁴ | R⁵ | A¹ | A² | n |
|---|---|---|---|---|---|---|---|
| EtS(O)₂ | H | tBu | H | H | =C(H)— | =C(H)— | 0 |
| PrS | H | tBu | H | H | =C(H)— | =C(H)— | 0 |
| PrS(O) | H | tBu | H | H | =C(H)— | =C(H)— | 0 |
| PrS(O)₂ | H | tBu | H | H | =C(H)— | =C(H)— | 0 |
| iPrS | H | tBu | H | H | =C(H)— | =C(H)— | 0 |
| iPrS(O) | H | tBu | H | H | =C(H)— | =C(H)— | 0 |
| iPrS(O)₂ | H | tBu | H | H | =C(H)— | =C(H)— | 0 |
| CF₃CH₂S | H | tBu | H | H | =C(H)— | =C(H)— | 0 |
| CHF₂CH₂S | H | tBu | H | H | =C(H)— | =C(H)— | 0 |
| MeHN | H | tBu | H | H | =C(H)— | =C(H)— | 0 |
| Me₂N | H | tBu | H | H | =C(H)— | =C(H)— | 0 |
| Me(iPr)N | H | tBu | H | H | =C(H)— | =C(H)— | 0 |
| Ph | H | tBu | H | H | =C(H)— | =C(H)— | 0 |
| 2-Py | H | tBu | H | H | =C(H)— | =C(H)— | 0 |
| 3-Py | H | tBu | H | H | =C(H)— | =C(H)— | 0 |
| 4-Py | H | tBu | H | H | =C(H)— | =C(H)— | 0 |
| 1-Tz | H | tBu | H | H | =C(H)— | =C(H)— | 0 |
| 1-Pz | H | tBu | H | H | =C(H)— | =C(H)— | 0 |
| H | H | tBu | H | H | =C(H)— | =C(H)— | 1 |
| F | H | tBu | H | H | =C(H)— | =C(H)— | 1 |
| Cl | H | tBu | H | H | =C(H)— | =C(H)— | 1 |
| Br | H | tBu | H | H | =C(H)— | =C(H)— | 1 |
| I | H | tBu | H | H | =C(H)— | =C(H)— | 1 |
| Me | H | tBu | H | H | =C(H)— | =C(H)— | 1 |

TABLE 3

| R¹ | R² | R³ | R⁴ | R⁵ | A¹ | A² | n |
|---|---|---|---|---|---|---|---|
| Et | H | tBu | H | H | =C(H)— | =C(H)— | 1 |
| Pr | H | tBu | H | H | =C(H)— | =C(H)— | 1 |
| cPr | H | tBu | H | H | =C(H)— | =C(H)— | 1 |
| CF₃ | H | tBu | H | H | =C(H)— | =C(H)— | 1 |
| CH₃OCH₂ | H | tBu | H | H | =C(H)— | =C(H)— | 1 |
| MeO | H | tBu | H | H | =C(H)— | =C(H)— | 1 |
| EtO | H | tBu | H | H | =C(H)— | =C(H)— | 1 |
| PrO | H | tBu | H | H | =C(H)— | =C(H)— | 1 |
| CF₃CH₂O | H | tBu | H | H | =C(H)— | =C(H)— | 1 |
| CHF₂CH₂O | H | tBu | H | H | =C(H)— | =C(H)— | 1 |
| iPrO | H | tBu | H | H | =C(H)— | =C(H)— | 1 |
| Ph | H | tBu | H | H | =C(H)— | =C(H)— | 1 |
| H | H | H | tBu | H | =C(H)— | =C(H)— | 0 |
| F | H | H | tBu | H | =C(H)— | =C(H)— | 0 |
| Cl | H | H | tBu | H | =C(H)— | =C(H)— | 0 |
| Br | H | H | tBu | H | =C(H)— | =C(H)— | 0 |
| I | H | H | tBu | H | =C(H)— | =C(H)— | 0 |
| Me | H | H | tBu | H | =C(H)— | =C(H)— | 0 |
| Et | H | H | tBu | H | =C(H)— | =C(H)— | 0 |
| Pr | H | H | tBu | H | =C(H)— | =C(H)— | 0 |
| cPr | H | H | tBu | H | =C(H)— | =C(H)— | 0 |
| CF₃ | H | H | tBu | H | =C(H)— | =C(H)— | 0 |
| CH₃OCH₂ | H | H | tBu | H | =C(H)— | =C(H)— | 0 |
| MeO | H | H | tBu | H | =C(H)— | =C(H)— | 0 |

TABLE 4

| R¹ | R² | R³ | R⁴ | R⁵ | A¹ | A² | n |
|---|---|---|---|---|---|---|---|
| EtO | H | H | tBu | H | =C(H)— | =C(H)— | 0 |
| PrO | H | H | tBu | H | =C(H)— | =C(H)— | 0 |
| CF₃CH₂O | H | H | tBu | H | =C(H)— | =C(H)— | 0 |
| CHF₂CH₂O | H | H | tBu | H | =C(H)— | =C(H)— | 0 |
| iPrO | H | H | tBu | H | =C(H)— | =C(H)— | 0 |
| cPrCH₂O | H | H | tBu | H | =C(H)— | =C(H)— | 0 |
| cPenO | H | H | tBu | H | =C(H)— | =C(H)— | 0 |
| MeS | H | H | tBu | H | =C(H)— | =C(H)— | 0 |
| MeS(O) | H | H | tBu | H | =C(H)— | =C(H)— | 0 |
| MeS(O)₂ | H | H | tBu | H | =C(H)— | =C(H)— | 0 |
| EtS | H | H | tBu | H | =C(H)— | =C(H)— | 0 |
| EtS(O) | H | H | tBu | H | =C(H)— | =C(H)— | 0 |
| EtS(O)₂ | H | H | tBu | H | =C(H)— | =C(H)— | 0 |
| PrS | H | H | tBu | H | =C(H)— | =C(H)— | 0 |
| PrS(O) | H | H | tBu | H | =C(H)— | =C(H)— | 0 |
| PrS(O)₂ | H | H | tBu | H | =C(H)— | =C(H)— | 0 |
| iPrS | H | H | tBu | H | =C(H)— | =C(H)— | 0 |
| iPrS(O) | H | H | tBu | H | =C(H)— | =C(H)— | 0 |
| iPrS(O)₂ | H | H | tBu | H | =C(H)— | =C(H)— | 0 |
| CF₃CH₂S | H | H | tBu | H | =C(H)— | =C(H)— | 0 |
| CHF₂CH₂S | H | H | tBu | H | =C(H)— | =C(H)— | 0 |
| H | H | CF₃ | H | H | =C(H)— | =C(H)— | 0 |
| F | H | CF₃ | H | H | =C(H)— | =C(H)— | 0 |
| Cl | H | CF₃ | H | H | =C(H)— | =C(H)— | 0 |

TABLE 5

| R¹ | R² | R³ | R⁴ | R⁵ | A¹ | A² | n |
|---|---|---|---|---|---|---|---|
| Br | H | CF₃ | H | H | =C(H)— | =C(H)— | 0 |
| I | H | CF₃ | H | H | =C(H)— | =C(H)— | 0 |
| Me | H | CF₃ | H | H | =C(H)— | =C(H)— | 0 |
| Et | H | CF₃ | H | H | =C(H)— | =C(H)— | 0 |
| Pr | H | CF₃ | H | H | =C(H)— | =C(H)— | 0 |
| cPr | H | CF₃ | H | H | =C(H)— | =C(H)— | 0 |
| CF₃ | H | CF₃ | H | H | =C(H)— | =C(H)— | 0 |
| CH₃OCH₂ | H | CF₃ | H | H | =C(H)— | =C(H)— | 0 |
| MeO | H | CF₃ | H | H | =C(H)— | =C(H)— | 0 |
| EtO | H | CF₃ | H | H | =C(H)— | =C(H)— | 0 |
| PrO | H | CF₃ | H | H | =C(H)— | =C(H)— | 0 |
| CF₃CH₂O | H | CF₃ | H | H | =C(H)— | =C(H)— | 0 |
| CHF₂CH₂O | H | CF₃ | H | H | =C(H)— | =C(H)— | 0 |
| iPrO | H | CF₃ | H | H | =C(H)— | =C(H)— | 0 |
| cPrCH₂O | H | CF₃ | H | H | =C(H)— | =C(H)— | 0 |
| cPenO | H | CF₃ | H | H | =C(H)— | =C(H)— | 0 |
| MeS | H | CF₃ | H | H | =C(H)— | =C(H)— | 0 |
| MeS(O) | H | CF₃ | H | H | =C(H)— | =C(H)— | 0 |
| MeS(O)₂ | H | CF₃ | H | H | =C(H)— | =C(H)— | 0 |
| EtS | H | CF₃ | H | H | =C(H)— | =C(H)— | 0 |
| EtS(O) | H | CF₃ | H | H | =C(H)— | =C(H)— | 0 |
| EtS(O)₂ | H | CF₃ | H | H | =C(H)— | =C(H)— | 0 |
| PrS | H | CF₃ | H | H | =C(H)— | =C(H)— | 0 |
| PrS(O) | H | CF₃ | H | H | =C(H)— | =C(H)— | 0 |

TABLE 6

| R¹ | R² | R³ | R⁴ | R⁵ | A¹ | A² | n |
|---|---|---|---|---|---|---|---|
| PrS(O)₂ | H | CF₃ | H | H | =C(H)— | =C(H)— | 0 |
| iPrS | H | CF₃ | H | H | =C(H)— | =C(H)— | 0 |
| iPrS(O) | H | CF₃ | H | H | =C(H)— | =C(H)— | 0 |
| iPrS(O)₂ | H | CF₃ | H | H | =C(H)— | =C(H)— | 0 |
| CF₃CH₂S | H | CF₃ | H | H | =C(H)— | =C(H)— | 0 |
| CHF₂CH₂S | H | CF₃ | H | H | =C(H)— | =C(H)— | 0 |
| MeHN | H | CF₃ | H | H | =C(H)— | =C(H)— | 0 |
| Me₂N | H | CF₃ | H | H | =C(H)— | =C(H)— | 0 |
| Me(iPr)N | H | CF₃ | H | H | =C(H)— | =C(H)— | 0 |
| CH₃C(O)NH | H | CF₃ | H | H | =C(H)— | =C(H)— | 0 |
| MeOC(O)NH | H | CF₃ | H | H | =C(H)— | =C(H)— | 0 |
| HC(O) | H | CF₃ | H | H | =C(H)— | =C(H)— | 0 |
| CH₃C(O) | H | CF₃ | H | H | =C(H)— | =C(H)— | 0 |
| HC(NOMe) | H | CF₃ | H | H | =C(H)— | =C(H)— | 0 |
| CH₃C(NOMe) | H | CF₃ | H | H | =C(H)— | =C(H)— | 0 |
| Ph | H | CF₃ | H | H | =C(H)— | =C(H)— | 0 |
| 2-Py | H | CF₃ | H | H | =C(H)— | =C(H)— | 0 |
| 3-Py | H | CF₃ | H | H | =C(H)— | =C(H)— | 0 |
| 4-Py | H | CF₃ | H | H | =C(H)— | =C(H)— | 0 |
| 1-Tz | H | CF₃ | H | H | =C(H)— | =C(H)— | 0 |
| 1-Pz | H | CF₃ | H | H | =C(H)— | =C(H)— | 0 |
| H | H | CF₃ | H | H | =C(H)— | =C(H)— | 1 |
| F | H | CF₃ | H | H | =C(H)— | =C(H)— | 1 |
| Cl | H | CF₃ | H | H | =C(H)— | =C(H)— | 1 |

TABLE 7

| R¹ | R² | R³ | R⁴ | R⁵ | A¹ | A² | n |
|---|---|---|---|---|---|---|---|
| Br | H | CF₃ | H | H | =C(H)— | =C(H)— | 1 |
| I | H | CF₃ | H | H | =C(H)— | =C(H)— | 1 |
| Me | H | CF₃ | H | H | =C(H)— | =C(H)— | 1 |
| Et | H | CF₃ | H | H | =C(H)— | =C(H)— | 1 |
| Pr | H | CF₃ | H | H | =C(H)— | =C(H)— | 1 |
| cPr | H | CF₃ | H | H | =C(H)— | =C(H)— | 1 |
| CF₃ | H | CF₃ | H | H | =C(H)— | =C(H)— | 1 |
| CH₃OCH₂ | H | CF₃ | H | H | =C(H)— | =C(H)— | 1 |
| MeO | H | CF₃ | H | H | =C(H)— | =C(H)— | 1 |
| EtO | H | CF₃ | H | H | =C(H)— | =C(H)— | 1 |
| PrO | H | CF₃ | H | H | =C(H)— | =C(H)— | 1 |
| CF₃CH₂O | H | CF₃ | H | H | =C(H)— | =C(H)— | 1 |
| CHF₂CH₂O | H | CF₃ | H | H | =C(H)— | =C(H)— | 1 |
| iPrO | H | CF₃ | H | H | =C(H)— | =C(H)— | 1 |
| Ph | H | CF₃ | H | H | =C(H)— | =C(H)— | 1 |
| H | H | CF₃ | Cl | H | =C(H)— | =C(H)— | 0 |
| F | H | CF₃ | Cl | H | =C(H)— | =C(H)— | 0 |
| Cl | H | CF₃ | Cl | H | =C(H)— | =C(H)— | 0 |
| Br | H | CF₃ | Cl | H | =C(H)— | =C(H)— | 0 |
| I | H | CF₃ | Cl | H | =C(H)— | =C(H)— | 0 |
| Me | H | CF₃ | Cl | H | =C(H)— | =C(H)— | 0 |
| Et | H | CF₃ | Cl | H | =C(H)— | =C(H)— | 0 |
| Pr | H | CF₃ | Cl | H | =C(H)— | =C(H)— | 0 |
| CF₃ | H | CF₃ | Cl | H | =C(H)— | =C(H)— | 0 |

TABLE 8

| R¹ | R² | R³ | R⁴ | R⁵ | A¹ | A² | n |
|---|---|---|---|---|---|---|---|
| CH₃OCH₂ | H | CF₃ | Cl | H | =C(H)— | =C(H)— | 0 |
| MeO | H | CF₃ | Cl | H | =C(H)— | =C(H)— | 0 |
| EtO | H | CF₃ | Cl | H | =C(H)— | =C(H)— | 0 |
| PrO | H | CF₃ | Cl | H | =C(H)— | =C(H)— | 0 |
| CF₃CH₂O | H | CF₃ | Cl | H | =C(H)— | =C(H)— | 0 |
| CHF₂CH₂O | H | CF₃ | Cl | H | =C(H)— | =C(H)— | 0 |
| iPrO | H | CF₃ | Cl | H | =C(H)— | =C(H)— | 0 |
| MeS | H | CF₃ | Cl | H | =C(H)— | =C(H)— | 0 |
| MeS(O) | H | CF₃ | Cl | H | =C(H)— | =C(H)— | 0 |
| MeS(O)₂ | H | CF₃ | Cl | H | =C(H)— | =C(H)— | 0 |
| EtS | H | CF₃ | Cl | H | =C(H)— | =C(H)— | 0 |
| EtS(O) | H | CF₃ | Cl | H | =C(H)— | =C(H)— | 0 |
| EtS(O)₂ | H | CF₃ | Cl | H | =C(H)— | =C(H)— | 0 |
| PrS | H | CF₃ | Cl | H | =C(H)— | =C(H)— | 0 |
| PrS(O) | H | CF₃ | Cl | H | =C(H)— | =C(H)— | 0 |

TABLE 8-continued

| R¹ | R² | R³ | R⁴ | R⁵ | A¹ | A² | n |
|---|---|---|---|---|---|---|---|
| PrS(O)₂ | H | CF₃ | Cl | H | =C(H)— | =C(H)— | 0 |
| iPrS | H | CF₃ | Cl | H | =C(H)— | =C(H)— | 0 |
| iPrS(O) | H | CF₃ | Cl | H | =C(H)— | =C(H)— | 0 |
| iPrS(O)₂ | H | CF₃ | Cl | H | =C(H)— | =C(H)— | 0 |
| CF₃CH₂S | H | CF₃ | Cl | H | =C(H)— | =C(H)— | 0 |
| CHF₂CH₂S | H | CF₃ | Cl | H | =C(H)— | =C(H)— | 0 |
| H | H | CF₃ | H | H | =C(H)— | =C(Cl)— | 0 |
| F | H | CF₃ | H | H | =C(H)— | =C(Cl)— | 0 |
| Cl | H | CF₃ | H | H | =C(H)— | =C(Cl)— | 0 |

TABLE 9

| R¹ | R² | R³ | R⁴ | R⁵ | A¹ | A² | n |
|---|---|---|---|---|---|---|---|
| Br | H | CF₃ | H | H | =C(H)— | =C(Cl)— | 0 |
| I | H | CF₃ | H | H | =C(H)— | =C(Cl)— | 0 |
| Me | H | CF₃ | H | H | =C(H)— | =C(Cl)— | 0 |
| Et | H | CF₃ | H | H | =C(H)— | =C(Cl)— | 0 |
| Pr | H | CF₃ | H | H | =C(H)— | =C(Cl)— | 0 |
| CF₃ | H | CF₃ | H | H | =C(H)— | =C(Cl)— | 0 |
| CH₃OCH₂ | H | CF₃ | H | H | =C(H)— | =C(Cl)— | 0 |
| MeO | H | CF₃ | H | H | =C(H)— | =C(Cl)— | 0 |
| EtO | H | CF₃ | H | H | =C(H)— | =C(Cl)— | 0 |
| PrO | H | CF₃ | H | H | =C(H)— | =C(Cl)— | 0 |
| CF₃CH₂O | H | CF₃ | H | H | =C(H)— | =C(Cl)— | 0 |
| CHF₂CH₂O | H | CF₃ | H | H | =C(H)— | =C(Cl)— | 0 |
| iPrO | H | CF₃ | H | H | =C(H)— | =C(Cl)— | 0 |
| MeS | H | CF₃ | H | H | =C(H)— | =C(Cl)— | 0 |
| MeS(O) | H | CF₃ | H | H | =C(H)— | =C(Cl)— | 0 |
| MeS(O)₂ | H | CF₃ | H | H | =C(H)— | =C(Cl)— | 0 |
| EtS | H | CF₃ | H | H | =C(H)— | =C(Cl)— | 0 |
| EtS(O) | H | CF₃ | H | H | =C(H)— | =C(Cl)— | 0 |
| EtS(O)₂ | H | CF₃ | H | H | =C(H)— | =C(Cl)— | 0 |
| PrS | H | CF₃ | H | H | =C(H)— | =C(Cl)— | 0 |
| PrS(O) | H | CF₃ | H | H | =C(H)— | =C(Cl)— | 0 |
| PrS(O)₂ | H | CF₃ | H | H | =C(H)— | =C(Cl)— | 0 |
| iPrS | H | CF₃ | H | H | =C(H)— | =C(Cl)— | 0 |
| iPrS(O) | H | CF₃ | H | H | =C(H)— | =C(Cl)— | 0 |

TABLE 10

| R¹ | R² | R³ | R⁴ | R⁵ | A¹ | A² | n |
|---|---|---|---|---|---|---|---|
| iPrS(O)₂ | H | CF₃ | H | H | =C(H)— | =C(Cl)— | 0 |
| CF₃CH₂S | H | CF₃ | H | H | =C(H)— | =C(Cl)— | 0 |
| CHF₂CH₂S | H | CF₃ | H | H | =C(H)— | =C(Cl)— | 0 |
| Cl | Cl | CF₃ | H | H | =C(H)— | =C(H)— | 0 |
| MeO | Cl | CF₃ | H | H | =C(H)— | =C(H)— | 0 |
| EtO | Cl | CF₃ | H | H | =C(H)— | =C(H)— | 0 |
| PrO | Cl | CF₃ | H | H | =C(H)— | =C(H)— | 0 |
| CF₃CH₂O | Cl | CF₃ | H | H | =C(H)— | =C(H)— | 0 |
| CHF₂CH₂O | Cl | CF₃ | H | H | =C(H)— | =C(H)— | 0 |
| iPrO | Cl | CF₃ | H | H | =C(H)— | =C(H)— | 0 |
| MeS | Cl | CF₃ | H | H | =C(H)— | =C(H)— | 0 |
| MeS(O) | Cl | CF₃ | H | H | =C(H)— | =C(H)— | 0 |
| MeS(O)₂ | Cl | CF₃ | H | H | =C(H)— | =C(H)— | 0 |
| EtS | Cl | CF₃ | H | H | =C(H)— | =C(H)— | 0 |
| EtS(O) | Cl | CF₃ | H | H | =C(H)— | =C(H)— | 0 |
| EtS(O)₂ | Cl | CF₃ | H | H | =C(H)— | =C(H)— | 0 |
| CF₃CH₂S | Cl | CF₃ | H | H | =C(H)— | =C(H)— | 0 |
| CHF₂CH₂S | Cl | CF₃ | H | H | =C(H)— | =C(H)— | 0 |
| MeHN | Cl | CF₃ | H | H | =C(H)— | =C(H)— | 0 |
| Me₂N | Cl | CF₃ | H | H | =C(H)— | =C(H)— | 0 |
| Me(iPr)N | Cl | CF₃ | H | H | =C(H)— | =C(H)— | 0 |
| Cl | F | CF₃ | H | H | =C(H)— | =C(H)— | 0 |
| MeO | F | CF₃ | H | H | =C(H)— | =C(H)— | 0 |
| EtO | F | CF₃ | H | H | =C(H)— | =C(H)— | 0 |

TABLE 11

| R¹ | R² | R³ | R⁴ | R⁵ | A¹ | A² | n |
|---|---|---|---|---|---|---|---|
| PrO | F | CF₃ | H | H | =C(H)— | =C(H)— | 0 |
| CF₃CH₂O | F | CF₃ | H | H | =C(H)— | =C(H)— | 0 |
| CHF₂CH₂O | F | CF₃ | H | H | =C(H)— | =C(H)— | 0 |
| iPrO | F | CF₃ | H | H | =C(H)— | =C(H)— | 0 |
| MeS | F | CF₃ | H | H | =C(H)— | =C(H)— | 0 |
| MeS(O) | F | CF₃ | H | H | =C(H)— | =C(H)— | 0 |
| MeS(O)₂ | F | CF₃ | H | H | =C(H)— | =C(H)— | 0 |
| EtS | F | CF₃ | H | H | =C(H)— | =C(H)— | 0 |
| EtS(O) | F | CF₃ | H | H | =C(H)— | =C(H)— | 0 |
| EtS(O)₂ | F | CF₃ | H | H | =C(H)— | =C(H)— | 0 |
| CF₃CH₂S | F | CF₃ | H | H | =C(H)— | =C(H)— | 0 |
| CHF₂CH₂S | F | CF₃ | H | H | =C(H)— | =C(H)— | 0 |
| MeHN | F | CF₃ | H | H | =C(H)— | =C(H)— | 0 |
| Me₂N | F | CF₃ | H | H | =C(H)— | =C(H)— | 0 |
| Me(iPr)N | F | CF₃ | H | H | =C(H)— | =C(H)— | 0 |
| H | H | CF₃ | H | Me | =C(H)— | =C(H)— | 0 |
| F | H | CF₃ | H | Me | =C(H)— | =C(H)— | 0 |
| Cl | H | CF₃ | H | Me | =C(H)— | =C(H)— | 0 |
| Br | H | CF₃ | H | Me | =C(H)— | =C(H)— | 0 |
| I | H | CF₃ | H | Me | =C(H)— | =C(H)— | 0 |
| Me | H | CF₃ | H | Me | =C(H)— | =C(H)— | 0 |
| Et | H | CF₃ | H | Me | =C(H)— | =C(H)— | 0 |
| Pr | H | CF₃ | H | Me | =C(H)— | =C(H)— | 0 |
| CF₃ | H | CF₃ | H | Me | =C(H)— | =C(H)— | 0 |

TABLE 12

| R¹ | R² | R³ | R⁴ | R⁵ | A¹ | A² | n |
|---|---|---|---|---|---|---|---|
| CH₃OCH₂ | H | CF₃ | H | Me | =C(H)— | =C(H)— | 0 |
| MeO | H | CF₃ | H | Me | =C(H)— | =C(H)— | 0 |
| EtO | H | CF₃ | H | Me | =C(H)— | =C(H)— | 0 |
| PrO | H | CF₃ | H | Me | =C(H)— | =C(H)— | 0 |
| CF₃CH₂O | H | CF₃ | H | Me | =C(H)— | =C(H)— | 0 |
| CHF₂CH₂O | H | CF₃ | H | Me | =C(H)— | =C(H)— | 0 |
| iPrO | H | CF₃ | H | Me | =C(H)— | =C(H)— | 0 |
| MeS | H | CF₃ | H | Me | =C(H)— | =C(H)— | 0 |
| MeS(O) | H | CF₃ | H | Me | =C(H)— | =C(H)— | 0 |
| MeS(O)₂ | H | CF₃ | H | Me | =C(H)— | =C(H)— | 0 |
| EtS | H | CF₃ | H | Me | =C(H)— | =C(H)— | 0 |
| EtS(O) | H | CF₃ | H | Me | =C(H)— | =C(H)— | 0 |
| EtS(O)₂ | H | CF₃ | H | Me | =C(H)— | =C(H)— | 0 |
| PrS | H | CF₃ | H | Me | =C(H)— | =C(H)— | 0 |
| PrS(O) | H | CF₃ | H | Me | =C(H)— | =C(H)— | 0 |
| PrS(O)₂ | H | CF₃ | H | Me | =C(H)— | =C(H)— | 0 |
| iPrS | H | CF₃ | H | Me | =C(H)— | =C(H)— | 0 |
| iPrS(O) | H | CF₃ | H | Me | =C(H)— | =C(H)— | 0 |
| iPrS(O)₂ | H | CF₃ | H | Me | =C(H)— | =C(H)— | 0 |
| CF₃CH₂S | H | CF₃ | H | Me | =C(H)— | =C(H)— | 0 |
| CHF₂CH₂S | H | CF₃ | H | Me | =C(H)— | =C(H)— | 0 |
| H | H | CF₃O | H | H | =C(H)— | =C(H)— | 0 |
| F | H | CF₃O | H | H | =C(H)— | =C(H)— | 0 |
| Cl | H | CF₃O | H | H | =C(H)— | =C(H)— | 0 |

TABLE 13

| R¹ | R² | R³ | R⁴ | R⁵ | A¹ | A² | n |
|---|---|---|---|---|---|---|---|
| Br | H | CF₃O | H | H | =C(H)— | =C(H)— | 0 |
| I | H | CF₃O | H | H | =C(H)— | =C(H)— | 0 |
| Me | H | CF₃O | H | H | =C(H)— | =C(H)— | 0 |
| Et | H | CF₃O | H | H | =C(H)— | =C(H)— | 0 |
| Pr | H | CF₃O | H | H | =C(H)— | =C(H)— | 0 |
| cPr | H | CF₃O | H | H | =C(H)— | =C(H)— | 0 |
| CF₃ | H | CF₃O | H | H | =C(H)— | =C(H)— | 0 |
| CH₃OCH₂ | H | CF₃O | H | H | =C(H)— | =C(H)— | 0 |
| MeO | H | CF₃O | H | H | =C(H)— | =C(H)— | 0 |
| EtO | H | CF₃O | H | H | =C(H)— | =C(H)— | 0 |
| PrO | H | CF₃O | H | H | =C(H)— | =C(H)— | 0 |
| CF₃CH₂O | H | CF₃O | H | H | =C(H)— | =C(H)— | 0 |
| CHF₂CH₂O | H | CF₃O | H | H | =C(H)— | =C(H)— | 0 |
| iPrO | H | CF₃O | H | H | =C(H)— | =C(H)— | 0 |
| cPrCH₂O | H | CF₃O | H | H | =C(H)— | =C(H)— | 0 |

TABLE 13-continued

| R¹ | R² | R³ | R⁴ | R⁵ | A¹ | A² | n |
|---|---|---|---|---|---|---|---|
| cPenO | H | CF₃O | H | H | =C(H)— | =C(H)— | 0 |
| MeS | H | CF₃O | H | H | =C(H)— | =C(H)— | 0 |
| MeS(O) | H | CF₃O | H | H | =C(H)— | =C(H)— | 0 |
| MeS(O)₂ | H | CF₃O | H | H | =C(H)— | =C(H)— | 0 |
| EtS | H | CF₃O | H | H | =C(H)— | =C(H)— | 0 |
| EtS(O) | H | CF₃O | H | H | =C(H)— | =C(H)— | 0 |
| EtS(O)₂ | H | CF₃O | H | H | =C(H)— | =C(H)— | 0 |
| PrS | H | CF₃O | H | H | =C(H)— | =C(H)— | 0 |
| PrS(O) | H | CF₃O | H | H | =C(H)— | =C(H)— | 0 |

TABLE 14

| R¹ | R² | R³ | R⁴ | R⁵ | A¹ | A² | n |
|---|---|---|---|---|---|---|---|
| PrS(O)₂ | H | CF₃O | H | H | =C(H)— | =C(H)— | 0 |
| iPrS | H | CF₃O | H | H | =C(H)— | =C(H)— | 0 |
| iPrS(O) | H | CF₃O | H | H | =C(H)— | =C(H)— | 0 |
| iPrS(O)₂ | H | CF₃O | H | H | =C(H)— | =C(H)— | 0 |
| CF₃CH₂S | H | CF₃O | H | H | =C(H)— | =C(H)— | 0 |
| CHF₂CH₂S | H | CF₃O | H | H | =C(H)— | =C(H)— | 0 |
| MeHN | H | CF₃O | H | H | =C(H)— | =C(H)— | 0 |
| Me₂N | H | CF₃O | H | H | =C(H)— | =C(H)— | 0 |
| Me(iPr)N | H | CF₃O | H | H | =C(H)— | =C(H)— | 0 |
| CH₃C(O)NH | H | CF₃O | H | H | =C(H)— | =C(H)— | 0 |
| MeOC(O)NH | H | CF₃O | H | H | =C(H)— | =C(H)— | 0 |
| HC(O) | H | CF₃O | H | H | =C(H)— | =C(H)— | 0 |
| CH₃C(O) | H | CF₃O | H | H | =C(H)— | =C(H)— | 0 |
| HC(NOMe) | H | CF₃O | H | H | =C(H)— | =C(H)— | 0 |
| CH₃C(NOMe) | H | CF₃O | H | H | =C(H)— | =C(H)— | 0 |
| Ph | H | CF₃O | H | H | =C(H)— | =C(H)— | 0 |
| 2-Py | H | CF₃O | H | H | =C(H)— | =C(H)— | 0 |
| 3-Py | H | CF₃O | H | H | =C(H)— | =C(H)— | 0 |
| 4-Py | H | CF₃O | H | H | =C(H)— | =C(H)— | 0 |
| 1-Tz | H | CF₃O | H | H | =C(H)— | =C(H)— | 0 |
| 1-Pz | H | CF₃O | H | H | =C(H)— | =C(H)— | 0 |
| H | H | CF₃O | H | H | =C(H)— | =C(H)— | 1 |
| F | H | CF₃O | H | H | =C(H)— | =C(H)— | 1 |
| Cl | H | CF₃O | H | H | =C(H)— | =C(H)— | 1 |

TABLE 15

| R¹ | R² | R³ | R⁴ | R⁵ | A¹ | A² | n |
|---|---|---|---|---|---|---|---|
| Br | H | CF₃O | H | H | =C(H)— | =C(H)— | 1 |
| I | H | CF₃O | H | H | =C(H)— | =C(H)— | 1 |
| Me | H | CF₃O | H | H | =C(H)— | =C(H)— | 1 |
| Et | H | CF₃O | H | H | =C(H)— | =C(H)— | 1 |
| Pr | H | CF₃O | H | H | =C(H)— | =C(H)— | 1 |
| cPr | H | CF₃O | H | H | =C(H)— | =C(H)— | 1 |
| CF₃ | H | CF₃O | H | H | =C(H)— | =C(H)— | 1 |
| CH₃OCH₂ | H | CF₃O | H | H | =C(H)— | =C(H)— | 1 |
| MeO | H | CF₃O | H | H | =C(H)— | =C(H)— | 1 |
| EtO | H | CF₃O | H | H | =C(H)— | =C(H)— | 1 |
| PrO | H | CF₃O | H | H | =C(H)— | =C(H)— | 1 |
| CF₃CH₂O | H | CF₃O | H | H | =C(H)— | =C(H)— | 1 |
| CHF₂CH₂O | H | CF₃O | H | H | =C(H)— | =C(H)— | 1 |
| iPrO | H | CF₃O | H | H | =C(H)— | =C(H)— | 1 |
| Ph | H | CF₃O | H | H | =C(H)— | =C(H)— | 1 |
| H | H | CF₃S | H | H | =C(H)— | =C(H)— | 0 |
| F | H | CF₃S | H | H | =C(H)— | =C(H)— | 0 |
| Cl | H | CF₃S | H | H | =C(H)— | =C(H)— | 0 |
| Br | H | CF₃S | H | H | =C(H)— | =C(H)— | 0 |
| I | H | CF₃S | H | H | =C(H)— | =C(H)— | 0 |
| Me | H | CF₃S | H | H | =C(H)— | =C(H)— | 0 |
| Et | H | CF₃S | H | H | =C(H)— | =C(H)— | 0 |
| Pr | H | CF₃S | H | H | =C(H)— | =C(H)— | 0 |
| cPr | H | CF₃S | H | H | =C(H)— | =C(H)— | 0 |

TABLE 16

| R¹ | R² | R³ | R⁴ | R⁵ | A¹ | A² | n |
|---|---|---|---|---|---|---|---|
| CF₃ | H | CF₃S | H | H | =C(H)— | =C(H)— | 0 |
| CH₃OCH₂ | H | CF₃S | H | H | =C(H)— | =C(H)— | 0 |
| MeO | H | CF₃S | H | H | =C(H)— | =C(H)— | 0 |
| EtO | H | CF₃S | H | H | =C(H)— | =C(H)— | 0 |
| PrO | H | CF₃S | H | H | =C(H)— | =C(H)— | 0 |
| CF₃CH₂O | H | CF₃S | H | H | =C(H)— | =C(H)— | 0 |
| CHF₂CH₂O | H | CF₃S | H | H | =C(H)— | =C(H)— | 0 |
| iPrO | H | CF₃S | H | H | =C(H)— | =C(H)— | 0 |
| cPrCH₂O | H | CF₃S | H | H | =C(H)— | =C(H)— | 0 |
| cPenO | H | CF₃S | H | H | =C(H)— | =C(H)— | 0 |
| MeS | H | CF₃S | H | H | =C(H)— | =C(H)— | 0 |
| MeS(O) | H | CF₃S | H | H | =C(H)— | =C(H)— | 0 |
| MeS(O)₂ | H | CF₃S | H | H | =C(H)— | =C(H)— | 0 |
| EtS | H | CF₃S | H | H | =C(H)— | =C(H)— | 0 |
| EtS(O) | H | CF₃S | H | H | =C(H)— | =C(H)— | 0 |
| EtS(O)₂ | H | CF₃S | H | H | =C(H)— | =C(H)— | 0 |
| PrS | H | CF₃S | H | H | =C(H)— | =C(H)— | 0 |
| PrS(O) | H | CF₃S | H | H | =C(H)— | =C(H)— | 0 |
| PrS(O)₂ | H | CF₃S | H | H | =C(H)— | =C(H)— | 0 |
| iPrS | H | CF₃S | H | H | =C(H)— | =C(H)— | 0 |
| iPrS(O) | H | CF₃S | H | H | =C(H)— | =C(H)— | 0 |
| iPrS(O)₂ | H | CF₃S | H | H | =C(H)— | =C(H)— | 0 |
| CF₃CH₂S | H | CF₃S | H | H | =C(H)— | =C(H)— | 0 |
| CHF₂CH₂S | H | CF₃S | H | H | =C(H)— | =C(H)— | 0 |

TABLE 17

| R¹ | R² | R³ | R⁴ | R⁵ | A¹ | A² | n |
|---|---|---|---|---|---|---|---|
| MeHN | H | CF₃S | H | H | =C(H)— | =C(H)— | 0 |
| Me₂N | H | CF₃S | H | H | =C(H)— | =C(H)— | 0 |
| Me(iPr)N | H | CF₃S | H | H | =C(H)— | =C(H)— | 0 |
| CH₃C(O)NH | H | CF₃S | H | H | =C(H)— | =C(H)— | 0 |
| MeOC(O)NH | H | CF₃S | H | H | =C(H)— | =C(H)— | 0 |
| HC(O) | H | CF₃S | H | H | =C(H)— | =C(H)— | 0 |
| CH₃C(O) | H | CF₃S | H | H | =C(H)— | =C(H)— | 0 |
| HC(NOMe) | H | CF₃S | H | H | =C(H)— | =C(H)— | 0 |
| CH₃C(NOMe) | H | CF₃S | H | H | =C(H)— | =C(H)— | 0 |
| Ph | H | CF₃S | H | H | =C(H)— | =C(H)— | 0 |
| 2-Py | H | CF₃S | H | H | =C(H)— | =C(H)— | 0 |
| 3-Py | H | CF₃S | H | H | =C(H)— | =C(H)— | 0 |
| 4-Py | H | CF₃S | H | H | =C(H)— | =C(H)— | 0 |
| 1-Tz | H | CF₃S | H | H | =C(H)— | =C(H)— | 0 |
| 1-Pz | H | CF₃S | H | H | =C(H)— | =C(H)— | 0 |
| H | H | CF₃CF₂ | H | H | =C(H)— | =C(H)— | 0 |
| F | H | CF₃CF₂ | H | H | =C(H)— | =C(H)— | 0 |
| Cl | H | CF₃CF₂ | H | H | =C(H)— | =C(H)— | 0 |
| Br | H | CF₃CF₂ | H | H | =C(H)— | =C(H)— | 0 |
| I | H | CF₃CF₂ | H | H | =C(H)— | =C(H)— | 0 |
| Me | H | CF₃CF₂ | H | H | =C(H)— | =C(H)— | 0 |
| Et | H | CF₃CF₂ | H | H | =C(H)— | =C(H)— | 0 |
| Pr | H | CF₃CF₂ | H | H | =C(H)— | =C(H)— | 0 |
| cPr | H | CF₃CF₂ | H | H | =C(H)— | =C(H)— | 0 |

TABLE 18

| R¹ | R² | R³ | R⁴ | R⁵ | A¹ | A² | n |
|---|---|---|---|---|---|---|---|
| CF₃ | H | CF₃CF₂ | H | H | =C(H)— | =C(H)— | 0 |
| CH₃OCH₂ | H | CF₃CF₂ | H | H | =C(H)— | =C(H)— | 0 |
| MeO | H | CF₃CF₂ | H | H | =C(H)— | =C(H)— | 0 |
| EtO | H | CF₃CF₂ | H | H | =C(H)— | =C(H)— | 0 |
| PrO | H | CF₃CF₂ | H | H | =C(H)— | =C(H)— | 0 |
| CF₃CH₂O | H | CF₃CF₂ | H | H | =C(H)— | =C(H)— | 0 |
| CHF₂CH₂O | H | CF₃CF₂ | H | H | =C(H)— | =C(H)— | 0 |
| iPrO | H | CF₃CF₂ | H | H | =C(H)— | =C(H)— | 0 |
| cPrCH₂O | H | CF₃CF₂ | H | H | =C(H)— | =C(H)— | 0 |
| cPenO | H | CF₃CF₂ | H | H | =C(H)— | =C(H)— | 0 |
| MeS | H | CF₃CF₂ | H | H | =C(H)— | =C(H)— | 0 |
| MeS(O) | H | CF₃CF₂ | H | H | =C(H)— | =C(H)— | 0 |
| MeS(O)₂ | H | CF₃CF₂ | H | H | =C(H)— | =C(H)— | 0 |
| EtS | H | CF₃CF₂ | H | H | =C(H)— | =C(H)— | 0 |
| EtS(O) | H | CF₃CF₂ | H | H | =C(H)— | =C(H)— | 0 |
| EtS(O)₂ | H | CF₃CF₂ | H | H | =C(H)— | =C(H)— | 0 |
| PrS | H | CF₃CF₂ | H | H | =C(H)— | =C(H)— | 0 |
| PrS(O) | H | CF₃CF₂ | H | H | =C(H)— | =C(H)— | 0 |
| PrS(O)₂ | H | CF₃CF₂ | H | H | =C(H)— | =C(H)— | 0 |
| iPrS | H | CF₃CF₂ | H | H | =C(H)— | =C(H)— | 0 |
| iPrS(O) | H | CF₃CF₂ | H | H | =C(H)— | =C(H)— | 0 |
| iPrS(O)₂ | H | CF₃CF₂ | H | H | =C(H)— | =C(H)— | 0 |
| CF₃CH₂S | H | CF₃CF₂ | H | H | =C(H)— | =C(H)— | 0 |
| CHF₂CH₂S | H | CF₃CF₂ | H | H | =C(H)— | =C(H)— | 0 |

TABLE 19

| R¹ | R² | R³ | R⁴ | R⁵ | A¹ | A² | n |
|---|---|---|---|---|---|---|---|
| MeHN | H | CF₃CF₂ | H | H | =C(H)— | =C(H)— | 0 |
| Me₂N | H | CF₃CF₂ | H | H | =C(H)— | =C(H)— | 0 |
| Me(iPr)N | H | CF₃CF₂ | H | H | =C(H)— | =C(H)— | 0 |
| Ph | H | CF₃CF₂ | H | H | =C(H)— | =C(H)— | 0 |
| 2-Py | H | CF₃CF₂ | H | H | =C(H)— | =C(H)— | 0 |
| 3-Py | H | CF₃CF₂ | H | H | =C(H)— | =C(H)— | 0 |
| 4-Py | H | CF₃CF₂ | H | H | =C(H)— | =C(H)— | 0 |
| 1-Tz | H | CF₃CF₂ | H | H | =C(H)— | =C(H)— | 0 |
| 1-Pz | H | CF₃CF₂ | H | H | =C(H)— | =C(H)— | 0 |
| H | H | (CF₃)₂CF | H | H | =C(H)— | =C(H)— | 0 |
| F | H | (CF₃)₂CF | H | H | =C(H)— | =C(H)— | 0 |
| Cl | H | (CF₃)₂CF | H | H | =C(H)— | =C(H)— | 0 |
| Br | H | (CF₃)₂CF | H | H | =C(H)— | =C(H)— | 0 |
| I | H | (CF₃)₂CF | H | H | =C(H)— | =C(H)— | 0 |
| Me | H | (CF₃)₂CF | H | H | =C(H)— | =C(H)— | 0 |
| Et | H | (CF₃)₂CF | H | H | =C(H)— | =C(H)— | 0 |
| Pr | H | (CF₃)₂CF | H | H | =C(H)— | =C(H)— | 0 |
| cPr | H | (CF₃)₂CF | H | H | =C(H)— | =C(H)— | 0 |
| CF₃ | H | (CF₃)₂CF | H | H | =C(H)— | =C(H)— | 0 |
| CH₃OCH₂ | H | (CF₃)₂CF | H | H | =C(H)— | =C(H)— | 0 |
| MeO | H | (CF₃)₂CF | H | H | =C(H)— | =C(H)— | 0 |
| EtO | H | (CF₃)₂CF | H | H | =C(H)— | =C(H)— | 0 |
| PrO | H | (CF₃)₂CF | H | H | =C(H)— | =C(H)— | 0 |
| CF₃CH₂O | H | (CF₃)₂CF | H | H | =C(H)— | =C(H)— | 0 |

TABLE 20

| R¹ | R² | R³ | R⁴ | R⁵ | A¹ | A² | n |
|---|---|---|---|---|---|---|---|
| CHF₂CH₂O | H | (CF₃)₂CF | H | H | =C(H)— | =C(H)— | 0 |
| iPrO | H | (CF₃)₂CF | H | H | =C(H)— | =C(H)— | 0 |
| cPrCH₂O | H | (CF₃)₂CF | H | H | =C(H)— | =C(H)— | 0 |
| cPenO | H | (CF₃)₂CF | H | H | =C(H)— | =C(H)— | 0 |
| MeS | H | (CF₃)₂CF | H | H | =C(H)— | =C(H)— | 0 |
| MeS(O) | H | (CF₃)₂CF | H | H | =C(H)— | =C(H)— | 0 |
| MeS(O)₂ | H | (CF₃)₂CF | H | H | =C(H)— | =C(H)— | 0 |
| EtS | H | (CF₃)₂CF | H | H | =C(H)— | =C(H)— | 0 |
| EtS(O) | H | (CF₃)₂CF | H | H | =C(H)— | =C(H)— | 0 |
| EtS(O)₂ | H | (CF₃)₂CF | H | H | =C(H)— | =C(H)— | 0 |
| PrS | H | (CF₃)₂CF | H | H | =C(H)— | =C(H)— | 0 |
| PrS(O) | H | (CF₃)₂CF | H | H | =C(H)— | =C(H)— | 0 |
| PrS(O)₂ | H | (CF₃)₂CF | H | H | =C(H)— | =C(H)— | 0 |
| iPrS | H | (CF₃)₂CF | H | H | =C(H)— | =C(H)— | 0 |
| iPrS(O) | H | (CF₃)₂CF | H | H | =C(H)— | =C(H)— | 0 |
| iPrS(O)₂ | H | (CF₃)₂CF | H | H | =C(H)— | =C(H)— | 0 |
| CF₃CH₂S | H | (CF₃)₂CF | H | H | =C(H)— | =C(H)— | 0 |
| CHF₂CH₂S | H | (CF₃)₂CF | H | H | =C(H)— | =C(H)— | 0 |
| MeHN | H | (CF₃)₂CF | H | H | =C(H)— | =C(H)— | 0 |
| Me₂N | H | (CF₃)₂CF | H | H | =C(H)— | =C(H)— | 0 |
| Me(iPr)N | H | (CF₃)₂CF | H | H | =C(H)— | =C(H)— | 0 |
| Ph | H | (CF₃)₂CF | H | H | =C(H)— | =C(H)— | 0 |
| 2-Py | H | (CF₃)₂CF | H | H | =C(H)— | =C(H)— | 0 |
| 3-Py | H | (CF₃)₂CF | H | H | =C(H)— | =C(H)— | 0 |

TABLE 21

| R¹ | R² | R³ | R⁴ | R⁵ | A¹ | A² | n |
|---|---|---|---|---|---|---|---|
| 4-Py | H | (CF₃)₂CF | H | H | =C(H)— | =C(H)— | 0 |
| 1-Tz | H | (CF₃)₂CF | H | H | =C(H)— | =C(H)— | 0 |
| 1-Pz | H | (CF₃)₂CF | H | H | =C(H)— | =C(H)— | 0 |
| H | H | CF₃ | H | H | =C(H)— | N | 0 |
| F | H | CF₃ | H | H | =C(H)— | N | 0 |
| Cl | H | CF₃ | H | H | =C(H)— | N | 0 |
| Br | H | CF₃ | H | H | =C(H)— | N | 0 |
| I | H | CF₃ | H | H | =C(H)— | N | 0 |
| Me | H | CF₃ | H | H | =C(H)— | N | 0 |
| Et | H | CF₃ | H | H | =C(H)— | N | 0 |
| Pr | H | CF₃ | H | H | =C(H)— | N | 0 |
| cPr | H | CF₃ | H | H | =C(H)— | N | 0 |
| CF₃ | H | CF₃ | H | H | =C(H)— | N | 0 |
| CH₃OCH₂ | H | CF₃ | H | H | =C(H)— | N | 0 |
| MeO | H | CF₃ | H | H | =C(H)— | N | 0 |
| EtO | H | CF₃ | H | H | =C(H)— | N | 0 |
| PrO | H | CF₃ | H | H | =C(H)— | N | 0 |
| CF₃CH₂O | H | CF₃ | H | H | =C(H)— | N | 0 |
| CHF₂CH₂O | H | CF₃ | H | H | =C(H)— | N | 0 |
| iPrO | H | CF₃ | H | H | =C(H)— | N | 0 |
| cPrCH₂O | H | CF₃ | H | H | =C(H)— | N | 0 |
| cPenO | H | CF₃ | H | H | =C(H)— | N | 0 |
| MeS | H | CF₃ | H | H | =C(H)— | N | 0 |
| MeS(O) | H | CF₃ | H | H | =C(H)— | N | 0 |

TABLE 22

| R¹ | R² | R³ | R⁴ | R⁵ | A¹ | A² | n |
|---|---|---|---|---|---|---|---|
| MeS(O)₂ | H | CF₃ | H | H | =C(H)— | N | 0 |
| EtS | H | CF₃ | H | H | =C(H)— | N | 0 |
| EtS(O) | H | CF₃ | H | H | =C(H)— | N | 0 |
| EtS(O)₂ | H | CF₃ | H | H | =C(H)— | N | 0 |
| PrS | H | CF₃ | H | H | =C(H)— | N | 0 |
| PrS(O) | H | CF₃ | H | H | =C(H)— | N | 0 |
| PrS(O)₂ | H | CF₃ | H | H | =C(H)— | N | 0 |
| iPrS | H | CF₃ | H | H | =C(H)— | N | 0 |
| iPrS(O) | H | CF₃ | H | H | =C(H)— | N | 0 |
| iPrS(O)₂ | H | CF₃ | H | H | =C(H)— | N | 0 |
| CF₃CH₂S | H | CF₃ | H | H | =C(H)— | N | 0 |
| CHF₂CH₂S | H | CF₃ | H | H | =C(H)— | N | 0 |
| MeHN | H | CF₃ | H | H | =C(H)— | N | 0 |
| Me₂N | H | CF₃ | H | H | =C(H)— | N | 0 |
| Me(iPr)N | H | CF₃ | H | H | =C(H)— | N | 0 |
| CH₃C(O)NH | H | CF₃ | H | H | =C(H)— | N | 0 |
| MeOC(O)NH | H | CF₃ | H | H | =C(H)— | N | 0 |
| HC(O) | H | CF₃ | H | H | =C(H)— | N | 0 |
| CH₃C(O) | H | CF₃ | H | H | =C(H)— | N | 0 |
| HC(NOMe) | H | CF₃ | H | H | =C(H)— | N | 0 |
| CH₃C(NOMe) | H | CF₃ | H | H | =C(H)— | N | 0 |
| Ph | H | CF₃ | H | H | =C(H)— | N | 0 |
| 2-Py | H | CF₃ | H | H | =C(H)— | N | 0 |
| 3-Py | H | CF₃ | H | H | =C(H)— | N | 0 |

TABLE 23

| R¹ | R² | R³ | R⁴ | R⁵ | A¹ | A² | n |
|---|---|---|---|---|---|---|---|
| 4-Py | H | CF₃ | H | H | =C(H)— | N | 0 |
| 1-Tz | H | CF₃ | H | H | =C(H)— | N | 0 |
| 1-Pz | H | CF₃ | H | H | =C(H)— | N | 0 |
| H | H | CF₃ | H | H | =C(H)— | N | 1 |
| F | H | CF₃ | H | H | =C(H)— | N | 1 |
| Cl | H | CF₃ | H | H | =C(H)— | N | 1 |
| Br | H | CF₃ | H | H | =C(H)— | N | 1 |
| I | H | CF₃ | H | H | =C(H)— | N | 1 |
| Me | H | CF₃ | H | H | =C(H)— | N | 1 |
| Et | H | CF₃ | H | H | =C(H)— | N | 1 |
| Pr | H | CF₃ | H | H | =C(H)— | N | 1 |
| cPr | H | CF₃ | H | H | =C(H)— | N | 1 |
| CF₃ | H | CF₃ | H | H | =C(H)— | N | 1 |
| CH₃OCH₂ | H | CF₃ | H | H | =C(H)— | N | 1 |
| MeO | H | CF₃ | H | H | =C(H)— | N | 1 |

TABLE 23-continued

| R¹ | R² | R³ | R⁴ | R⁵ | A¹ | A² | n |
|---|---|---|---|---|---|---|---|
| EtO | H | CF₃ | H | H | =C(H)— | N | 1 |
| PrO | H | CF₃ | H | H | =C(H)— | N | 1 |
| CF₃CH₂O | H | CF₃ | H | H | =C(H)— | N | 1 |
| CHF₂CH₂O | H | CF₃ | H | H | =C(H)— | N | 1 |
| iPrO | H | CF₃ | H | H | =C(H)— | N | 1 |
| Ph | H | CF₃ | H | H | =C(H)— | N | 1 |
| H | H | CF₃ | H | H | N | =C(H)— | 0 |
| F | H | CF₃ | H | H | N | =C(H)— | 0 |
| Cl | H | CF₃ | H | H | N | =C(H)— | 0 |

TABLE 24

| R¹ | R² | R³ | R⁴ | R⁵ | A¹ | A² | n |
|---|---|---|---|---|---|---|---|
| Br | H | CF₃ | H | H | N | =C(H)— | 0 |
| I | H | CF₃ | H | H | N | =C(H)— | 0 |
| Me | H | CF₃ | H | H | N | =C(H)— | 0 |
| Et | H | CF₃ | H | H | N | =C(H)— | 0 |
| Pr | H | CF₃ | H | H | N | =C(H)— | 0 |
| cPr | H | CF₃ | H | H | N | =C(H)— | 0 |
| CF₃ | H | CF₃ | H | H | N | =C(H)— | 0 |
| CH₃OCH₂ | H | CF₃ | H | H | N | =C(H)— | 0 |
| MeO | H | CF₃ | H | H | N | =C(H)— | 0 |
| EtO | H | CF₃ | H | H | N | =C(H)— | 0 |
| PrO | H | CF₃ | H | H | N | =C(H)— | 0 |
| CF₃CH₂O | H | CF₃ | H | H | N | =C(H)— | 0 |
| CHF₂CH₂O | H | CF₃ | H | H | N | =C(H)— | 0 |
| iPrO | H | CF₃ | H | H | N | =C(H)— | 0 |
| cPrCH₂O | H | CF₃ | H | H | N | =C(H)— | 0 |
| cPenO | H | CF₃ | H | H | N | =C(H)— | 0 |
| MeS | H | CF₃ | H | H | N | =C(H)— | 0 |
| MeS(O) | H | CF₃ | H | H | N | =C(H)— | 0 |
| MeS(O)₂ | H | CF₃ | H | H | N | =C(H)— | 0 |
| EtS | H | CF₃ | H | H | N | =C(H)— | 0 |
| EtS(O) | H | CF₃ | H | H | N | =C(H)— | 0 |
| EtS(O)₂ | H | CF₃ | H | H | N | =C(H)— | 0 |
| PrS | H | CF₃ | H | H | N | =C(H)— | 0 |
| PrS(O) | H | CF₃ | H | H | N | =C(H)— | 0 |

TABLE 25

| R¹ | R² | R³ | R⁴ | R⁵ | A¹ | A² | n |
|---|---|---|---|---|---|---|---|
| PrS(O)₂ | H | CF₃ | H | H | N | =C(H)— | 0 |
| iPrS | H | CF₃ | H | H | N | =C(H)— | 0 |
| iPrS(O) | H | CF₃ | H | H | N | =C(H)— | 0 |
| iPrS(O)₂ | H | CF₃ | H | H | N | =C(H)— | 0 |
| CF₃CH₂S | H | CF₃ | H | H | N | =C(H)— | 0 |
| CHF₂CH₂S | H | CF₃ | H | H | N | =C(H)— | 0 |
| MeHN | H | CF₃ | H | H | N | =C(H)— | 0 |
| Me₂N | H | CF₃ | H | H | N | =C(H)— | 0 |
| Me(iPr)N | H | CF₃ | H | H | N | =C(H)— | 0 |
| CH₃C(O)NH | H | CF₃ | H | H | N | =C(H)— | 0 |
| Ph | H | CF₃ | H | H | N | =C(H)— | 0 |
| 2-Py | H | CF₃ | H | H | N | =C(H)— | 0 |
| 3-Py | H | CF₃ | H | H | N | =C(H)— | 0 |
| 4-Py | H | CF₃ | H | H | N | =C(H)— | 0 |
| 1-Tz | H | CF₃ | H | H | N | =C(H)— | 0 |
| 1-Pz | H | CF₃ | H | H | N | =C(H)— | 0 |
| H | H | —CF₂OCF₂— | | H | =C(H)— | =C(H)— | 0 |
| F | H | —CF₂OCF₂— | | H | =C(H)— | =C(H)— | 0 |
| Cl | H | —CF₂OCF₂— | | H | =C(H)— | =C(H)— | 0 |
| Br | H | —CF₂OCF₂— | | H | =C(H)— | =C(H)— | 0 |
| I | H | —CF₂OCF₂— | | H | =C(H)— | =C(H)— | 0 |
| Me | H | —CF₂OCF₂— | | H | =C(H)— | =C(H)— | 0 |
| Et | H | —CF₂OCF₂— | | H | =C(H)— | =C(H)— | 0 |
| Pr | H | —CF₂OCF₂— | | H | =C(H)— | =C(H)— | 0 |

TABLE 26

| R¹ | R² | R³ | R⁴ | R⁵ | A¹ | A² | n |
|---|---|---|---|---|---|---|---|
| cPr | H | —CF₂OCF₂— | H | =C(H)— | =C(H)— | 0 |
| CF₃ | H | —CF₂OCF₂— | H | =C(H)— | =C(H)— | 0 |
| CH₃OCH₂ | H | —CF₂OCF₂— | H | =C(H)— | =C(H)— | 0 |
| MeO | H | —CF₂OCF₂— | H | =C(H)— | =C(H)— | 0 |
| EtO | H | —CF₂OCF₂— | H | =C(H)— | =C(H)— | 0 |
| PrO | H | —CF₂OCF₂— | H | =C(H)— | =C(H)— | 0 |
| CF₃CH₂O | H | —CF₂OCF₂— | H | =C(H)— | =C(H)— | 0 |
| CHF₂CH₂O | H | —CF₂OCF₂— | H | =C(H)— | =C(H)— | 0 |
| iPrO | H | —CF₂OCF₂— | H | =C(H)— | =C(H)— | 0 |
| cPrCH₂O | H | —CF₂OCF₂— | H | =C(H)— | =C(H)— | 0 |
| cPenO | H | —CF₂OCF₂— | H | =C(H)— | =C(H)— | 0 |
| MeS | H | —CF₂OCF₂— | H | =C(H)— | =C(H)— | 0 |
| MeS(O) | H | —CF₂OCF₂— | H | =C(H)— | =C(H)— | 0 |
| MeS(O)₂ | H | —CF₂OCF₂— | H | =C(H)— | =C(H)— | 0 |
| EtS | H | —CF₂OCF₂— | H | =C(H)— | =C(H)— | 0 |
| EtS(O) | H | —CF₂OCF₂— | H | =C(H)— | =C(H)— | 0 |
| EtS(O)₂ | H | —CF₂OCF₂— | H | =C(H)— | =C(H)— | 0 |
| PrS | H | —CF₂OCF₂— | H | =C(H)— | =C(H)— | 0 |
| PrS(O) | H | —CF₂OCF₂— | H | =C(H)— | =C(H)— | 0 |
| PrS(O)₂ | H | —CF₂OCF₂— | H | =C(H)— | =C(H)— | 0 |
| iPrS | H | —CF₂OCF₂— | H | =C(H)— | =C(H)— | 0 |
| iPrS(O) | H | —CF₂OCF₂— | H | =C(H)— | =C(H)— | 0 |
| iPrS(O)₂ | H | —CF₂OCF₂— | H | =C(H)— | =C(H)— | 0 |
| CF₃CH₂S | H | —CF₂OCF₂— | H | =C(H)— | =C(H)— | 0 |

TABLE 27

| R¹ | R² | R³ | R⁴ | R⁵ | A¹ | A² | n |
|---|---|---|---|---|---|---|---|
| CHF₂CH₂S | H | —CF₂OCF₂— | H | =C(H)— | =C(H)— | 0 |
| MeHN | H | —CF₂OCF₂— | H | =C(H)— | =C(H)— | 0 |
| Me₂N | H | —CF₂OCF₂— | H | =C(H)— | =C(H)— | 0 |
| Me(iPr)N | H | —CF₂OCF₂— | H | =C(H)— | =C(H)— | 0 |
| CH₃C(O)NH | H | —CF₂OCF₂— | H | =C(H)— | =C(H)— | 0 |
| Ph | H | —CF₂OCF₂— | H | =C(H)— | =C(H)— | 0 |
| 2-Py | H | —CF₂OCF₂— | H | =C(H)— | =C(H)— | 0 |
| 3-Py | H | —CF₂OCF₂— | H | =C(H)— | =C(H)— | 0 |
| 4-Py | H | —CF₂OCF₂— | H | =C(H)— | =C(H)— | 0 |
| 1-Tz | H | —CF₂OCF₂— | H | =C(H)— | =C(H)— | 0 |
| 1-Pz | H | —CF₂OCF₂— | H | =C(H)— | =C(H)— | 0 |
| H | H | —CF₂CH₂CH₂— | H | =C(H)— | =C(H)— | 0 |
| F | H | —CF₂CH₂CH₂— | H | =C(H)— | =C(H)— | 0 |
| Cl | H | —CF₂CH₂CH₂— | H | =C(H)— | =C(H)— | 0 |
| Br | H | —CF₂CH₂CH₂— | H | =C(H)— | =C(H)— | 0 |
| I | H | —CF₂CH₂CH₂— | H | =C(H)— | =C(H)— | 0 |
| Me | H | —CF₂CH₂CH₂— | H | =C(H)— | =C(H)— | 0 |
| Et | H | —CF₂CH₂CH₂— | H | =C(H)— | =C(H)— | 0 |
| Pr | H | —CF₂CH₂CH₂— | H | =C(H)— | =C(H)— | 0 |
| cPr | H | —CF₂CH₂CH₂— | H | =C(H)— | =C(H)— | 0 |
| CF₃ | H | —CF₂CH₂CH₂— | H | =C(H)— | =C(H)— | 0 |
| CH₃OCH₂ | H | —CF₂CH₂CH₂— | H | =C(H)— | =C(H)— | 0 |
| MeO | H | —CF₂CH₂CH₂— | H | =C(H)— | =C(H)— | 0 |
| EtO | H | —CF₂CH₂CH₂— | H | =C(H)— | =C(H)— | 0 |

TABLE 28

| R¹ | R² | R³ | R⁴ | R⁵ | A¹ | A² | n |
|---|---|---|---|---|---|---|---|
| PrO | H | —CF₂CH₂CH₂— | H | =C(H)— | =C(H)— | 0 |
| CF₃CH₂O | H | —CF₂CH₂CH₂— | H | =C(H)— | =C(H)— | 0 |
| CHF₂CH₂O | H | —CF₂CH₂CH₂— | H | =C(H)— | =C(H)— | 0 |
| iPrO | H | —CF₂CH₂CH₂— | H | =C(H)— | =C(H)— | 0 |
| cPrCH₂O | H | —CF₂CH₂CH₂— | H | =C(H)— | =C(H)— | 0 |
| cPenO | H | —CF₂CH₂CH₂— | H | =C(H)— | =C(H)— | 0 |
| MeS | H | —CF₂CH₂CH₂— | H | =C(H)— | =C(H)— | 0 |
| MeS(O) | H | —CF₂CH₂CH₂— | H | =C(H)— | =C(H)— | 0 |
| MeS(O)₂ | H | —CF₂CH₂CH₂— | H | =C(H)— | =C(H)— | 0 |
| EtS | H | —CF₂CH₂CH₂— | H | =C(H)— | =C(H)— | 0 |
| EtS(O) | H | —CF₂CH₂CH₂— | H | =C(H)— | =C(H)— | 0 |
| EtS(O)₂ | H | —CF₂CH₂CH₂— | H | =C(H)— | =C(H)— | 0 |
| PrS | H | —CF₂CH₂CH₂— | H | =C(H)— | =C(H)— | 0 |
| PrS(O) | H | —CF₂CH₂CH₂— | H | =C(H)— | =C(H)— | 0 |
| PrS(O)₂ | H | —CF₂CH₂CH₂— | H | =C(H)— | =C(H)— | 0 |
| iPrS | H | —CF₂CH₂CH₂— | H | =C(H)— | =C(H)— | 0 |
| iPrS(O) | H | —CH₂CH₂CF₂— | H | =C(H)— | =C(H)— | 0 |
| iPrS(O)₂ | H | —CH₂CH₂CF₂— | H | =C(H)— | =C(H)— | 0 |
| CF₃CH₂S | H | —CH₂CH₂CF₂— | H | =C(H)— | =C(H)— | 0 |
| CHF₂CH₂S | H | —CH₂CH₂CF₂— | H | =C(H)— | =C(H)— | 0 |
| MeHN | H | —CH₂CH₂CF₂— | H | =C(H)— | =C(H)— | 0 |
| Me₂N | H | —CH₂CH₂CF₂— | H | =C(H)— | =C(H)— | 0 |
| Me(iPr)N | H | —CH₂CH₂CF₂— | H | =C(H)— | =C(H)— | 0 |
| H | H | —CF₂CH₂CH₂CH₂— | H | =C(H)— | =C(H)— | 0 |

TABLE 29

| R¹ | R² | R³ | R⁴ | R⁵ | A¹ | A² | n |
|---|---|---|---|---|---|---|---|
| F | H | —CF₂CH₂CH₂CH₂— | H | =C(H)— | =C(H)— | 0 |
| Cl | H | —CF₂CH₂CH₂CH₂— | H | =C(H)— | =C(H)— | 0 |
| Br | H | —CF₂CH₂CH₂CH₂— | H | =C(H)— | =C(H)— | 0 |
| I | H | —CF₂CH₂CH₂CH₂— | H | =C(H)— | =C(H)— | 0 |
| Me | H | —CF₂CH₂CH₂CH₂— | H | =C(H)— | =C(H)— | 0 |
| Et | H | —CF₂CH₂CH₂CH₂— | H | =C(H)— | =C(H)— | 0 |
| Pr | H | —CF₂CH₂CH₂CH₂— | H | =C(H)— | =C(H)— | 0 |
| cPr | H | —CF₂CH₂CH₂CH₂— | H | =C(H)— | =C(H)— | 0 |
| CF₃ | H | —CF₂CH₂CH₂CH₂— | H | =C(H)— | =C(H)— | 0 |
| CH₃OCH₂ | H | —CF₂CH₂CH₂CH₂— | H | =C(H)— | =C(H)— | 0 |
| MeO | H | —CF₂CH₂CH₂CH₂— | H | =C(H)— | =C(H)— | 0 |
| EtO | H | —CF₂CH₂CH₂CH₂— | H | =C(H)— | =C(H)— | 0 |
| PrO | H | —CF₂CH₂CH₂CH₂— | H | =C(H)— | =C(H)— | 0 |
| CF₃CH₂O | H | —CF₂CH₂CH₂CH₂— | H | =C(H)— | =C(H)— | 0 |
| CHF₂CH₂O | H | —CF₂CH₂CH₂CH₂— | H | =C(H)— | =C(H)— | 0 |

TABLE 29-continued

| R¹ | R² | R³ | R⁴ | R⁵ | A¹ | A² | n |
|---|---|---|---|---|---|---|---|
| iPrO | H |  | —CF₂CH₂CH₂CH₂— | H | =C(H)— | =C(H)— | 0 |
| cPrCH₂O | H |  | —CF₂CH₂CH₂CH₂— | H | =C(H)— | =C(H)— | 0 |
| cPenO | H |  | —CF₂CH₂CH₂CH₂— | H | =C(H)— | =C(H)— | 0 |
| MeS | H |  | —CF₂CH₂CH₂CH₂— | H | =C(H)— | =C(H)— | 0 |
| MeS(O) | H |  | —CF₂CH₂CH₂CH₂— | H | =C(H)— | =C(H)— | 0 |
| MeS(O)₂ | H |  | —CF₂CH₂CH₂CH₂— | H | =C(H)— | =C(H)— | 0 |
| EtS | H |  | —CF₂CH₂CH₂CH₂— | H | =C(H)— | =C(H)— | 0 |
| EtS(O) | H |  | —CF₂CH₂CH₂CH₂— | H | =C(H)— | =C(H)— | 0 |
| EtS(O)₂ | H |  | —CF₂CH₂CH₂CH₂— | H | =C(H)— | =C(H)— | 0 |

TABLE 30

| R¹ | R² | R³ | R⁴ | R⁵ | A¹ | A² | n |
|---|---|---|---|---|---|---|---|
| PrS | H |  | —CF₂CH₂CH₂CH₂— | H | =C(H)— | =C(H)— | 0 |
| PrS(O) | H |  | —CF₂CH₂CH₂CH₂— | H | =C(H)— | =C(H)— | 0 |
| PrS(O)₂ | H |  | —CF₂CH₂CH₂CH₂— | H | =C(H)— | =C(H)— | 0 |
| iPrS | H |  | —CF₂CH₂CH₂CH₂— | H | =C(H)— | =C(H)— | 0 |
| iPrS(O) | H |  | —CF₂CH₂CH₂CH₂— | H | =C(H)— | =C(H)— | 0 |
| iPrS(O)₂ | H |  | —CF₂CH₂CH₂CH₂— | H | =C(H)— | =C(H)— | 0 |
| CF₃CH₂S | H |  | —CF₂CH₂CH₂CH₂— | H | =C(H)— | =C(H)— | 0 |
| CHF₂CH₂S | H |  | —CF₂CH₂CH₂CH₂— | H | =C(H)— | =C(H)— | 0 |
| MeHN | H |  | —CF₂CH₂CH₂CH₂— | H | =C(H)— | =C(H)— | 0 |
| Me₂N | H |  | —CF₂CH₂CH₂CH₂— | H | =C(H)— | =C(H)— | 0 |
| Me(iPr)N | H |  | —CF₂CH₂CH₂CH₂— | H | =C(H)— | =C(H)— | 0 |
| H | H |  | —CF₂CH₂CH₂O— | H | =C(H)— | =C(H)— | 0 |
| F | H |  | —CF₂CH₂CH₂O— | H | =C(H)— | =C(H)— | 0 |
| Cl | H |  | —CF₂CH₂CH₂O— | H | =C(H)— | =C(H)— | 0 |
| Br | H |  | —CF₂CH₂CH₂O— | H | =C(H)— | =C(H)— | 0 |
| I | H |  | —CF₂CH₂CH₂O— | H | =C(H)— | =C(H)— | 0 |
| Me | H |  | —CF₂CH₂CH₂O— | H | =C(H)— | =C(H)— | 0 |
| Et | H |  | —CF₂CH₂CH₂O— | H | =C(H)— | =C(H)— | 0 |
| Pr | H |  | —CF₂CH₂CH₂O— | H | =C(H)— | =C(H)— | 0 |
| cPr | H |  | —CF₂CH₂CH₂O— | H | =C(H)— | =C(H)— | 0 |
| CF₃ | H |  | —CF₂CH₂CH₂O— | H | =C(H)— | =C(H)— | 0 |
| CH₃OCH₂ | H |  | —CF₂CH₂CH₂O— | H | =C(H)— | =C(H)— | 0 |
| MeO | H |  | —CF₂CH₂CH₂O— | H | =C(H)— | =C(H)— | 0 |
| EtO | H |  | —CF₂CH₂CH₂O— | H | =C(H)— | =C(H)— | 0 |

TABLE 31

| R¹ | R² | R³ | R⁴ | R⁵ | A¹ | A² | n |
|---|---|---|---|---|---|---|---|
| PrO | H |  | —CF₂CH₂CH₂O— | H | =C(H)— | =C(H)— | 0 |
| CF₃CH₂O | H |  | —CF₂CH₂CH₂O— | H | =C(H)— | =C(H)— | 0 |
| CHF₂CH₂O | H |  | —CF₂CH₂CH₂O— | H | =C(H)— | =C(H)— | 0 |
| iPrO | H |  | —CF₂CH₂CH₂O— | H | =C(H)— | =C(H)— | 0 |
| cPrCH₂O | H |  | —CF₂CH₂CH₂O— | H | =C(H)— | =C(H)— | 0 |
| cPenO | H |  | —CF₂CH₂CH₂O— | H | =C(H)— | =C(H)— | 0 |
| MeS | H |  | —CF₂CH₂CH₂O— | H | =C(H)— | =C(H)— | 0 |
| MeS(O) | H |  | —CF₂CH₂CH₂O— | H | =C(H)— | =C(H)— | 0 |
| MeS(O)₂ | H |  | —CF₂CH₂CH₂O— | H | =C(H)— | =C(H)— | 0 |
| EtS | H |  | —CF₂CH₂CH₂O— | H | =C(H)— | =C(H)— | 0 |
| EtS(O) | H |  | —CF₂CH₂CH₂O— | H | =C(H)— | =C(H)— | 0 |
| EtS(O)₂ | H |  | —CF₂CH₂CH₂O— | H | =C(H)— | =C(H)— | 0 |
| PrS | H |  | —CF₂CH₂CH₂O— | H | =C(H)— | =C(H)— | 0 |
| PrS(O) | H |  | —CF₂CH₂CH₂O— | H | =C(H)— | =C(H)— | 0 |
| PrS(O)₂ | H |  | —CF₂CH₂CH₂O— | H | =C(H)— | =C(H)— | 0 |
| iPrS | H |  | —CF₂CH₂CH₂O— | H | =C(H)— | =C(H)— | 0 |
| iPrS(O) | H |  | —CF₂CH₂CH₂O— | H | =C(H)— | =C(H)— | 0 |
| iPrS(O)₂ | H |  | —CF₂CH₂CH₂O— | H | =C(H)— | =C(H)— | 0 |
| CF₃CH₂S | H |  | —CF₂CH₂CH₂O— | H | =C(H)— | =C(H)— | 0 |
| CHF₂CH₂S | H |  | —CF₂CH₂CH₂O— | H | =C(H)— | =C(H)— | 0 |
| MeHN | H |  | —CF₂CH₂CH₂O— | H | =C(H)— | =C(H)— | 0 |
| Me₂N | H |  | —CF₂CH₂CH₂O— | H | =C(H)— | =C(H)— | 0 |
| Me(iPr)N | H |  | —CF₂CH₂CH₂O— | H | =C(H)— | =C(H)— | 0 |
| H | H | H | CF₃ | H | =C(H)— | =C(H)— | 0 |

TABLE 32

| R¹ | R² | R³ | R⁴ | R⁵ | A¹ | A² | n |
|---|---|---|---|---|---|---|---|
| F | H | H | CF₃ | H | =C(H)— | =C(H)— | 0 |
| Cl | H | H | CF₃ | H | =C(H)— | =C(H)— | 0 |
| Br | H | H | CF₃ | H | =C(H)— | =C(H)— | 0 |
| I | H | H | CF₃ | H | =C(H)— | =C(H)— | 0 |
| Me | H | H | CF₃ | H | =C(H)— | =C(H)— | 0 |
| Et | H | H | CF₃ | H | =C(H)— | =C(H)— | 0 |
| Pr | H | H | CF₃ | H | =C(H)— | =C(H)— | 0 |
| cPr | H | H | CF₃ | H | =C(H)— | =C(H)— | 0 |
| CF₃ | H | H | CF₃ | H | =C(H)— | =C(H)— | 0 |
| CH₃OCH₂ | H | H | CF₃ | H | =C(H)— | =C(H)— | 0 |
| MeO | H | H | CF₃ | H | =C(H)— | =C(H)— | 0 |
| EtO | H | H | CF₃ | H | =C(H)— | =C(H)— | 0 |
| PrO | H | H | CF₃ | H | =C(H)— | =C(H)— | 0 |
| CF₃CH₂O | H | H | CF₃ | H | =C(H)— | =C(H)— | 0 |
| CHF₂CH₂O | H | H | CF₃ | H | =C(H)— | =C(H)— | 0 |
| iPrO | H | H | CF₃ | H | =C(H)— | =C(H)— | 0 |
| cPrCH₂O | H | H | CF₃ | H | =C(H)— | =C(H)— | 0 |
| cPenO | H | H | CF₃ | H | =C(H)— | =C(H)— | 0 |
| MeS | H | H | CF₃ | H | =C(H)— | =C(H)— | 0 |
| MeS(O) | H | H | CF₃ | H | =C(H)— | =C(H)— | 0 |
| MeS(O)₂ | H | H | CF₃ | H | =C(H)— | =C(H)— | 0 |
| EtS | H | H | CF₃ | H | =C(H)— | =C(H)— | 0 |
| EtS(O) | H | H | CF₃ | H | =C(H)— | =C(H)— | 0 |
| EtS(O)₂ | H | H | CF₃ | H | =C(H)— | =C(H)— | 0 |

TABLE 33

| R¹ | R² | R³ | R⁴ | R⁵ | A¹ | A² | n |
|---|---|---|---|---|---|---|---|
| PrS | H | H | CF₃ | H | =C(H)— | =C(H)— | 0 |
| PrS(O) | H | H | CF₃ | H | =C(H)— | =C(H)— | 0 |
| PrS(O)₂ | H | H | CF₃ | H | =C(H)— | =C(H)— | 0 |
| iPrS | H | H | CF₃ | H | =C(H)— | =C(H)— | 0 |
| iPrS(O) | H | H | CF₃ | H | =C(H)— | =C(H)— | 0 |
| iPrS(O)₂ | H | H | CF₃ | H | =C(H)— | =C(H)— | 0 |
| CF₃CH₂S | H | H | CF₃ | H | =C(H)— | =C(H)— | 0 |
| CHF₂CH₂S | H | H | CF₃ | H | =C(H)— | =C(H)— | 0 |
| MeHN | H | H | CF₃ | H | =C(H)— | =C(H)— | 0 |
| Me₂N | H | H | CF₃ | H | =C(H)— | =C(H)— | 0 |
| Me(iPr)N | H | H | CF₃ | H | =C(H)— | =C(H)— | 0 |
| CH₃C(O)NH | H | H | CF₃ | H | =C(H)— | =C(H)— | 0 |
| MeOC(O)NH | H | H | CF₃ | H | =C(H)— | =C(H)— | 0 |
| HC(O) | H | H | CF₃ | H | =C(H)— | =C(H)— | 0 |
| CH₃C(O) | H | H | CF₃ | H | =C(H)— | =C(H)— | 0 |
| HC(NOMe) | H | H | CF₃ | H | =C(H)— | =C(H)— | 0 |
| CH₃C(NOMe) | H | H | CF₃ | H | =C(H)— | =C(H)— | 0 |
| Ph | H | H | CF₃ | H | =C(H)— | =C(H)— | 0 |
| 2-Py | H | H | CF₃ | H | =C(H)— | =C(H)— | 0 |
| 3-Py | H | H | CF₃ | H | =C(H)— | =C(H)— | 0 |
| 4-Py | H | H | CF₃ | H | =C(H)— | =C(H)— | 0 |
| 1-Tz | H | H | CF₃ | H | =C(H)— | =C(H)— | 0 |
| 1-Pz | H | H | CF₃ | H | =C(H)— | =C(H)— | 0 |
| H | H | H | CF₃ | H | =C(H)— | =C(H)— | 1 |

TABLE 34

| R¹ | R² | R³ | R⁴ | R⁵ | A¹ | A² | n |
|---|---|---|---|---|---|---|---|
| F | H | H | CF₃ | H | =C(H)— | =C(H)— | 1 |
| Cl | H | H | CF₃ | H | =C(H)— | =C(H)— | 1 |
| Br | H | H | CF₃ | H | =C(H)— | =C(H)— | 1 |
| I | H | H | CF₃ | H | =C(H)— | =C(H)— | 1 |
| Me | H | H | CF₃ | H | =C(H)— | =C(H)— | 1 |
| Et | H | H | CF₃ | H | =C(H)— | =C(H)— | 1 |
| Pr | H | H | CF₃ | H | =C(H)— | =C(H)— | 1 |
| cPr | H | H | CF₃ | H | =C(H)— | =C(H)— | 1 |
| CF₃ | H | H | CF₃ | H | =C(H)— | =C(H)— | 1 |
| CH₃OCH₂ | H | H | CF₃ | H | =C(H)— | =C(H)— | 1 |
| MeO | H | H | CF₃ | H | =C(H)— | =C(H)— | 1 |
| EtO | H | H | CF₃ | H | =C(H)— | =C(H)— | 1 |
| PrO | H | H | CF₃ | H | =C(H)— | =C(H)— | 1 |
| CF₃CH₂O | H | H | CF₃ | H | =C(H)— | =C(H)— | 1 |
| CHF₂CH₂O | H | H | CF₃ | H | =C(H)— | =C(H)— | 1 |
| iPrO | H | H | CF₃ | H | =C(H)— | =C(H)— | 1 |
| Ph | H | H | CF₃ | H | =C(H)— | =C(H)— | 1 |
| H | H | H | CF₃ | H | =C(H)— | N | 0 |
| F | H | H | CF₃ | H | =C(H)— | N | 0 |
| Cl | H | H | CF₃ | H | =C(H)— | N | 0 |
| Br | H | H | CF₃ | H | =C(H)— | N | 0 |
| I | H | H | CF₃ | H | =C(H)— | N | 0 |
| Me | H | H | CF₃ | H | =C(H)— | N | 0 |
| Et | H | H | CF₃ | H | =C(H)— | N | 0 |

TABLE 35

| R¹ | R² | R³ | R⁴ | R⁵ | A¹ | A² | n |
|---|---|---|---|---|---|---|---|
| Pr | H | H | CF₃ | H | =C(H)— | N | 0 |
| cPr | H | H | CF₃ | H | =C(H)— | N | 0 |
| CF₃ | H | H | CF₃ | H | =C(H)— | N | 0 |
| CH₃OCH₂ | H | H | CF₃ | H | =C(H)— | N | 0 |
| MeO | H | H | CF₃ | H | =C(H)— | N | 0 |
| EtO | H | H | CF₃ | H | =C(H)— | N | 0 |
| PrO | H | H | CF₃ | H | =C(H)— | N | 0 |
| CF₃CH₂O | H | H | CF₃ | H | =C(H)— | N | 0 |
| CHF₂CH₂O | H | H | CF₃ | H | =C(H)— | N | 0 |
| iPrO | H | H | CF₃ | H | =C(H)— | N | 0 |
| cPrCH₂O | H | H | CF₃ | H | =C(H)— | N | 0 |
| cPenO | H | H | CF₃ | H | =C(H)— | N | 0 |
| MeS | H | H | CF₃ | H | =C(H)— | N | 0 |
| MeS(O) | H | H | CF₃ | H | =C(H)— | N | 0 |
| MeS(O)₂ | H | H | CF₃ | H | =C(H)— | N | 0 |

TABLE 35-continued

| R¹ | R² | R³ | R⁴ | R⁵ | A¹ | A² | n |
|---|---|---|---|---|---|---|---|
| EtS | H | H | CF₃ | H | =C(H)— | N | 0 |
| EtS(O) | H | H | CF₃ | H | =C(H)— | N | 0 |
| EtS(O)₂ | H | H | CF₃ | H | =C(H)— | N | 0 |
| PrS | H | H | CF₃ | H | =C(H)— | N | 0 |
| PrS(O) | H | H | CF₃ | H | =C(H)— | N | 0 |
| PrS(O)₂ | H | H | CF₃ | H | =C(H)— | N | 0 |
| iPrS | H | H | CF₃ | H | =C(H)— | N | 0 |
| iPrS(O) | H | H | CF₃ | H | =C(H)— | N | 0 |
| iPrS(O)₂ | H | H | CF₃ | H | =C(H)— | N | 0 |

TABLE 36

| R¹ | R² | R³ | R⁴ | R⁵ | A¹ | A² | n |
|---|---|---|---|---|---|---|---|
| CF₃CH₂S | H | H | CF₃ | H | =C(H)— | N | 0 |
| CHF₂CH₂S | H | H | CF₃ | H | =C(H)— | N | 0 |
| MeHN | H | H | CF₃ | H | =C(H)— | N | 0 |
| Me₂N | H | H | CF₃ | H | =C(H)— | N | 0 |
| Me(iPr)N | H | H | CF₃ | H | =C(H)— | N | 0 |
| Ph | H | H | CF₃ | H | =C(H)— | N | 0 |
| 2-Py | H | H | CF₃ | H | =C(H)— | N | 0 |
| 3-Py | H | H | CF₃ | H | =C(H)— | N | 0 |
| 4-Py | H | H | CF₃ | H | =C(H)— | N | 0 |
| 1-Tz | H | H | CF₃ | H | =C(H)— | N | 0 |
| 1-Pz | H | H | CF₃ | H | =C(H)— | N | 0 |
| H | H | H | CF₃ | H | N | =C(H)— | 0 |
| F | H | H | CF₃ | H | N | =C(H)— | 0 |
| Cl | H | H | CF₃ | H | N | =C(H)— | 0 |
| Br | H | H | CF₃ | H | N | =C(H)— | 0 |
| I | H | H | CF₃ | H | N | =C(H)— | 0 |
| Me | H | H | CF₃ | H | N | =C(H)— | 0 |
| Et | H | H | CF₃ | H | N | =C(H)— | 0 |
| Pr | H | H | CF₃ | H | N | =C(H)— | 0 |
| cPr | H | H | CF₃ | H | N | =C(H)— | 0 |
| CF₃ | H | H | CF₃ | H | N | =C(H)— | 0 |
| CH₃OCH₂ | H | H | CF₃ | H | N | =C(H)— | 0 |
| MeO | H | H | CF₃ | H | N | =C(H)— | 0 |
| EtO | H | H | CF₃ | H | N | =C(H)— | 0 |

TABLE 37

| R¹ | R² | R³ | R⁴ | R⁵ | A¹ | A² | n |
|---|---|---|---|---|---|---|---|
| PrO | H | H | CF₃ | H | N | =C(H)— | 0 |
| CF₃CH₂O | H | H | CF₃ | H | N | =C(H)— | 0 |
| CHF₂CH₂O | H | H | CF₃ | H | N | =C(H)— | 0 |
| iPrO | H | H | CF₃ | H | N | =C(H)— | 0 |
| cPrCH₂O | H | H | CF₃ | H | N | =C(H)— | 0 |
| cPenO | H | H | CF₃ | H | N | =C(H)— | 0 |
| MeS | H | H | CF₃ | H | N | =C(H)— | 0 |
| MeS(O) | H | H | CF₃ | H | N | =C(H)— | 0 |
| MeS(O)₂ | H | H | CF₃ | H | N | =C(H)— | 0 |
| EtS | H | H | CF₃ | H | N | =C(H)— | 0 |
| EtS(O) | H | H | CF₃ | H | N | =C(H)— | 0 |
| EtS(O)₂ | H | H | CF₃ | H | N | =C(H)— | 0 |
| PrS | H | H | CF₃ | H | N | =C(H)— | 0 |
| PrS(O) | H | H | CF₃ | H | N | =C(H)— | 0 |
| PrS(O)₂ | H | H | CF₃ | H | N | =C(H)— | 0 |
| iPrS | H | H | CF₃ | H | N | =C(H)— | 0 |
| iPrS(O) | H | H | CF₃ | H | N | =C(H)— | 0 |
| iPrS(O)₂ | H | H | CF₃ | H | N | =C(H)— | 0 |
| CF₃CH₂S | H | H | CF₃ | H | N | =C(H)— | 0 |
| CHF₂CH₂S | H | H | CF₃ | H | N | =C(H)— | 0 |
| MeHN | H | H | CF₃ | H | N | =C(H)— | 0 |
| Me₂N | H | H | CF₃ | H | N | =C(H)— | 0 |
| Me(iPr)N | H | H | CF₃ | H | N | =C(H)— | 0 |
| Ph | H | H | CF₃ | H | N | =C(H)— | 0 |

TABLE 38

| R¹ | R² | R³ | R⁴ | R⁵ | A¹ | A² | n |
|---|---|---|---|---|---|---|---|
| 2-Py | H | H | CF₃ | H | N | =C(H)— | 0 |
| 3-Py | H | H | CF₃ | H | N | =C(H)— | 0 |
| 4-Py | H | H | CF₃ | H | N | =C(H)— | 0 |
| 1-Tz | H | H | CF₃ | H | N | =C(H)— | 0 |
| 1-Pz | H | H | CF₃ | H | N | =C(H)— | 0 |
| H | H | H | CF₃O | H | =C(H)— | =C(H)— | 0 |
| F | H | H | CF₃O | H | =C(H)— | =C(H)— | 0 |
| Cl | H | H | CF₃O | H | =C(H)— | =C(H)— | 0 |
| Br | H | H | CF₃O | H | =C(H)— | =C(H)— | 0 |
| I | H | H | CF₃O | H | =C(H)— | =C(H)— | 0 |
| Me | H | H | CF₃O | H | =C(H)— | =C(H)— | 0 |
| Et | H | H | CF₃O | H | =C(H)— | =C(H)— | 0 |
| Pr | H | H | CF₃O | H | =C(H)— | =C(H)— | 0 |
| cPr | H | H | CF₃O | H | =C(H)— | =C(H)— | 0 |
| CF₃ | H | H | CF₃O | H | =C(H)— | =C(H)— | 0 |
| CH₃OCH₂ | H | H | CF₃O | H | =C(H)— | =C(H)— | 0 |
| MeO | H | H | CF₃O | H | =C(H)— | =C(H)— | 0 |
| EtO | H | H | CF₃O | H | =C(H)— | =C(H)— | 0 |
| PrO | H | H | CF₃O | H | =C(H)— | =C(H)— | 0 |
| CF₃CH₂O | H | H | CF₃O | H | =C(H)— | =C(H)— | 0 |
| CHF₂CH₂O | H | H | CF₃O | H | =C(H)— | =C(H)— | 0 |
| iPrO | H | H | CF₃O | H | =C(H)— | =C(H)— | 0 |
| cPrCH₂O | H | H | CF₃O | H | =C(H)— | =C(H)— | 0 |
| cPenO | H | H | CF₃O | H | =C(H)— | =C(H)— | 0 |

TABLE 39

| R¹ | R² | R³ | R⁴ | R⁵ | A¹ | A² | n |
|---|---|---|---|---|---|---|---|
| MeS | H | H | CF₃O | H | =C(H)— | =C(H)— | 0 |
| MeS(O) | H | H | CF₃O | H | =C(H)— | =C(H)— | 0 |
| MeS(O)₂ | H | H | CF₃O | H | =C(H)— | =C(H)— | 0 |
| EtS | H | H | CF₃O | H | =C(H)— | =C(H)— | 0 |
| EtS(O) | H | H | CF₃O | H | =C(H)— | =C(H)— | 0 |
| EtS(O)₂ | H | H | CF₃O | H | =C(H)— | =C(H)— | 0 |
| PrS | H | H | CF₃O | H | =C(H)— | =C(H)— | 0 |
| PrS(O) | H | H | CF₃O | H | =C(H)— | =C(H)— | 0 |
| PrS(O)₂ | H | H | CF₃O | H | =C(H)— | =C(H)— | 0 |
| iPrS | H | H | CF₃O | H | =C(H)— | =C(H)— | 0 |
| iPrS(O) | H | H | CF₃O | H | =C(H)— | =C(H)— | 0 |
| iPrS(O)₂ | H | H | CF₃O | H | =C(H)— | =C(H)— | 0 |
| CF₃CH₂S | H | H | CF₃O | H | =C(H)— | =C(H)— | 0 |
| CHF₂CH₂S | H | H | CF₃O | H | =C(H)— | =C(H)— | 0 |
| MeHN | H | H | CF₃O | H | =C(H)— | =C(H)— | 0 |
| Me₂N | H | H | CF₃O | H | =C(H)— | =C(H)— | 0 |
| Me(iPr)N | H | H | CF₃O | H | =C(H)— | =C(H)— | 0 |
| Ph | H | H | CF₃O | H | =C(H)— | =C(H)— | 0 |
| 2-Py | H | H | CF₃O | H | =C(H)— | =C(H)— | 0 |
| 3-Py | H | H | CF₃O | H | =C(H)— | =C(H)— | 0 |
| 4-Py | H | H | CF₃O | H | =C(H)— | =C(H)— | 0 |
| 1-Tz | H | H | CF₃O | H | =C(H)— | =C(H)— | 0 |
| 1-Pz | H | H | CF₃O | H | =C(H)— | =C(H)— | 0 |
| H | H | H | CF₃O | H | =C(H)— | =C(H)— | 1 |

TABLE 40

| R¹ | R² | R³ | R⁴ | R⁵ | A¹ | A² | n |
|---|---|---|---|---|---|---|---|
| F | H | H | CF₃O | H | =C(H)— | =C(H)— | 1 |
| Cl | H | H | CF₃O | H | =C(H)— | =C(H)— | 1 |
| Br | H | H | CF₃O | H | =C(H)— | =C(H)— | 1 |
| I | H | H | CF₃O | H | =C(H)— | =C(H)— | 1 |
| Me | H | H | CF₃O | H | =C(H)— | =C(H)— | 1 |
| Et | H | H | CF₃O | H | =C(H)— | =C(H)— | 1 |
| Pr | H | H | CF₃O | H | =C(H)— | =C(H)— | 1 |
| cPr | H | H | CF₃O | H | =C(H)— | =C(H)— | 1 |
| CF₃ | H | H | CF₃O | H | =C(H)— | =C(H)— | 1 |
| CH₃OCH₂ | H | H | CF₃O | H | =C(H)— | =C(H)— | 1 |
| MeO | H | H | CF₃O | H | =C(H)— | =C(H)— | 1 |
| EtO | H | H | CF₃O | H | =C(H)— | =C(H)— | 1 |
| PrO | H | H | CF₃O | H | =C(H)— | =C(H)— | 1 |
| CF₃CH₂O | H | H | CF₃O | H | =C(H)— | =C(H)— | 1 |
| CHF₂CH₂O | H | H | CF₃O | H | =C(H)— | =C(H)— | 1 |

TABLE 40-continued

| R¹ | R² | R³ | R⁴ | R⁵ | A¹ | A² | n |
|---|---|---|---|---|---|---|---|
| iPrO | H | H | CF₃O | H | =C(H)— | =C(H)— | 1 |
| Ph | H | H | CF₃O | H | =C(H)— | =C(H)— | 1 |
| H | H | H | CF₃S | H | =C(H)— | =C(H)— | 0 |
| F | H | H | CF₃S | H | =C(H)— | =C(H)— | 0 |
| Cl | H | H | CF₃S | H | =C(H)— | =C(H)— | 0 |
| Br | H | H | CF₃S | H | =C(H)— | =C(H)— | 0 |
| I | H | H | CF₃S | H | =C(H)— | =C(H)— | 0 |
| Me | H | H | CF₃S | H | =C(H)— | =C(H)— | 0 |
| Et | H | H | CF₃S | H | =C(H)— | =C(H)— | 0 |

TABLE 41

| R¹ | R² | R³ | R⁴ | R⁵ | A¹ | A² | n |
|---|---|---|---|---|---|---|---|
| Pr | H | H | CF₃S | H | =C(H)— | =C(H)— | 0 |
| cPr | H | H | CF₃S | H | =C(H)— | =C(H)— | 0 |
| CF₃ | H | H | CF₃S | H | =C(H)— | =C(H)— | 0 |
| CH₃OCH₂ | H | H | CF₃S | H | =C(H)— | =C(H)— | 0 |
| MeO | H | H | CF₃S | H | =C(H)— | =C(H)— | 0 |
| EtO | H | H | CF₃S | H | =C(H)— | =C(H)— | 0 |
| PrO | H | H | CF₃S | H | =C(H)— | =C(H)— | 0 |
| CF₃CH₂O | H | H | CF₃S | H | =C(H)— | =C(H)— | 0 |
| CHF₂CH₂O | H | H | CF₃S | H | =C(H)— | =C(H)— | 0 |
| iPrO | H | H | CF₃S | H | =C(H)— | =C(H)— | 0 |
| cPrCH₂O | H | H | CF₃S | H | =C(H)— | =C(H)— | 0 |
| cPenO | H | H | CF₃S | H | =C(H)— | =C(H)— | 0 |
| MeS | H | H | CF₃S | H | =C(H)— | =C(H)— | 0 |
| MeS(O) | H | H | CF₃S | H | =C(H)— | =C(H)— | 0 |
| MeS(O)₂ | H | H | CF₃S | H | =C(H)— | =C(H)— | 0 |
| EtS | H | H | CF₃S | H | =C(H)— | =C(H)— | 0 |
| EtS(O) | H | H | CF₃S | H | =C(H)— | =C(H)— | 0 |
| EtS(O)₂ | H | H | CF₃S | H | =C(H)— | =C(H)— | 0 |
| PrS | H | H | CF₃S | H | =C(H)— | =C(H)— | 0 |
| PrS(O) | H | H | CF₃S | H | =C(H)— | =C(H)— | 0 |
| PrS(O)₂ | H | H | CF₃S | H | =C(H)— | =C(H)— | 0 |
| iPrS | H | H | CF₃S | H | =C(H)— | =C(H)— | 0 |
| iPrS(O) | H | H | CF₃S | H | =C(H)— | =C(H)— | 0 |
| iPrS(O)₂ | H | H | CF₃S | H | =C(H)— | =C(H)— | 0 |

TABLE 42

| R¹ | R² | R³ | R⁴ | R⁵ | A¹ | A² | n |
|---|---|---|---|---|---|---|---|
| CF₃CH₂S | H | H | CF₃S | H | =C(H)— | =C(H)— | 0 |
| CHF₂CH₂S | H | H | CF₃S | H | =C(H)— | =C(H)— | 0 |
| MeHN | H | H | CF₃S | H | =C(H)— | =C(H)— | 0 |
| Me₂N | H | H | CF₃S | H | =C(H)— | =C(H)— | 0 |
| Me(iPr)N | H | H | CF₃S | H | =C(H)— | =C(H)— | 0 |
| Ph | H | H | CF₃S | H | =C(H)— | =C(H)— | 0 |
| 2-Py | H | H | CF₃S | H | =C(H)— | =C(H)— | 0 |
| 3-Py | H | H | CF₃S | H | =C(H)— | =C(H)— | 0 |
| 4-Py | H | H | CF₃S | H | =C(H)— | =C(H)— | 0 |
| 1-Tz | H | H | CF₃S | H | =C(H)— | =C(H)— | 0 |
| 1-Pz | H | H | CF₃S | H | =C(H)— | =C(H)— | 0 |

The composition of the present invention generally contains the present active compound and an inert carrier. The composition of the present invention is generally a formulation obtained by mixing the present active compound with a solid carrier, a liquid carrier, a gaseous carrier, and/or a bait (base material for a poison bait), and the like, and adding a surfactant or other auxiliary agents for formulation as necessary. Examples of the formulation form include an oil solution, an emulsion, a flowable, a wettable powder, a granule, a powder, and a microcapsule. The composition of the present invention generally contains 0.01 to 95% by weight of the present active compound.

Among the inert carriers, examples of the solid carrier include micropowders and grains such as clays (kaoline clay, diatomaceous earth, bentonite, Fubasami clay, Japanese acid clay, etc.), synthetic hydrous silicon oxide, talc, ceramic, other inorganic minerals (sericite, quartz, sulfur, activated carbon, calcium carbonate, etc.), and chemical fertilizers (ammonium sulfate, ammonium nitrate, ammonium chloride, etc.).

Among the inert carriers, examples of the liquid carrier include water, alcohols (methanol, ethanol, 2-propanol, ethylene glycol, etc.), ketones (acetone, methyl ethyl ketone, methyl isobutyl ketone, cyclohexanone, etc.), aromatic hydrocarbons (toluene, xylene, ethylbenzene, methylnaphthalene, etc.), aliphatic hydrocarbons (hexane, cyclohexane, kerosene, light oil, etc.), esters (ethyl acetate, butyl acetate, etc.), nitriles (acetonitrile, isobutyronitrile, etc.), ethers (ethylene glycol dimethyl ether, diisopropyl ether, 1,4-dioxane, tetrahydrofuran, etc.), acid amides (N,N-dimethylformamide, N,N-dimethylacetamide, etc.), halogenated hydrocarbons (dichloromethane, trichloroethane, etc.), dimethyl sulfoxide, and vegetable oils (soybean oil, cottonseed oil, etc.).

Among the inert carriers, examples of the gaseous carrier include fluorocarbon, butane gas, LPG (liquefied petroleum gas), dimethyl ether, and carbon dioxide.

Examples of the surfactant include alkyl sulfates, alkyl sulfonates, alkyl aryl sulfonates, alkyl aryl ethers, and polyoxyethylenated product thereof, polyethylene glycol ethers, polyhydric alcohol esters, and sugar alcohol derivatives.

Other auxiliary agents for formulation include a fixing agent, a dispersant, a stabilizer, and the like, and specific examples include casein, gelatin, sugars (starch, gum Arabic, a cellulose derivative, alginic acid, etc.), a lignin derivative, a synthetic water-soluble polymer (polyvinyl alcohol, polyvinylpyrrolidone, polyacrylic acids, etc.), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), a mineral oil, a fatty acid, and a fatty acid ester.

Examples of the base material for a poison bait include feed ingredients such as grain powder, vegetable oil, sugar, and crystalline cellulose. As necessary, an antioxidant such as dibutylhydroxytoluene or nordihydroguaiaretic acid, a preservative such as dehydroacetic acid, an agent to prevent accidental ingestion such as chili pepper powder, a pest attractive flavor such as cheese flavor, onion flavor, or peanut oil, and the like are added to the poison bait.

The method for controlling a noxious arthropod of the present invention is carried out by applying an effective amount of the present active compound to noxious arthropods or habitats of noxious arthropods. The method for controlling a noxious arthropod of the present invention is generally carried out by applying the composition of the present invention directly to noxious arthropods and/or to habitats of noxious arthropods (nest, plant body, soil, and the like). When the method for controlling a noxious arthropod of the present invention is intended for the control of noxious arthropods parasitic on cultivated plants, for example, the composition of the present invention is sprayed onto the ground part of the cultivated plants, and the composition of the present invention is irrigated to the plant foot of the cultivated plants.

When the composition of the present invention is used to control noxious arthropods in the agriculture and forestry field, its application amount is generally from 0.1 to 1,000 g in terms of the amount of the present active compound per 1,000 $m^2$. When the composition of the present invention is formulated into an emulsion, a flowable, a wettable powder, a microcapsule, or the like, it is applied by spraying after dilution with water so as to have a concentration of the present active compound of generally 1 to 10,000 ppm. When the composition of the present invention is formulated into an oil solution, a granule, a powder, or the like, it is generally applied as it is.

The formulation and the water dilution of the formulation may be directly applied by spraying to noxious arthropods or plants of crops to be protected from noxious arthropods and the like, and may be applied to the soil, in order to control noxious arthropods that live in the soil of the cultivated land.

In addition, it is also possible to apply the composition of the present invention formulated into a resin formulation by processing into a sheet or string and wind this around crops, put this around crops, placing this on the soil at the plant foot, or the like.

When the composition of the present invention is used to control noxious arthropods in the epidemic prevention field, its application amount is generally from 0.01 to 1,000 mg in terms of the amount of the present active compound per 1 $m^2$ of the application area when it is applied to a surface, and generally from 0.01 to 500 mg in terms of the amount of the present active compound per 1 $m^3$ of the application space when it is applied to a space. When the composition of the present invention is formulated into an emulsion, a flowable, a wettable powder, a microcapsule, or the like, it is applied after dilution with water so as to have a concentration of the present active compound of generally from 0.1 to 1,000 ppm. When the composition of the present invention is formulated into an oil solution, an aerosol, a smoking agent, a poison bait, or the like, it is generally used as it is.

The composition of the present invention can be used together or in combination with other insecticide, acaricide, nematicide, microbicide, plant growth-control agent, herbicide, and synergist. Examples of the active ingredients of the insecticide, acaricide, nematicide, microbicide, plant growth-control agent, herbicide, and synergist will be given below.
Examples of active ingredients of insecticides
(1) Organophosphorus Compounds Acephate, aluminiumphosphide, butathiofos, cadusafos, chlorethoxyfos, chlorfenvinphos, chlorpyrifos, chlorpyrifos-methyl, cyanophos: CYAP, diazinon, dichlorodiisopropyl ether: DCIP, dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.
(2) Carbamate Compounds Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.
(3) Pyrethroid Compounds Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6- tetrafluoro-4-(methoxymethyl)benzyl (EZ)-(1RS,3RS;1RS,3SR)-2,2-dimethyl-3-prop-1-enyl cyclopropanecarboxylate, 2,3,5,6-tetrafluoro-4-methylbenzyl (EZ)-(1RS,3RS;1RS,3SR)-2,2-dimethyl-3-prop-1-enyl cyclopropanecarboxylate, and 2,3,5,6-tetrafluoro-4-(methoxymethyl)benzyl (1RS,3RS;1RS,3SR)-2,2-dimethyl-3-(2-methyl-1-propenyl)cyclopropanecarboxylate.

(4) Nereistoxin Compounds

Cartap, bensultap, thiocyclam, monosultap, and bisultap.

(5) Neonicotinoid Compounds

Imidacloprid, nitenpyram, acetamiprid, thiamethoxam, thiacloprid, dinotefuran, and clothianidin.

(6) Benzoylurea Compounds

Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds

Acetoprole, ethiprole, fipronil, vaniliprole, pyriprole, and pyrafluprole.

(8) Bt Toxins

Live spores derived from and crystal toxins produced from *Bacillus thuringiesis* and a mixture thereof.

(9) Hydrazine Compounds

Chromafenozide, halofenozide, methoxyfenozide, and tebufenozide.

(10) Organochlorine Compounds

Aldrin, dieldrin, dienochlor, endosulfan, and methoxychlor.

(11) Other active ingredients of insecticides

Machine oil, nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, Amilbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metamammonium, metam-sodium, methyl bromide, potassium oleate, protrifenbute, spiromesifen, sulfoxaflor, sulfur, metaflumizone, spirotetramat, pyrifluquinazone, spinetoram, chlorantraniliprole, tralopyril, cyantraniliprole, a compound represented by the following formula (A):

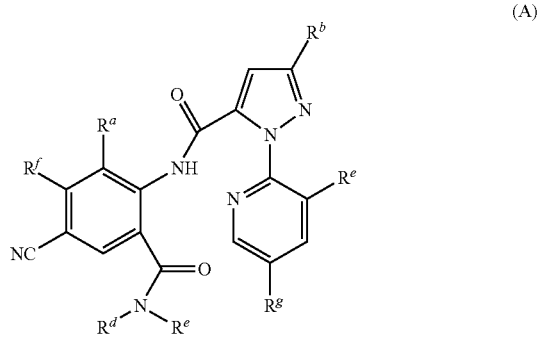

(A)

wherein
$R^a$ is Me, Cl, Br, or F,
$R^b$ is F, Cl, Br, C1 to C4 haloalkyl, or C1 to C4 haloalkoxy,
$R^c$ is F, Cl, or Br,
$R^d$ is H, or C1-C4 alkyl, C3-C4 alkenyl, C3-C4 alkynyl, or C3-C5 cycloalkylalkyl, optionally substituted with one or more halogens; CN; SMe; S(O)Me; S(O)₂Me and OMe, $R^e$ is H or Me,
$R^f$ is H, F, or Cl,
$R^g$ is H, F, or Cl, and
a compound represented by the following formula (L):

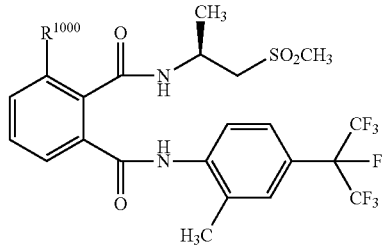

(L)

wherein
$R^{1000}$ is chlorine, bromine, or iodine.

Active Ingredients of Acaricides

Acequinocyl, amitraz, benzoximate, bifenaate, bromopropylate, chinomethionat, chlorobenzilate, CPCBS (chlorfenson), clofentezine, cyflumetofen, Kelthane (dicofol), etoxazole, fenbutatin oxide, fenothiocarb, fenpyroximate, fluacrypyrim, fluproxyfen, hexythiazox, propargite: BPPS, polynactins, pyridaben, pyrimidifen, tebufenpyrad, tetradifon, spirodiclofen, spiromesifen, spirotetramat, amidoflumet, and cyenopyrafen.

Active Ingredients of Nematocides

DCIP, fosthiazate, levamisol hydrochloride, methylsothiocyanate, morantel tartarate, and imicyafos.

Active Ingredients of Fungicides

Azole compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine compounds such as fenpropimorph, tridemorph, and fenpropidin;

Benzimidazole compounds such as carbendezim, benomyl, thiabendazole, and thiophanate-methyl;

Procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid and proquinazid; isotianil; and tiadinil.

Active Ingredients of Herbicides (1) Phenoxy Fatty Acid Compounds 2,4-PA, MCP, MCPB, phenothiol, mecoprop, fluoroxypyr, triclopyr, clomeprop, and naproanilide.

(2) Benzoic Acid Compounds 2,3,6-TBA, dicamba, clopyralid, picloram, aminopyralid, quinclorac, and quinmerac.

(3) Urea Compounds

Diuron, linuron, chlortoluron, isoproturon, fluometuron, isouron, tebuthiuron, methabenzthiazuron, cumyluron, daimuron, and methyl-daimuron.

(4) Triazine Compounds

Atrazine, ametoryn, cyanazine, simazine, propazine, simetryn, dimethametryn, prometryn, metribuzin, triaziflam, and indaziflam.

(5) Bipyridinium Compounds

Paraquat and diquat.

(6) Hydroxybenzonitrile Compounds

Bromoxynil and ioxynil.

(7) Dinitroaniline Compounds

Pendimethalin, prodiamine, and trifluralin.

(8) Organophosphorus Compounds

Amiprofos-methyl, butamifos, bensulide, piperophos, anilofos, glyphosate, glufosinate, glufosinate-P, and bialaphos.

(9) Carbamate compounds

Di-allate, tri-allate, EPTC, butylate, benthiocarb, esprocarb, molinate, dimepiperate, swep, chlorpropham, phenmedipham, phenisopham, pyributicarb, and asulam.

(10) Acid amide compounds

Propanil, propyzamide, bromobutide, etobenzanid, and the like;

(11) Chloroacetanilide Compounds

Acetochlor, alachlor, butachlor, dimethenamid, propachlor, metazachlor, metolachlor, pretilachlor, thenylchlor, and pethoxamid.

(12) Diphenylether Compounds

Acifluorfen-sodium, bifenox, oxyfluorfen, lactofen, fomesafen, chlomethoxynil, and aclonifen.

(13) Cyclic Imide Compounds

Oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Compounds

Benzofenap, pyrazolate, pyrazoxyfen, topramezone, and pyrasulfotole.

(15) Triketone Compounds

Isoxaflutole, benzobicyclon, sulcotrione, mesotrione, tembotrione, tefuryltrione, and bicyclopyrone.

(16) Aryloxyphenoxypropionate Compounds

Clodinafop-propargyl, cyhalofop-butyl, diclofop-methyl, fenoxaprop-ethyl, fluazifop-butyl, haloxyfop-methyl, quizalofop-ethyl, and metamifop.

(17) Trioneoxime Compounds

Alloxydim-sodium, sethoxydim, butroxydim, clethodim, cloproxydim, cycloxydim, tepraloxydim, tralkoxydim, and profoxydim.

(18) Sulfonylurea Compounds

Chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, propyrisulfuron, and metazosulfuron.

(19) Imidazolinone Compounds

Imazamethabenz-methyl, imazamethapyr, imazamox, imazapyr, imazaquin, and imazethapyr.

(20) Sulfonamide Compounds

Flumetsulam, metosulam, diclosulam, florasulam, cloransulam-methyl, penoxsulam, and pyroxsulam.

(21) Pyrimidinyloxybenzoate compounds

Pyrithiobac-sodium, bispyribac-sodium, pyriminobac-methyl, pyribenzoxim, pyriftalid, and pyrimisulfan.

(22) Other Herbicidal Compounds

Bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, methiozolin, and fenoxasulfone. Active ingredients of plant growth-control agents Hymexazol, paclobutrazol, uniconazole-P, inabenfide, prohexadione-calcium, aviglycine, 1-naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride, and 4-CPA (4-chlorophenoxyacetic acid).

Active Ingredients of Synergists

Piperonyl butoxide, sesamex, sulfoxide, N-(2-ethylhexyl)-8,9,10-trinorborne-5-ene-2,3-dicarboximide (MGK 264), N-declyimidazole, WARF-antiresistant, TBPT, TPP, IBP, PSCP, CH$_3$I, t-phenylbutenone, diethylmaleate, DMC, FDMC, ETP, and ETN.

Examples of the noxious arthropods on which the present active compound exhibits an effect include noxious insects and noxious mites. Examples of the noxious arthropods include the following pests.

Hemiptera: Delphacidae such as *Laodelphax striatellus, Nilaparvata lugens*, and *Sogatella furcifera*, Deltocephalidae such as *Nephotettix cincticeps, Nephotettix virescens*, and *Empoasca onukii*, Aphididae such as *Aphis gossypii, Myzus persicae, Brevicoryne brassicae, Aphis spiraecola, Macrosiphum euphorbiae, Aulacorthum solani, Rhopalosiphum padi, Toxoptera citricidus*, and *Hyalopterus pruni*, Pentatomidae such as *Nezara antennata, Riptortus clavetus, Leptocorisa chinensis, Eysarcoris parvus*, and *Halyomorpha mista*, leyrodidae such as *Trialeurodes vaporariorum; Bemisia tabaci, Dialeurodes citri*, and *Aleurocanthus spiniferus*, Coccidae such as *Aonidiella aurantii, Comstockaspis perniciosa, Unaspis citri, Ceroplastes rubens, Icerya purchasi, Planococcus kraunhiae, Pseudococcus longispinis*, and *Pseudaulacaspis pentagona*, Tingidae, Cimicidae such as *Cimex lectularius*, and Psyllidae.

Lepidoptera: Pyralidae such as *Chilo suppressalis, Tryporyza incertulas, Cnaphalocrocis medinalis, Notarcha derogata, Plodia interpunctella, Ostrinia furnacalis, Hellula undalis*, and *Pediasia teterrellus*, Noctuidae such as *Spodoptera litura, Spodoptera exigua, Pseudaletia separata, Mamestra brassicae, Agrotis ipsilon, Plusia nigrisigna, Trichoplusia* spp., *Heliothis* spp. and *Helicoverpa* spp., Pieridae such as *Pieris rapae*, Tortricidae such as *Adoxophyes* spp., *Grapholita molesta, Leguminivora glycinivorella, Matsumuraeses azukivora, Adoxophyes orana fasciata, Adoxophyes honmai., Homona magnanima, Archips fuscocupreanus*, and *Cydia pomonella*, Gracillariidae such as *Caloptilia theivora* and *Phyllonorycter ringoneella*, Carposimidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thrips such as *Frankliniella occidentalis, Thrips parmi, Scirtothrips dorsalis, Thrips tabaci*, and *Frankliniella intonsa*.

Diptera: *Culex* such as *Culex pipiens pallens, Culex tritaeniorhynchus*, and *Culex quinquefasciatus, Aedes* spp. such as *Aedes aegypti* and *Aedes albopictus, Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae, Hydrellia griseola, Liriomyza sativae, Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Simuliidae, Tabanidae such as *Tabanus trigonus*, and *Stomoxys*.

Coleoptera: *Diabrotica* such as *Diabrotica virgifera virgifera* and *Diabrotica undecimpunctata howardi*, Scarabaeidae such as *Anomala cuprea, Anomala rufocuprea*, and *Popillia japonica*, Curculionidae such as *Sitophilus zeamais, Lissorhoptrus oryzophilus, Callosobruchuys chienensis, Echinocnemus squameus, Anthonomus grandis*, and *Sphenophorus venatus*, Tenebrionidae such as *Tenebrio molitor* and *Tribolium castaneum*, Chrysomelidae such as *Oulema oryzae, Aulacophora femoralis, Phyllotreta striolata*, and *Leptinotarsa decemlineata*, Dermestidae such as *Anthrenus verbasci* and *Dermestes maculates*, Anobiidae such as *Lasioderma serricorne, Epilachna* such as *Epilachna vigintioctopunctata*, Limnoridae such as *Lyctus brunneus* and *Tomicus piniperda*, Bostrychidae, Ptimidae, Cerambycidae such as *Anoplophora malasiaca, Agriotes* spp., and *Paederus fuscipes*.

Orthoptera: *Locusta migratoria, Gryllotalpa africana, Oxya yezoensis, Oxya japonica*, and *Grylloidea*.

Aphaniptera: *Ctenocephalides felis, Ctenocephalides canis, Pulex irritans, Xenopsylla cheopis*, and the like.

Anoplura: *Pediculus humanus corporis, Phthirus pubis, Haematopinus eurysternus, Dalmalinia ovis, Haematopinus suis*, and the like.

Hymenoptera: Formicidae such as *Monomorium pharaosis, Formica fusca japonica, Ochetellus glaber, Pristomyrmex pungens, Pheidole noda, Acromyrmex* spp., and *Solenopsis* spp., Vespidae, Bethylidae, and Tenthredimidae such as *Athalia rosae* and *Athalia japonica*.

Blattodea: *Blattella germanica, Periplaneta fuliginosa, Periplaneta americana, Periplaneta brunnea*, and *Blatta orientalis*.

Acarina: Tetranychidae such as *Tetranychus urticae, Tetranychus kanzawai, Panonychus citri, Panonychus ulmi*, and *Oligonychus* spp., Eriophyidae such as *Aculops pelekassi, Phyllocoptruta citri, Aculops lycopersici, Calacarus carinatus, Acaphylla theavagrans*, and *Eriophyes chibaensis, Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis, Haemaphysalis flava, Dermacentor taiwanicus, Ixodes ovatus, Ixodes persulcatus, Ixodes scapularis, Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus, Cheyletus malaccensis* and *Cheyletus moorei*, Dermanyssidae such as *Ornithonyssus bacoti, Ornithonyssus sylvairum*, and *Dermanyssus gallinae*, Trombiculidae such as *Leptotrombidium akamushi*, and *Arachnida* such as *Chiracanthium japonicum* and *Latrodectus hasseltii*.

The composition of the present invention can be used in agricultural lands for cultivating "crops" listed below.

Agricultural crops: corn, rice, wheat, barley, rye, oat, sorghum, cotton, soybean, peanut, sarrazin, sugar beet, rapeseed, sunflower, sugar cane, tobacco, and the like.

Vegetables: Solanaceae vegetables (eggplant, tomato, green pepper, chili pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese basil, mint, basil, etc.), strawberry, sweat potato, yam, aroid, and the like.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut palm, oil palm, and the like.

Trees other than fruit trees: tea, mulberry, flowering trees (rhododendron, camellia, hydrangea, sasanqua, Japanese star anise, Japanese Chemy, tulip tree, Crape myrtle, fragrant orange-colored olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, Japanese horse-chestnut, etc.), Sweet viburnum, Largeleaf podocarp, Japanese cedar, Hinoki cypress, croton, Japanese Spindle, Chinese hawthorn, and the like.

Lawn: zoysia (Japanese lawn grass, mascarene grass, etc.), Bermuda grass (Cynodon dactylon, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, and the like.

Others: flowering herbs (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsettia, gladiolus, cattleya, daisy, cymbidium, begonia, etc.), biofuel plants (jatropha, safflower, Camelina alyssum, switch grass, Miscanthus, reed Canary grass, Great reed, kenaf, cassava, willow, algae, etc.), ornamental foliage plants, and the like.

The "crops" also include genetically modified crops.

EXAMPLES

Hereinafter, the present invention will be described in more detail with reference to production examples, reference production examples, and test examples. However, the present invention is not limited to these examples.

First, production examples for the production of the present active compounds will be given.

Production Example 1

A mixture of 0.50 g of 5-tert-butyl-2-hydroxybenzaldehyde, 0.48 g of 4-(chloromethyl)pyridine hydrochloride, 0.78 g of potassium carbonate, 0.49 g of potassium iodide and 10 ml of DMF was stirred at 80° C. for 2 hours. Subsequently, 0.78 g of potassium carbonate was added to the reaction mixture, and the mixture was stirred at 150° C. for 8 hours. The reaction mixture was cooled to room temperature. Water was added to the reaction mixture, and the precipitated solid was collected by filtration. This solid was dissolved in ethyl acetate. The organic layer was washed with water and saturated brine and dried over sodium sulfate, then concentrated under reduced pressure. The residue was subjected to silica gel column chromatography to obtain 0.48 g of 4-(5-tert-butylbenzofuran-2-yl)pyridine (hereinafter, referred to as "Present Active Compound 1").

Present Active Compound 1

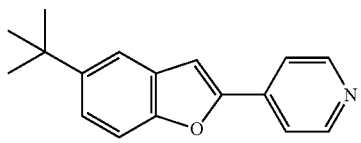

$^1$H-NMR (CDCl$_3$) δ: 8.67 (dd, J=4.6, 1.7 Hz, 2H), 7.69 (dd, J=4.6, 1.7 Hz, 2H), 7.63-7.61 (m, 1H), 7.48 (d, J=8.8 Hz, 1H), 7.43 (dd, J=8.8, 2.0 Hz, 1H), 7.22-7.21 (m, 1H), 1.39 (s, 9H)

Production Example 2

A mixture of 0.64 g of 2-hydroxy-5-methoxybenzaldehyde, 0.72 g of 4-(chloromethyl)pyridine hydrochloride, 1.74 g of potassium carbonate, 0.70 g of potassium iodide and 15 ml of DMF was stirred at 80° C. for 3 hours and subsequently at 150° C. for 6 hours. The reaction mixture was cooled to room temperature. Water was added to the reaction mixture, and the mixture was extracted twice with ethyl acetate. The organic layers were combined and washed with water and saturated brine and dried over sodium sulfate, then concentrated under reduced pressure. The residue was subjected to silica gel column chromatography to obtain 0.60 g of 4-(5-methoxybenzofuran-2-yl)pyridine (hereinafter, referred to as "Present Active Compound 2").

Present Active Compound 2

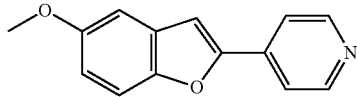

$^1$H-NMR (CDCl$_3$) δ: 8.71-8.66 (m, 2H), 7.71-7.66 (m, 2H), 7.44 (d, J=9.0 Hz, 1H), 7.19 (s, 1H), 7.07 (d, J=2.5 Hz, 1H), 6.97 (dd, J=9.0, 2.6 Hz, 1H), 3.87 (s, 3H)

Production Example 3

A mixture of 1.0 g of 2-hydroxy-5-(trifluoromethyl)benzaldehyde, 0.86 g of 4-(chloromethyl)pyridine hydrochloride, 2.54 g of potassium carbonate and 20 ml of DMF was stirred at 80° C. for 2 hours and subsequently at 150° C. for 3 hours. The reaction mixture was cooled to room temperature. Water was added to the reaction mixture, and the mixture was extracted twice with ethyl acetate. The organic layers were combined and washed with water and saturated brine and dried over magnesium sulfate, then concentrated under reduced pressure. The residue was subjected to silica gel column chromatography to obtain 0.91 g of 4-[5-(trifluoromethyl)benzofuran-2-yl]pyridine (hereinafter, referred to as "Present Active Compound 3").

Present Active Compound 3

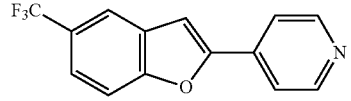

$^1$H-NMR (CDCl$_3$) δ: 8.72 (dd, J=4.6, 1.7 Hz, 2H), 7.94-7.93 (m, 1H), 7.72 (dd, J=4.6, 1.7 Hz, 2H), 7.65 (d, J=8.5 Hz, 1H), 7.63-7.60 (m, 1H), 7.31-7.30 (m, 1H)

Production Example 4

The same procedures as in Production Example 3 were carried out using 2-hydroxy-4-(trifluoromethyl)benzaldehyde in place of 2-hydroxy-5-(trifluoromethyl)benzaldehyde to obtain 4-[6-(trifluoromethyl)benzofuran-2-yl]pyridine (hereinafter, referred to as "Present Active Compound 4").

Present Active Compound 4

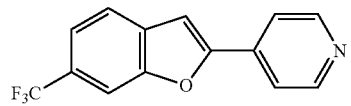

$^1$H-NMR (CDCl$_3$) δ: 8.74 (dd, J=4.5, 1.7 Hz, 2H), 7.86-7.84 (m, 1H), 7.76-7.72 (m, 3H), 7.56-7.53 (m, 1H), 7.31-7.29 (m, 1H)

Production Example 5

A mixture of 0.60 g of 2-hydroxy-5-(pentafluoroethyl)benzaldehyde, 0.41 g of 4-(chloromethyl)pyridine hydrochloride, 1.21 g of potassium carbonate, 0.41 g of potassium iodide and 10 ml of DMF was stirred at 80° C. for 2 hours and subsequently at 150° C. for 3 hours. Thereto was added 0.8 g of potassium carbonate, and the mixture was stirred at 150° C. for 2 hours. The reaction mixture was cooled to room temperature. Water was added to the reaction mixture, and the mixture was extracted twice with ethyl acetate. The organic layers were combined and washed with water and saturated brine and dried over magnesium sulfate, then concentrated under reduced pressure. The residue was subjected to silica gel column chromatography to obtain 0.20 g of 4-[5-(pentafluoroethyl)benzofuran-2-yl]pyridine (hereinafter, referred to as "Present Active Compound 5").

Present Active Compound 5

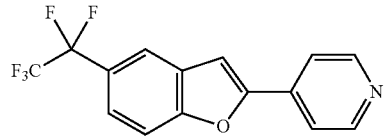

$^1$H-NMR (CDCl$_3$) δ: 8.73 (dd, J=4.5, 1.6 Hz, 2H), 7.92-7.91 (m, 1H), 7.73 (dd, J=4.6, 1.7 Hz, 2H), 7.68 (d, J=8.8 Hz, 1H), 7.61-7.57 (m, 1H), 7.32-7.31 (m, 1H)

Production Example 6

A mixture of 0.78 g of 2-hydroxy-5-(trifluoromethyl)benzaldehyde, 0.89 g of 3-chloro-4-(chloromethyl)pyridine, 1.94 g of potassium carbonate and 15 ml of DMF was stirred at 80° C. for 3 hours and subsequently at 150° C. for 4 hours. The reaction mixture was cooled to room temperature. Water was added to the reaction mixture, and the mixture was extracted twice with ethyl acetate. The organic layers were combined and washed with water and saturated brine and dried over magnesium sulfate, then concentrated under reduced pressure. The residue was subjected to silica gel column chromatography to obtain 0.72 g of 3-chloro-4-[5-(trifluoromethyl) benzofuran-2-yl]pyridine (hereinafter, referred to as "Present Active Compound 6").

Present Active Compound 6

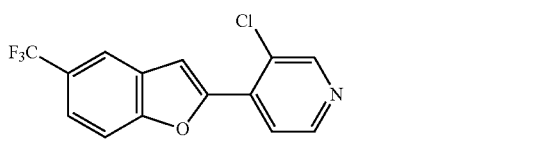

$^1$H-NMR (CDCl$_3$) δ: 8.73 (s, 1H), 8.62 (d, J=5.1 Hz, 1H), 8.00-7.99 (m, 1H), 7.97 (d, J=5.1 Hz, 1H), 7.86 (s, 1H), 7.67-7.66 (m, 2H).

Production Example 7

To a mixture of 0.38 g of 3-chloro-4-[5-(trifluoromethyl) benzofuran-2-yl]pyridine and 4 ml of chloroform was added 0.41 g of 70% m-chloroperbenzoic acid under ice-cooling. This mixture was stirred under ice-cooling for 30 minutes and subsequently at room temperature for 2 hours. The reaction mixture was diluted with chloroform, and sequentially washed with a 5% aqueous solution of sodium hydroxide and saturated brine. The organic layer was dried over magnesium sulfate, then concentrated under reduced pressure. The residue was subjected to silica gel column chromatography to obtain 0.32 g of 3-chloro-4-[5-(trifluoromethyl)benzofuran-2-yl]pyridine 1-oxide (hereinafter, referred to as "Present Active Compound 7").

Present Active Compound 7

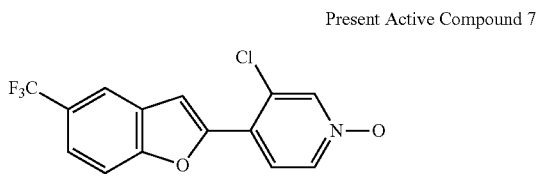

$^1$H-NMR (CDCl$_3$) δ: 8.36 (d, J=1.7 Hz, 1H), 8.19 (dd, J=7.0, 1.8 Hz, 1H), 7.99-7.95 (m, 2H), 7.74-7.73 (m, 1H), 7.68-7.61 (m, 2H)

Production Example 8

A mixture of 1.59 g of 2-hydroxy-5-(trifluoromethyl)benzaldehyde, 1.22 g of 4-(chloromethyl)-3-fluoropyridine, 3.48 g of potassium carbonate and 7 ml of DMF was stirred at 80° C. for 1 hour and subsequently at 150° C. for 2 hours. The reaction mixture was cooled to room temperature. Water was added to the reaction mixture, and the mixture was extracted twice with ethyl acetate. The organic layers were combined and washed with water and saturated brine and dried over magnesium sulfate, then concentrated under reduced pressure. The residue was subjected to silica gel column chromatography to obtain 1.27 g of 3-fluoro-4-[5-(trifluoromethyl) benzofuran-2-yl]-pyridine (hereinafter, referred to as "Present Active Compound 8").

Present Active Compound 8

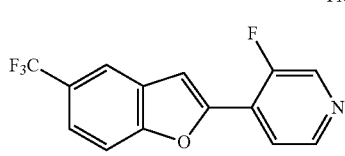

$^1$H-NMR (CDCl$_3$) δ: 8.62-8.60 (m, 1H), 8.57-8.54 (m, 1H), 7.97 (s, 1H), 7.93-7.89 (m, 1H), 7.69-7.62 (m, 2H), 7.50 (d, J=2.9 Hz, 1H)

Production Example 9

A mixture of 0.19 g of 3-fluoro-4-[5-(trifluoromethyl)benzofuran-2-yl]pyridine, 0.19 g of potassium carbonate and 3 ml of methanol was heated under reflux for 27 hours. To this mixture was added 93 mg of potassium carbonate, and the mixture was further heated under reflux for 2 hours. The reaction mixture was cooled to room temperature. Water was added to the reaction mixture, and the mixture was extracted twice with ethyl acetate. The organic layers were combined and washed with saturated brine and dried over magnesium sulfate, then concentrated under reduced pressure. The residue was subjected to silica gel column chromatography to obtain 0.16 g of 3-methoxy-4-[5-(trifluoromethyl)benzofuran-2-yl]pyridine (hereinafter, referred to as "Present Active Compound 9").

Present Active Compound 9

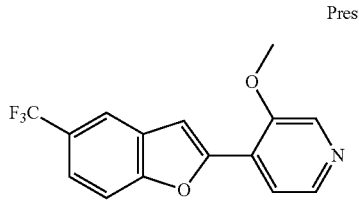

$^1$H-NMR (CDCl$_3$) δ: 8.46 (s, 1H), 8.40 (d, J=4.9 Hz, 1H), 7.95-7.93 (m, 1H), 7.90 (d, J=4.9 Hz, 1H), 7.65-7.58 (m, 3H), 4.14 (s, 3H)

Production Example 10

A mixture of 75 mg of 2,2-difluoroethanol and 0.5 ml of DMF was added to a mixture of 36 mg of sodium hydride (60%, oil-based) and 3 ml of DMF under ice-cooling. This mixture was stirred at room temperature for 15 minutes, and then ice-cooled. Subsequently, 0.20 g of 3-fluoro-4-[5-(trifluoromethyl)benzofuran-2-yl]pyridine was added thereto, and the mixture was stirred at room temperature for 3.5 hours. Thereto was added a mixture of 29 mg of 2,2-difluoroethanol, 0.5 ml of DMF and 14 mg of sodium hydride (60%, oil-based), and the mixture was stirred at room temperature for 1.5 hours. Water was added to the reaction mixture, and the mixture was extracted with ethyl acetate. The organic layer was washed with water and saturated brine and dried over magnesium sulfate, then concentrated under reduced pressure. The residue was subjected to silica gel column chromatography to obtain 0.20 g of 3-(2,2-difluoroethoxy)-4-[5-(trifluoromethyl)benzofuran-2-yl]pyridine (hereinafter, referred to as "Present Active Compound 10").

Present Active Compound 10

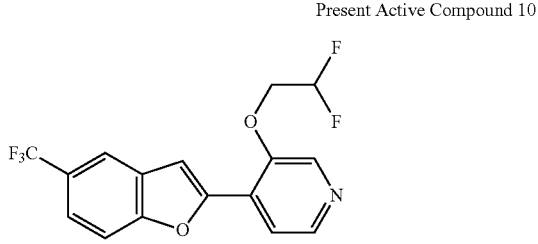 [SMILES: FC(F)COc1cnccc1-c1cc2cc(C(F)(F)F)ccc2o1]

$^1$H-NMR (CDCl$_3$) δ: 8.46 (d, J=5.0 Hz, 1H), 8.41 (s, 1H), 7.99-7.97 (m, 1H), 7.95 (d, J=4.9 Hz, 1H), 7.66-7.60 (m, 2H), 7.56 (s, 1H), 6.28 (tt, J=54.5, 3.7 Hz, 1H), 4.51 (td, J=13.0, 3.7 Hz, 2H)

Production Example 11

A mixture of 0.30 g of 3-fluoro-4-[5-(trifluoromethyl)benzofuran-2-yl]pyridine, 75 mg of methyl mercaptan sodium salt and 4 ml of DMF was stirred under ice-cooling for 1 hour. To this mixture was added 37 mg of methyl mercaptan sodium salt, and the mixture was stirred under ice-cooling for further 1 hour. Water was added to the reaction mixture, and the mixture was extracted twice with ethyl acetate. The organic layers were combined and washed with water and saturated brine and dried over magnesium sulfate, then concentrated under reduced pressure. The residue was subjected to silica gel column chromatography to obtain 0.31 g of 3-methylthio-4-[5-(trifluoromethyl)benzofuran-2-yl]pyridine (hereinafter, referred to as "Present Active Compound 11").

Present Active Compound 11

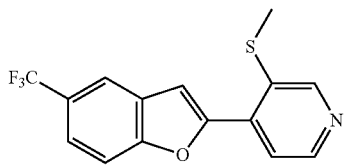

$^1$H-NMR (CDCl$_3$) δ: 8.62 (s, 1H), 8.53 (d, J=5.1 Hz, 1H), 7.98 (s, 1H), 7.85 (d, J=5.1 Hz, 1H), 7.72 (s, 1H), 7.67-7.61 (m, 2H), 2.65 (s, 3H)

Production Example 12

A mixture of 0.25 g of 3-fluoro-4-[5-(trifluoromethyl)benzofuran-2-yl]pyridine, 0.11 g of ethyl mercaptan sodium salt and 3.5 ml of DMF was stirred under ice-cooling for 2 hours. Water was added to the reaction mixture, and the mixture was extracted twice with ethyl acetate. The organic layers were combined and washed with water and saturated brine and dried over magnesium sulfate, then concentrated under reduced pressure. The residue was subjected to silica gel column chromatography to obtain 0.26 g of 3-ethylthio-4-[5-(trifluoromethyl)benzofuran-2-yl]pyridine (hereinafter, referred to as "Present Active Compound 12").

Present Active Compound 12

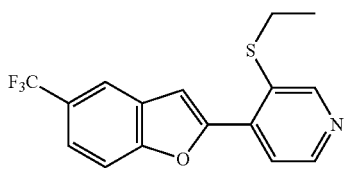

$^1$H-NMR (CDCl$_3$) δ: 8.69 (s, 1H), 8.54 (d, J=5.1 Hz, 1H), 7.99-7.97 (m, 1H), 7.88-7.86 (m, 1H), 7.83 (s, 1H), 7.66-7.61 (m, 2H), 3.09 (q, J=7.4 Hz, 2H), 1.38 (t, J=7.3 Hz, 3H)

Production Example 13

A mixture of 0.29 g of 3-iodo-5-(trifluoromethyl)pyridin-2-ol, 0.35 g of 4-ethynylpyridine, 20 mg of dichlorobis(triphenylphosphine)palladium(II), 0.30 g of triethylamine, 15 mg of copper(I) iodide and 5 ml of DMF was stirred under a nitrogen atmosphere at room temperature for 2 hours. To the reaction mixture were added water, then t-butyl methyl ether, and the mixture was filtered through Celite (registered trademark). The filtrate was separated, and the organic layer was dried over sodium sulfate, then concentrated under reduced pressure. The residue was subjected to silica gel preparative thin-layer chromatography to obtain 33 mg of 2-(pyridin-4-yl)-5-trifluoromethyl-furo[2,3-b]pyridine (hereinafter, referred to as "Present Active Compound 13").

Present Active Compound 13

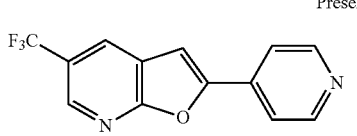

$^1$H-NMR (CDCl$_3$) δ: 8.77 (dd, J=4.4, 1.7 Hz, 2H), 8.68 (d, J=2.2 Hz, 1H), 8.25 (d, J=2.2 Hz, 1H), 7.78 (dd, J=4.4, 1.7 Hz, 2H), 7.32 (s, 1H)

Next, reference production examples for the production of production intermediates of the above present active compounds will be given.

Reference Production Example 1

To a mixture of 4.91 g of 4-(trifluoromethyl)phenol and 68 ml of trifluoroacetic acid was gradually added 4.67 g of hexamethylenetetramine at room temperature. This mixture was heated under reflux for 24 hours. The reaction mixture was cooled to room temperature, then 35 ml of water and 19 ml of 50% sulfuric acid were added to the reaction mixture, and the mixture was stirred at room temperature for 4 hours. The reaction mixture was extracted three times with diethyl ether. The organic layers were combined and sequentially washed with 5 M hydrochloric acid and water. The organic layer was dried over magnesium sulfate, and then concentrated under reduced pressure. The residue was subjected to silica gel column chromatography to obtain 1.7 g of 2-hydroxy-5-(trifluoromethyl)benzaldehyde.

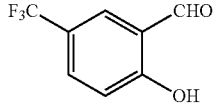

$^1$H-NMR (CDCl$_3$) δ: 11.31 (s, 1H), 9.95 (s, 1H), 7.88-7.86 (m, 1H), 7.78-7.74 (m, 1H), 7.11 (d, J=8.8 Hz, 1H)

Reference Production Example 2

A mixture of 10 g of 3-(trifluoromethyl)phenol and 15 ml of DMF was added dropwise to a mixture of 2.71 g of sodium hydride (60%, oil-based) and 45 ml of DMF under ice-cooling, and the mixture was stirred for 30 minutes. Subsequently, a mixture of 7.0 g of chloromethyl ethyl ether and 5 ml of DMF was added dropwise thereto, and the mixture was stirred for 1 hour. The reaction mixture was added to ice water. This mixture was extracted twice with ethyl acetate. The organic layers were combined and washed with water and saturated brine and dried over magnesium sulfate, then concentrated under reduced pressure, to obtain 13 g of 1-ethoxymethoxy-3-(trifluoromethyl)benzene.

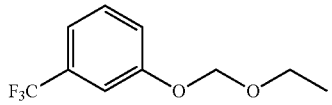

$^1$H-NMR (CDCl$_3$) δ: 7.41-7.36 (m, 1H), 7.30-7.20 (m, 3H), 5.25 (s, 2H), 3.74 (q, J=7.1 Hz, 2H), 1.23 (t, J=7.1 Hz, 3H)

To a mixture of 4.0 g of 1-ethoxymethoxy-3-trifluoromethylbenzene and 160 ml of diethyl ether was added dropwise 16 ml of n-butyllithium (1.6 N, n-hexane solution) under a nitrogen atmosphere at −70° C. This mixture was stirred at room temperature for 3 hours. Subsequently, 5.5 ml of DMF was added to this mixture at −70° C., and the temperature was returned to room temperature. The reaction mixture was added to water. This mixture was extracted twice with ethyl acetate. The organic layers were combined and washed with water and saturated brine and dried over magnesium sulfate, then concentrated under reduced pressure. The residue was subjected to silica gel column chromatography to obtain 1.90 g of 2-ethoxymethoxy-4-(trifluoromethyl)benzaldehyde.

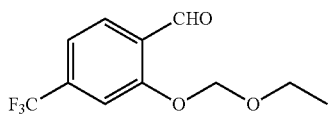 [SMILES: CCOCOc1cc(C(F)(F)F)ccc1C=O]

$^1$H-NMR (CDCl$_3$) δ: 10.51 (s, 1H), 7.94 (d, J=8.1 Hz, 1H), 7.53 (s, 1H), 7.33 (d, J=8.1 Hz, 1H), 5.40 (s, 2H), 3.79 (q, J=7.1 Hz, 2H), 1.26 (t, J=7.1 Hz, 3H)

A mixture of 1.90 g of 2-ethoxymethoxy-4-trifluoromethylbenzaldehyde, 10 ml of acetone, and 9 ml of 6 N hydrochloric acid was stirred at room temperature for 3 hours and subsequently at 40° C. for 1 hour. The reaction mixture was cooled to room temperature, then water was added to the reaction mixture. This mixture was extracted twice with ethyl acetate. The organic layers were combined and washed with water and saturated brine and dried over magnesium sulfate, then concentrated under reduced pressure, to obtain 1.05 g of 2-hydroxy-4-(trifluoromethyl)benzaldehyde.

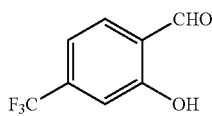

$^1$H-NMR (CDCl$_3$) δ: 11.08 (s, 1H), 9.99 (s, 1H), 7.73-7.70 (m, 1H), 7.29-7.26 (m, 2H)

Reference Production Example 3

A mixture of 25 g of 4-iodophenol and 25 ml of DMF was added dropwise to a mixture of 5.0 g of sodium hydride (60%, oil-based) and 70 ml of DMF under ice-cooling, and the mixture was stirred for 1 hour. To this mixture was added dropwise a mixture of 12.9 g of chloromethyl ethyl ether and 10 ml of DMF at room temperature, and the mixture was stirred for further 1 hour. The reaction mixture was poured into ice water, and the mixture was extracted three times with ethyl acetate. The organic layers were combined and washed with water and saturated brine and dried over magnesium sulfate. The resulting mixture was concentrated under reduced pressure to obtain 32 g of a crude product of 1-ethoxymethoxy-4-iodobenzene.

A mixture of 7.5 g of the crude product of 1-ethoxymethoxy-4-iodobenzene, 10.0 g of sodium pentafluoropropionate, 10.27 g of copper(I) iodide, 120 ml of DMF and 45 ml of toluene was stirred at 140 to 150° C. for 1 hour to distill about 40 ml of toluene away. The reaction mixture was refluxed at 160 to 170° C. for further 5 hours, then cooled to room temperature, and added to ice water. To this mixture was added 200 ml of diethyl ether. This mixture was filtered through Celite (registered trademark), and the filtrate was extracted with diethyl ether. The combined organic layers were washed with water and saturated brine and dried over magnesium sulfate. The resulting mixture was concentrated under reduced pressure to obtain 5.45 g of 1-ethoxymethoxy-4-(pentafluoroethyl)benzene.

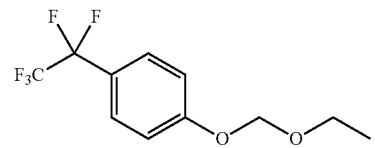 [SMILES: CCOCOc1ccc(C(F)(F)C(F)(F)F)cc1]

$^1$H-NMR (CDCl$_3$) δ: 7.51 (d, J=8.9 Hz, 2H), 7.13 (d, J=8.9 Hz, 2H), 5.27 (s, 2H), 3.73 (q, J=7.0 Hz, 2H), 1.23 (t, J=7.0, 3H)

A mixture of 7.39 g of 1-ethoxymethoxy-4-(pentafluoroethyl)benzene, 30 ml of acetone, and 30 ml of 6 M hydrochloric acid was stirred at 50° C. for 2.5 hours. The reaction mixture was cooled to room temperature and then added to water, and the mixture was extracted with ethyl acetate. The organic layer was washed with water and saturated brine and dried over magnesium sulfate, then concentrated under reduced pressure. The residue was subjected to silica gel column chromatography to obtain 4-(pentafluoroethyl)phenol.

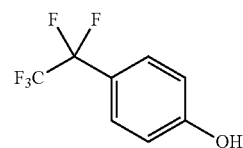 [SMILES: Oc1ccc(C(F)(F)C(F)(F)F)cc1]

$^1$H-NMR (CDCl$_3$) δ: 7.47 (d, J=8.5 Hz, 2H), 6.93 (d, J=8.5 Hz, 2H), 5.74 (br s, 1H)

The same procedures as in Reference Production Example 1 were carried out using 4-(pentafluoroethyl)phenol in place of 4-(trifluoromethyl)phenol, to obtain 2-hydroxy-5-(pentafluoroethyl)benzaldehyde.

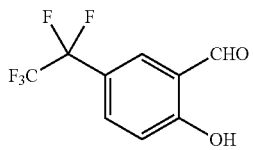 [SMILES: O=Cc1cc(C(F)(F)C(F)(F)F)ccc1O]

¹H-NMR (CDCl₃) δ: 11.32 (s, 1H), 9.98 (t, J=4.6 Hz, 1H), 7.83 (d, J=2.2 Hz, 1H), 7.73 (dd, 8.8, J=2.2 Hz, 1H), 7.13 (d, J=8.8 Hz, 1H)

Reference Production Example 4

To a mixture of 1.53 g of 3-chloroisonicotinaldehyde and 5 ml of ethanol was gradually added 0.40 g of sodium borohydride under ice-cooling, and the mixture was stirred under ice-cooling for 1 hour, and subsequently at room temperature for 1 hour. Saturated brine was added to the reaction mixture, and the mixture was extracted twice with ethyl acetate. The organic layers were combined and dried over magnesium sulfate. The resulting mixture was concentrated under reduced pressure to obtain 1.40 g of (3-chloropyridin-4-yl)methanol.

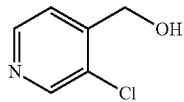

¹H-NMR (CDCl₃) δ: 8.54-8.49 (m, 2H), 7.55-7.51 (m, 1H), 4.83 (d, J=4.4 Hz, 2H), 2.34-2.29 (br m, 1H)

To a mixture of 0.70 g of (3-chloropyridin-4-yl)methanol and 8 ml of chloroform was added dropwise 0.70 g of thionyl chloride at room temperature, and the mixture was stirred at room temperature for 2 hours. A saturated aqueous solution of sodium bicarbonate was added to the reaction mixture, and the mixture was extracted twice with chloroform. The organic layers were combined and dried over magnesium sulfate. The resulting mixture was concentrated under reduced pressure to obtain 0.78 g of 3-chloro-4-(chloromethyl)pyridine.

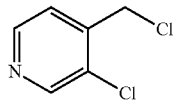

¹H-NMR (CDCl₃) δ: 8.60 (s, 1H), 8.53 (d, J=5.1 Hz, 1H), 7.47-7.46 (m, 1H), 4.66 (s, 2H)

Reference Production Example 5

To a mixture of 1.2 g of 3-fluoroisonicotinaldehyde and 5 ml of ethanol was gradually added 0.36 g of sodium borohydride under ice-cooling, and the mixture was stirred under ice-cooling for 3 hours. Water was added to the reaction mixture, and the mixture was extracted twice with ethyl acetate. The organic layers were combined and washed with saturated brine and dried over magnesium sulfate. The resulting mixture was concentrated under reduced pressure to obtain 1.12 g of (3-fluoropyridin-4-yl)methanol.

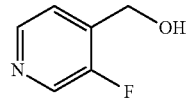

¹H-NMR (CDCl₃) δ: 8.43-8.41 (m, 1H), 8.40 (d, J=1.7 Hz, 1H), 7.51-7.47 (m, 1H), 4.85 (d, J=5.1 Hz, 2H), 2.35-2.30 (br m, 1H)

To a mixture of 1.12 g of (3-fluoropyridin-4-yl)methanol and 5 ml of chloroform was added dropwise 1.26 g of thionyl chloride at room temperature, and the mixture was stirred at room temperature for 1.3 hours. A saturated aqueous solution of sodium bicarbonate was added to the reaction mixture, and the mixture was extracted twice with chloroform. The organic layers were combined and washed with saturated brine and dried over magnesium sulfate. The resulting mixture was concentrated under reduced pressure to obtain 1.22 g of 4-chloromethyl-3-fluoropyridine.

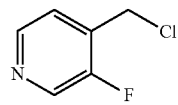

¹H-NMR (CDCl₃) δ: 8.48-8.47 (m, 1H), 8.45 (d, J=4.9 Hz, 1H), 7.44-7.41 (m, 1H), 4.63 (s, 2H)

Next, formulation examples of the present active compounds will be given. Here, "part" represents "part by weight".

Formulation Example 1

Ten parts of any one of the above-described Present Active Compounds (1) to (13) is dissolved in a mixture of 35 parts of xylene and 35 parts of N,N-dimethylformamide, and 14 parts of polyoxyethylene styrylphenyl ether and 6 parts of calcium dodecylbenzenesulfonate are added thereto and mixed to obtain each emulsion.

Formulation Example 2

Four parts of sodium lauryl sulfate, 2 parts of calcium lignin sulfonate, 20 parts of fine powder of synthetic hydrous silicon oxide and 54 parts of diatomaceous earth are mixed, and 20 parts of any one of the above-described Present Active Compounds (1) to (13) is further added thereto and mixed to obtain each wettable powder.

Formulation Example 3

To 2 parts of any one of the above-described Present Active Compounds (1) to (13) are added 1 part of fine powder of synthetic hydrous silicon oxide, 2 parts of calcium lignin sulfonate, 30 parts of bentonite and 65 parts of kaolin clay, and mixed. Subsequently, a suitable amount of water is added to the mixture, and the mixture is further stirred, granulated with a granulator, and air-dried to obtain each granule.

Formulation Example 4

One part of any one of the above-described Present Active Compounds (1) to (13) is dissolved in a suitable amount of acetone, and 5 parts of fine powder of synthetic hydrous silicon oxide, 0.3 parts of PAP and 93.7 parts of Fubasami clay are added to the solution. The mixture is sufficiently stirred and mixed, and acetone is removed by evaporation to obtain each powder.

Formulation Example 5

Thirty-five parts of a mixture of polyoxyethylene alkyl ether sulfate ammonium salt and white carbon (weight ratio of 1:1), 10 parts of any one of the above-described Present Active Compounds (1) to (13) and 55 parts of water are mixed. The mixture is pulverized by wet pulverization method to obtain each formulation.

Formulation Example 6

In 5 parts of xylene and 5 parts of trichloroethane is dissolved 0.1 parts of any one of the above-described Present Active Compounds (1) to (13), and the solution is mixed with 89.9 parts of deodorized kerosene to obtain each oil solution.

Formulation Example 7

In 0.5 ml of acetone is dissolved 10 mg of any one of the above-described Present Active Compounds (1) to (13). This solution is treated into 5 g of solid feed powder for animals (Breeding Solid Feed Powder CE-2, product available from CLEA Japan, Inc.) and mixed homogeneously. Then, acetone is removed by evaporation to obtain each poison bait.

Formulation Example 8

Into an aerosol can are put 0.1 parts of any one of the above-described Present Active Compounds (1) to (13) and 49.9 parts of Neo-chiozol (Chuo Kasei Co., Ltd.), and an aerosol valve is attached to the can. Thereafter, 25 parts of dimethyl ether and 25 parts of LPG are filled in the aerosol can, followed by shaking and attachment of an actuator, to obtain each oil solution aerosol.

Formulation Example 9

A mixture solution of 0.6 parts of any one of the above-described Present Active Compounds (1) to (13), 0.01 parts of BHT (2,6-di-tert-butyl-4-methylphenol), 5 parts of xylene, 3.39 parts of deodorized kerosene and 1 part of an emulsifier {Atmos 300 (registered trade name for ATMOS CHEMICAL LTD)} and 50 parts of distilled water are filled in an aerosol container, and a valve is fixed to the container. Then, 40 parts of a propellant (LPG) is charged under pressure through the valve to obtain each aqueous aerosol.

Next, noxious arthropod controlling effects of the present active compounds are shown by test examples.

Test Example 1

Formulations were prepared by the method described in Formulation Example 5 with respect to each of Present Active Compounds (1) to (3) and (5) to (13). These formulations were diluted with water so as to have a concentration of the active ingredient of 500 ppm to prepare test diluents.

A cucumber seedling (first true leaf development stage) planted in a plastic cup was inoculated with about 30 cotton aphids and allowed to stand for 1 day. To this cucumber seedling, a test diluent (20 ml) was sprayed.

Six days after spraying, the number of survived cotton aphids parasitic on the cucumber leaves was counted, and the control value was calculated by the following equation.

$$\text{Control Value}(\%) = \{1 - (Cb \times Tai)/(Cai \times Tb)\} \times 100$$

wherein each character represents the following meaning:
Cb: the number of insects in non-treated section before treatment
Cai: the number of insects in non-treated section during observation
Tb: the number of insects in treated section before treatment
Tai: the number of insects in treated section during observation As a result, the treated sections treated with Present Active Compound (1) to (3), or (5) to (13) showed a control value of not less than 90%.

Test Example 2

Formulations were prepared by the method described in Formulation Example 5 with respect to each of Present Active Compounds (5), (6) and (7). These formulations were diluted with water so as to have a concentration of the active ingredient of 500 ppm to prepare test diluents.

A plant foot of cucumber seedling (first true leaf development stage) planted in a urethane mat was irrigated with any one of test diluents (5 ml). One day after treatment, the cucumber leaves were inoculated with 30 cotton aphids (all stages). Further, 7 days after, the number of survived cotton aphids parasitic on the cucumber leaves was counted, and the control value was calculated by the following equation.

$$\text{Control Value}(\%) = \{1 - (Cb \times Tai)/(Cai \times Tb)\} \times 100$$

wherein each character represents the following meaning:
Cb: the number of insects in non-treated section before treatment
Cai: the number of insects in non-treated section during observation
Tb: the number of insects in treated section before treatment
Tai: the number of insects in treated section during observation As a result, the treated sections treated with Present Active Compound (5), (6), or (7) showed a control value of not less than 90%.

Test Example 3

Formulations were prepared by the method described in Formulation Example 5 with respect to each of Present Active Compounds (8) and (11). These formulations were diluted with water so as to have a concentration of the active ingredient of 500 ppm to prepare test diluents.

This test diluent (5 ml) was put in a plastic cup. Soil around a cucumber seedling (first true leaf development stage) was removed, and the root part of this seedling was washed with water. The root part of this seedling was immersed in the test diluent put in a plastic cup. After 1 day, the cucumber leaves were inoculated with 30 cotton aphids (all stages). Further, 7 days after, the number of survived cotton aphids parasitic on the cucumber leaves was counted. The control value was calculated by the following equation.

$$\text{Control Value}(\%) = \{1 - (Cb \times Tai)/(Cai \times Tb)\} \times 100$$

wherein each character represents the following meaning:
Cb: the number of insects in non-treated section before treatment
Cai: the number of insects in non-treated section during observation
Tb: the number of insects in treated section before treatment
Tai: the number of insects in treated section during observation As a result, the treated sections treated with Present Active Compound (8) or (11) showed a control value of not less than 90%.

Test Example 4

Formulations were prepared by the method described in Formulation Example 5 with respect to each of Present Active Compounds (1), (3) to (5), and (9) to (13). These formulations were diluted with water so as to have a concentration of the active ingredient of 200 ppm to prepare test diluents.

Tobacco whitefly imagos were released to a tomato seedling (third true leaf development stage) planted in a plastic cup to allow them to lay eggs for about 72 hours. The tomato seedling was kept in a greenhouse for 8 days. Thereafter, a test diluent was sprayed at a rate of 20 ml/cup. The tomato seedling was kept in the greenhouse at 25° C. for further 7 days. Thereafter, the number of survived larvae on tomato leaves was counted, and the control value was calculated by the following equation.

Control Value(%)={1−(Cb×Tai)/(Cai×Tb)}×100 wherein each character represents the following meaning:
Cb: the number of insects in non-treated section before treatment
Cai: the number of insects in non-treated section during observation
Tb: the number of insects in treated section before treatment
Tai: the number of insects in treated section during observation As a result, the treated sections treated with Present Active Compound (I), (3) to (5), or (9) to (13) showed a control value of not less than 90%.

Test Example 5

Formulations were prepared by the method described in Formulation Example 5 with respect to each of Present Active Compounds (1) and (3) to (13). These formulations were diluted with water so as to have a concentration of the active ingredient of 500 ppm to prepare test diluents.

To a rice seedling (two weeks after seeding, second leaf development stage) planted in a plastic cup, a test diluent (10 ml) was sprayed. After the drug solution sprayed on the rice plant was dried, 20 first-instars of rice brown planthopper were released. This rice seedling was kept in a greenhouse at 25° C. for 6 days. Thereafter, the number of rice brown planthopper parasitic on rice plant was counted, and the control value was calculated by the following equation.

Control Value(%)={1−(Cb×Tai)/(Cai×Tb)}×100 wherein each character represents the following meaning:
Cb: the number of insects in non-treated section before treatment
Cai: the number of insects in non-treated section during observation
Tb: the number of insects in treated section before treatment
Tai: the number of insects in treated section during observation As a result, the treated sections treated with Present Active Compound (1) or (3) to (13) showed a control value of not less than 90%.

Test Example 6

Formulations were prepared by the method described in Formulation Example 5 with respect to each of Present Active Compounds (5) and (8). These formulations were diluted with water so as to have a concentration of the active ingredient of 500 ppm to prepare test diluents.

A plant foot of a rice seedling (two weeks after seeding, second leaf development stage) planted in a plastic cup was irrigated with a test diluent (5 ml), and kept in a greenhouse at 25° C. for 7 days. Twenty first-instars of rice brown planthopper were released and kept in the greenhouse for further 6 days. Thereafter, the number of survived rice brown planthopper parasitic on rice plant leaves was counted, and the control value was calculated by the following equation.

Control Value(%)={1−(Cb×Tai)/(Cai×Tb)}×100 wherein each character represents the following meaning:
Cb: the number of insects in non-treated section before treatment
Cai: the number of insects in non-treated section during observation
Tb: the number of insects in treated section before treatment
Tai: the number of insects in treated section during observation As a result, the treated sections treated with Present Active Compound (5) or (8) showed a control value of not less than 90%.

The invention claimed is:
1. A method for controlling a noxious arthropod comprising applying, to noxious arthropods or habitats of noxious arthropods, an effective amount of a heterocyclic compound represented by the formula (1):

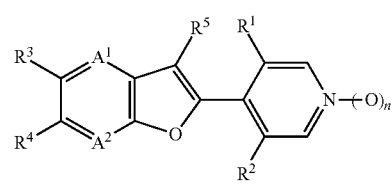

wherein
$A^1$ and $A^2$ are the same or different, and each represent nitrogen or $=C(R^6)-$,
$R^1$ represents a C1 to C6 chain hydrocarbon group optionally substituted with at least one selected from group X, a C3 to C6 alicyclic hydrocarbon group optionally substituted with at least one selected from group X, a phenyl group optionally substituted with at least one selected from group Y, a five-membered heterocyclic group optionally substituted with at least one selected from group Y, a six-membered heterocyclic group optionally substituted with at least one selected from group Y, $-OR^7$, $-S(O)_mR^7$, $-NR^7R^8$, $-NR^7C(O)R^9$, $-NR^7CO_2R^{10}$, $-C(O)R^{11}$, $-C(NOR^7)R^{11}$, $-CO_2R^{11}$, $-CONR^7R^8$, $-CONR^{11}NR^{12}R^{13}$, a cyano group, a nitro group, a halogen, or hydrogen,
$R^2$ represents a C1 to C6 chain hydrocarbon group optionally substituted with at least one selected from group X, $-OR^7$, $-S(O)_mR^7$, $-NR^7R^8$, a halogen, or hydrogen,
$R^3$ and $R^4$ are the same or different, and each represent a C1 to C4 chain hydrocarbon group optionally substituted with at least one selected from group X, a C3 to C6 alicyclic hydrocarbon group optionally substituted with at least one selected from group X, $-OR^{14}$, $-S(O)_mR^{14}$, a halogen, or hydrogen (wherein either $R^3$ or $R^4$ is a C1 to C4 chain hydrocarbon group optionally substituted with at least one selected from group X, a C3 to C6 alicyclic hydrocarbon group optionally substituted with at least one selected from group X, —OR$^{14}$, or —S(O)$_m$R$^{14}$), or R$^3$ and R$^4$ taken together with the atoms to which R$^3$ and R$^4$ are attached may form a five-membered ring or six-membered ring optionally substituted with at least one selected from group Z, R$^5$ represents a C1 to C3 alkyl group optionally substituted with at least one halogen or hydrogen, R$^6$ represents a C1 to C3 alkyl group optionally substituted with at least one halogen or hydrogen, R$^7$ and R$^8$ are the same or different, and each represent a C1 to C6 chain hydrocarbon group optionally substituted with at least one selected from group X, a C4 to C7 cycloalkylmethyl group optionally substituted with at least one selected from group X, a C3 to C6 alicyclic hydrocarbon group optionally substituted with at least one selected from group X, a phenyl group optionally substituted with at least one selected from group Y, a benzyl group optionally substituted with at least one selected from group Y, a five-membered heterocyclic group optionally substituted with at least one selected from group Y, a six-membered heterocyclic group optionally substituted with at least one selected from group Y, or hydrogen (wherein when m in —S(O)$_m$R$^7$ is 1 or 2, R$^7$ is not hydrogen), R$^9$ represents a C1 to C6 chain hydrocarbon group optionally substituted with at least one selected from group X, a C3 to C6 alicyclic hydrocarbon group optionally substituted with at least one selected from group X, or a phenyl group optionally substituted with at least one selected from group Y, R$^{10}$ represents a C1 to C4 alkyl group optionally substituted with at least one halogen, R$^{11}$ represents a C1 to C4 alkyl group optionally substituted with at least one halogen or hydrogen, R$^{12}$ and R$^{13}$ are the same or different, and each represent a C1 to C4 alkyl group optionally substituted with at least one halogen, a C2 to C4 alkoxycarbonyl group, or hydrogen, R$^{14}$ represents a C1 to C4 chain hydrocarbon group optionally substituted with at least one selected from group X, m represents 0, 1, or 2, and n represents 0 or 1:

Group X: a group consisting of C1 to C4 alkoxy groups optionally substituted with at least one halogen and halogens;
Group Y: a group consisting of C1 to C4 alkyl groups optionally substituted with at least one halogen, C1 to C4 alkoxy groups optionally substituted with at least one halogen, a cyano group, a nitro group and halogens; and
Group Z: a group consisting of C1 to C3 alkyl groups optionally substituted with at least one halogen and halogens.

2. The method for controlling a noxious arthropod according to claim 1, wherein the heterocyclic compound represented by the formula (1) is a heterocyclic compound wherein R$^6$ is hydrogen.

3. The method for controlling a noxious arthropod according to claim 1, wherein the heterocyclic compound represented by the formula (1) is a heterocyclic compound wherein R$^2$ is hydrogen.

4. The method for controlling a noxious arthropod according to claim 1, wherein the heterocyclic compound represented by the formula (1) is a heterocyclic compound wherein R$^5$ is hydrogen.

5. The method for controlling a noxious arthropod according to claim 1, wherein the heterocyclic compound represented by the formula (1) is a heterocyclic compound wherein R$^1$ is a C1 to C6 chain hydrocarbon group optionally substituted with at least one selected from group X, —OR$^7$, —S(O)$_m$R$^7$, —NR$^7$R$^8$, —NR$^7$C(O)R$^9$, —NR$^7$CO$_2$R$^{10}$, —C(O)R$^{11}$, —C(NOR$^7$)R$^{11}$, —CO$_2$R$^{11}$, —CONR$^7$R$^8$, —CONR$^{11}$NR$^{12}$R$^{13}$, a cyano group, a nitro group, a halogen, or hydrogen, R$^7$ and R$^8$ are the same or different, and each are a C1 to C6 chain hydrocarbon group optionally substituted with at least one selected from group X or hydrogen (wherein when m in —S(O)$_m$R$^7$ is 1 or 2, R$^7$ represents a C1 to C6 chain hydrocarbon group optionally substituted with at least one selected from group X), and R$^9$ is a C1 to C6 chain hydrocarbon group optionally substituted with at least one selected from group X.

6. The method for controlling a noxious arthropod according to claim 1, wherein the heterocyclic compound represented by the formula (1) is a heterocyclic compound wherein R$^1$ is a C1 to C6 chain hydrocarbon group optionally substituted with at least one selected from group X, —OR$^7$, —S(O)$_m$R$^7$, —NR$^7$R$^8$, a halogen, or hydrogen, R$^7$ is a C1 to C6 chain hydrocarbon group optionally substituted with at least one selected from group X, and R$^8$ is a C1 to C6 chain hydrocarbon group optionally substituted with at least one selected from group X or hydrogen.

7. A heterocyclic compound represented by the formula (2):

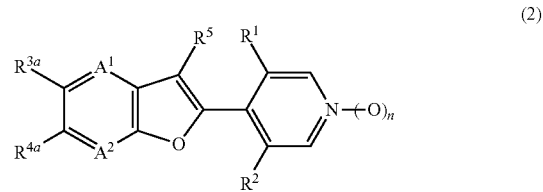

(2)

wherein

A$^1$ and A$^2$ are the same or different, and each represent nitrogen or =C(R$^6$)—, R$^1$ represents a C1 to C6 chain hydrocarbon group optionally substituted with at least one selected from group X, a C3 to C6 alicyclic hydrocarbon group optionally substituted with at least one selected from group X, a phenyl group optionally substituted with at least one selected from group Y, a five-membered heterocyclic group optionally substituted with at least one selected from group Y, a six-membered heterocyclic group optionally substituted with at least one selected from group Y, —OR$^7$, —S(O)$_m$R$^7$, —NR$^7$R$^8$, —NR$^7$C(O)R$^9$, —NR$^7$CO$_2$R$^{10}$, —C(O)R$^{11}$, —C(NOR$^7$)R$^{11}$, —CO$_2$R$^{11}$, —CONR$^7$R$^8$, —CONR$^{11}$NR$^{12}$R$^{13}$, a cyano group, a nitro group, or a halogen, R$^2$ represents a C1 to C6 chain hydrocarbon group optionally substituted with at least one selected from group X, —OR$^7$, —S(O)$_m$R$^7$, —NR$^7$R$^8$, a halogen, or hydrogen, R$^{3a}$ and R$^{4a}$ are the same or different, and each represent a C1 to C4 chain hydrocarbon group substituted with at least one halogen, —OR$^{14a}$, —S(O)$_m$R$^{14a}$, a halogen, or hydrogen (wherein either R$^{3a}$ and R$^{4a}$ is a C1 to C4 chain hydrocarbon group substituted with at least one halogen, —OR$^{14a}$, or —S(O)$_m$R$^{14a}$), or R$^{3a}$ and R$^{4a}$ taken together with the atoms to which R$^{3a}$ and R$^{4a}$ are attached may form a five-membered ring or six-membered ring substituted with at least one halogen, $R^5$ represents a C1 to C3 alkyl group optionally substituted with at least one halogen or hydrogen, $R^6$ represents a C1 to C3 alkyl group optionally substituted with at least one halogen or hydrogen, $R^7$ and $R^8$ are the same or different, and each represent a C1 to C6 chain hydrocarbon group optionally substituted with at least one selected from group X, a C4 to C7 cycloalkylmethyl group optionally substituted with at least one selected from group X, a C3 to C6 alicyclic hydrocarbon group optionally substituted with at least one selected from group X, a phenyl group optionally substituted with at least one selected from group Y, a benzyl group optionally substituted with at least one selected from group Y, a five-membered heterocyclic group optionally substituted with at least one selected from group Y, a six-membered heterocyclic group optionally substituted with at least one selected from group Y, or hydrogen (wherein when m in $-S(O)_mR^7$ is 1 or 2, $R^7$ is not hydrogen), $R^9$ represents a C1 to C6 chain hydrocarbon group optionally substituted with at least one selected from group X, a C3 to C6 alicyclic hydrocarbon group optionally substituted with at least one selected from group X, or a phenyl group optionally substituted with at least one selected from group Y, $R^{10}$ represents a C1 to C4 alkyl group optionally substituted with at least one halogen, $R^{11}$ represents a C1 to C4 alkyl group optionally substituted with at least one halogen or hydrogen, $R^{12}$ and $R^{13}$ are the same or different, and each represent a C1 to C4 alkyl group optionally substituted with at least one halogen, a C2 to C4 alkoxycarbonyl group, or hydrogen, $R^{14a}$ represents a C1 to C4 chain hydrocarbon group substituted with at least one halogen, m represents 0, 1, or 2, and n represents 0 or 1:

Group X: a group consisting of C1 to C4 alkoxy groups optionally substituted with at least one halogen and halogens; and Group Y: a group consisting of C1 to C4 alkyl groups optionally substituted with at least one halogen, C1 to C4 alkoxy groups optionally substituted with at least one halogen, a cyano group, a nitro group, and halogens.

8. The heterocyclic compound according to claim 7, wherein $R^6$ is hydrogen.

9. The heterocyclic compound according to claim 7, wherein $R^2$ is hydrogen.

10. The heterocyclic compound according to claim 7, wherein $R^5$ is hydrogen.

11. The heterocyclic compound according to claim 7, wherein $R^1$ is a C1 to C6 chain hydrocarbon group optionally substituted with at least one selected from group X, $-OR^7$, $-S(O)_mR^7$, $-NR^7R^8$, $-NR^7C(O)R^9$, $-NR^7CO_2R^{10}$, $-C(O)R^{11}$, $-C(NOR^7)R^{11}$, $-CO_2R^{11}$, $-CONR^7R^8$, $-CONR^{11}NR^{12}R^{13}$, a cyano group, a nitro group, or a halogen, $R^7$ and $R^8$ are the same or different, and each are a C1 to C6 chain hydrocarbon group optionally substituted with at least one selected from group X or hydrogen (wherein when m in $-S(O)_mR^7$ is 1 or 2, $R^7$ represents a C1 to C6 chain hydrocarbon group optionally substituted with at least one selected from group X), and $R^9$ is a C1 to C6 chain hydrocarbon group optionally substituted with at least one selected from group X.

12. The heterocyclic compound according to claim 7, wherein $R^1$ is a C1 to C6 chain hydrocarbon group optionally substituted with at least one selected from group X, $-OR^7$, $-S(O)_mR^7$, $-NR^7R^8$, or a halogen, $R^7$ is a C1 to C6 chain hydrocarbon group optionally substituted with at least one selected from group X, and $R^8$ is a C1 to C6 chain hydrocarbon group optionally substituted with at least one selected from group X or hydrogen.

13. The method according to claim 1, wherein $A^1$ and $A^2$ are $=C(R^6)-$, and $R^3$ and $R^4$ are the same or different, and each represent a C1 to C4 chain hydrocarbon group optionally substituted with at least one selected from group X, a C3 to C6 alicyclic hydrocarbon group optionally substituted with at least one selected from group X, $-OR^{14}$, $-S(O)_mR^{14}$, a halogen, or hydrogen (wherein either $R^3$ or $R^4$ is a C1 to C4 chain hydrocarbon group optionally substituted with at least one selected from group X, a C3 to C6 alicyclic hydrocarbon group optionally substituted with at least one selected from group X, $-OR^{14}$, or $-S(O)_mR^{14}$).

14. The heterocyclic compound according to claim 7, wherein $A^1$ and $A^2$ are $=C(R^6)-$, and $R^{3a}$ and $R^{4a}$ are the same or different, and each represent a C1 to C4 chain hydrocarbon group substituted with at least one halogen, $-OR^{14a}$, $-S(O)_mR^{14a}$, a halogen, or hydrogen (wherein either $R^{3a}$ and $R^{4a}$ is a C1 to C4 chain hydrocarbon group substituted with at least one halogen, $-OR^{14a}$, or $-S(O)_mR^{14a}$).

* * * * *